United States Patent
Kostem

(10) Patent No.: US 11,593,649 B2
(45) Date of Patent: Feb. 28, 2023

(54) BASE CALLING USING CONVOLUTIONS

(71) Applicant: Illumina, Inc., San Diego, CA (US)

(72) Inventor: Emrah Kostem, Menlo Park, CA (US)

(73) Assignee: Illumina, Inc., San Diego, CA (US)

(*) Notice: Subject to any disclaimer, the term of this patent is extended or adjusted under 35 U.S.C. 154(b) by 160 days.

(21) Appl. No.: 16/874,633

(22) Filed: May 14, 2020

(65) Prior Publication Data

US 2020/0364565 A1 Nov. 19, 2020

Related U.S. Application Data

(60) Provisional application No. 62/849,132, filed on May 16, 2019, provisional application No. 62/849,133, filed on May 16, 2019, provisional application No. 62/849,091, filed on May 16, 2019.

(51) Int. Cl.
| | |
|---|---|
| *G06N 3/08* | (2006.01) |
| *G06N 3/04* | (2006.01) |
| *G06V 10/75* | (2022.01) |

(52) U.S. Cl.
CPC .......... *G06N 3/08* (2013.01); *G06N 3/04* (2013.01); *G06N 3/0481* (2013.01); *G06V 10/751* (2022.01); *G06V 10/758* (2022.01); *G06V 10/76* (2022.01)

(58) Field of Classification Search
CPC .......... G06N 3/08; G06N 3/04; G06N 3/0481; G06V 10/76; G06V 10/751; G06V 10/758
See application file for complete search history.

(56) References Cited

U.S. PATENT DOCUMENTS

| | | | |
|---|---|---|---|
| 5,641,658 | A | 6/1997 | Adams et al. |
| 6,090,592 | A | 7/2000 | Adams et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |

(Continued)

FOREIGN PATENT DOCUMENTS

| | | |
|---|---|---|
| CA | 2894317 A1 | 12/2016 |
| CA | 3104851 A1 | 11/2020 |

(Continued)

OTHER PUBLICATIONS

NL 2023311 NL Search Report, dated Mar. 24, 2020, 15 pages.

(Continued)

*Primary Examiner* — Kevin Ky
(74) *Attorney, Agent, or Firm* — Keller Preece

(57) ABSTRACT

We propose a neural network-based base caller that detects and accounts for stationary, kinetic, and mechanistic properties of the sequencing process, mapping what is observed at each sequence cycle in the assay data to the underlying sequence of nucleotides. The neural network-based base caller combines the tasks of feature engineering, dimension reduction, discretization, and kinetic modelling into a single end-to-end learning framework. In particular, the neural network-based base caller uses a combination of 3D convolutions, 1D convolutions, and pointwise convolutions to detect and account for assay biases such as phasing and prephasing effect, spatial crosstalk, emission overlap, and fading.

20 Claims, 36 Drawing Sheets
(26 of 36 Drawing Sheet(s) Filed in Color)

Biosensor

(56) References Cited

U.S. PATENT DOCUMENTS

| | | |
|---|---|---|
| 7,329,492 B2 | 2/2008 | Hardin et al. |
| 7,405,281 B2 | 7/2008 | Xu et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 8,182,993 B2 | 5/2012 | Tomaney et al. |
| 8,241,573 B2 | 8/2012 | Banerjee et al. |
| 8,392,126 B2 | 3/2013 | Mann |
| 8,401,258 B2 | 3/2013 | Hargrove et al. |
| 8,407,012 B2 | 3/2013 | Erlich et al. |
| 8,594,439 B2 | 11/2013 | Staelin et al. |
| 8,725,425 B2 | 5/2014 | Heiner et al. |
| 8,795,971 B2 | 8/2014 | Kersey et al. |
| 8,965,076 B2 | 2/2015 | Garcia et al. |
| 9,279,154 B2 | 3/2016 | Previte et al. |
| 9,453,258 B2 | 9/2016 | Kain et al. |
| 9,708,656 B2 | 7/2017 | Turner et al. |
| 10,023,911 B2 | 7/2018 | Tomaney et al. |
| 10,068,054 B2 | 9/2018 | Van Rooyen et al. |
| 10,152,776 B2 | 12/2018 | Langlois et al. |
| 10,168,438 B2 | 1/2019 | Dennis et al. |
| 10,241,075 B2 | 3/2019 | Davey et al. |
| 10,354,747 B1 | 7/2019 | DePristo et al. |
| 10,423,861 B2 | 9/2019 | Gao et al. |
| 10,491,239 B1 | 11/2019 | Hubara |
| 10,527,549 B2 | 1/2020 | Rebetez et al. |
| 10,540,591 B2 | 1/2020 | Gao et al. |
| 10,619,195 B2 | 4/2020 | Lamb et al. |
| 10,648,027 B2 | 5/2020 | Mannion et al. |
| 10,711,299 B2 | 7/2020 | Rothberg et al. |
| 10,713,794 B1 * | 7/2020 | He .................. G06N 3/0454 |
| 10,740,880 B2 * | 8/2020 | Paik .................. G06T 7/194 |
| 10,740,883 B2 | 8/2020 | Zerfass et al. |
| 10,755,810 B2 * | 8/2020 | Buckler ............. G16H 30/40 |
| 10,963,673 B2 | 3/2021 | Schaumberg et al. |
| 11,138,496 B2 | 10/2021 | Seth |
| 2002/0055100 A1 | 5/2002 | Kawashima et al. |
| 2003/0062485 A1 | 4/2003 | Fernandez et al. |
| 2004/0002090 A1 | 1/2004 | Mayer et al. |
| 2004/0096853 A1 | 5/2004 | Mayer |
| 2006/0014151 A1 | 1/2006 | Ogura et al. |
| 2006/0040297 A1 | 2/2006 | Leamon et al. |
| 2006/0064248 A1 | 3/2006 | Saidi et al. |
| 2006/0188901 A1 | 8/2006 | Barnes et al. |
| 2006/0240439 A1 | 10/2006 | Smith et al. |
| 2006/0269130 A1 | 11/2006 | Maroy et al. |
| 2007/0128624 A1 | 6/2007 | Gormley et al. |
| 2007/0166705 A1 | 7/2007 | Milton et al. |
| 2008/0009420 A1 | 1/2008 | Schroth et al. |
| 2008/0234136 A1 | 9/2008 | Drmanac et al. |
| 2008/0242560 A1 | 10/2008 | Gunderson et al. |
| 2009/0081775 A1 | 3/2009 | Hodneland et al. |
| 2010/0046830 A1 | 2/2010 | Wang et al. |
| 2010/0111370 A1 | 5/2010 | Black et al. |
| 2010/0157086 A1 | 6/2010 | Segale et al. |
| 2011/0059865 A1 | 3/2011 | Smith et al. |
| 2011/0065607 A1 | 3/2011 | Kersey et al. |
| 2011/0281736 A1 | 11/2011 | Drmanac et al. |
| 2011/0286628 A1 | 11/2011 | Goncalves et al. |
| 2011/0295902 A1 | 12/2011 | Mande et al. |
| 2012/0015825 A1 | 1/2012 | Zhong et al. |
| 2012/0020537 A1 | 1/2012 | Garcia et al. |
| 2013/0059740 A1 | 3/2013 | Drmanac et al. |
| 2013/0079232 A1 | 3/2013 | Kain et al. |
| 2013/0124100 A1 | 5/2013 | Drmanac et al. |
| 2013/0188866 A1 | 7/2013 | Obrador et al. |
| 2013/0250407 A1 | 9/2013 | Schaffer et al. |
| 2014/0051588 A9 | 2/2014 | Drmanac et al. |
| 2014/0152801 A1 | 6/2014 | Fine et al. |
| 2015/0079596 A1 | 3/2015 | Eltoukhy et al. |
| 2015/0117784 A1 | 4/2015 | Lin et al. |
| 2015/0169824 A1 | 6/2015 | Kermani et al. |
| 2016/0042511 A1 | 2/2016 | Chukka et al. |
| 2016/0078272 A1 | 3/2016 | Hammoud |
| 2016/0110498 A1 | 4/2016 | Bruand et al. |
| 2016/0196479 A1 | 7/2016 | Chertok et al. |
| 2016/0350914 A1 * | 12/2016 | Champlin .............. G06V 10/56 |
| 2016/0356715 A1 | 12/2016 | Zhong et al. |
| 2016/0357903 A1 | 12/2016 | Shendure et al. |
| 2016/0371431 A1 | 12/2016 | Haque et al. |
| 2017/0044601 A1 | 2/2017 | Crnogorac et al. |
| 2017/0098032 A1 | 4/2017 | Desai et al. |
| 2017/0116520 A1 | 4/2017 | Min et al. |
| 2017/0161545 A1 * | 6/2017 | Champlin ............ G06V 20/695 |
| 2017/0169313 A1 | 6/2017 | Choi et al. |
| 2017/0249421 A1 | 8/2017 | Eberle et al. |
| 2017/0249744 A1 | 8/2017 | Wang et al. |
| 2017/0362634 A1 | 12/2017 | Ota et al. |
| 2018/0075279 A1 | 3/2018 | Gertych et al. |
| 2018/0107927 A1 | 4/2018 | Frey |
| 2018/0114337 A1 | 4/2018 | Li et al. |
| 2018/0189613 A1 | 7/2018 | Wolf et al. |
| 2018/0195953 A1 | 7/2018 | Langlois et al. |
| 2018/0201992 A1 | 7/2018 | Wu et al. |
| 2018/0211001 A1 | 7/2018 | Gopalan et al. |
| 2018/0274023 A1 | 9/2018 | Belitz et al. |
| 2018/0305751 A1 | 10/2018 | Vermaas et al. |
| 2018/0322327 A1 | 11/2018 | Smith et al. |
| 2018/0330824 A1 | 11/2018 | Athey |
| 2018/0334711 A1 | 11/2018 | Kelley et al. |
| 2018/0334712 A1 | 11/2018 | Singer et al. |
| 2018/0340234 A1 | 11/2018 | Scafe et al. |
| 2019/0034586 A1 | 1/2019 | Pirrotte et al. |
| 2019/0080450 A1 | 3/2019 | Arar et al. |
| 2019/0107642 A1 | 4/2019 | Farhadi Nia et al. |
| 2019/0114544 A1 | 4/2019 | Sundaram et al. |
| 2019/0156915 A1 | 5/2019 | Zhang et al. |
| 2019/0164010 A1 | 5/2019 | Ma et al. |
| 2019/0170680 A1 | 6/2019 | Sikora et al. |
| 2019/0180153 A1 * | 6/2019 | Buckler ............... G06V 20/698 |
| 2019/0213473 A1 | 7/2019 | Dutta et al. |
| 2019/0237160 A1 | 8/2019 | Rothberg et al. |
| 2019/0237163 A1 | 8/2019 | Wang et al. |
| 2019/0244348 A1 * | 8/2019 | Buckler ............... G06N 20/00 |
| 2019/0266491 A1 | 8/2019 | Gao et al. |
| 2019/0272638 A1 | 9/2019 | Mouton et al. |
| 2019/0332118 A1 | 10/2019 | Wang et al. |
| 2019/0392578 A1 | 12/2019 | Chukka et al. |
| 2020/0027002 A1 | 1/2020 | Hickson et al. |
| 2020/0054306 A1 | 2/2020 | Mehanian et al. |
| 2020/0057838 A1 | 2/2020 | Yekhanin et al. |
| 2020/0065675 A1 | 2/2020 | Sundaram et al. |
| 2020/0125947 A1 | 4/2020 | Park et al. |
| 2020/0176082 A1 | 6/2020 | Massingham |
| 2020/0193597 A1 | 6/2020 | Fan et al. |
| 2020/0226368 A1 * | 7/2020 | Bakalo ............... G06K 9/00536 |
| 2020/0256856 A1 * | 8/2020 | Chou ................. G01N 15/06 |
| 2020/0302223 A1 | 9/2020 | Dutta et al. |
| 2020/0302224 A1 | 9/2020 | Jaganathan et al. |
| 2020/0302297 A1 | 9/2020 | Jaganathan et al. |
| 2020/0302603 A1 | 9/2020 | Barnes et al. |
| 2020/0320294 A1 | 10/2020 | Mangal et al. |
| 2020/0342955 A1 | 10/2020 | Guo et al. |
| 2020/0364565 A1 * | 11/2020 | Kostem ................. G06N 3/04 |
| 2020/0388029 A1 | 12/2020 | Saltz et al. |
| 2021/0027462 A1 | 1/2021 | Bredno et al. |
| 2021/0056287 A1 | 2/2021 | Schaumburg et al. |
| 2021/0072391 A1 | 3/2021 | Li et al. |
| 2021/0089827 A1 | 3/2021 | Kumagai et al. |
| 2021/0115490 A1 | 4/2021 | Embree et al. |
| 2021/0390278 A1 * | 12/2021 | Van Leeuwen .......... G06T 7/11 |

FOREIGN PATENT DOCUMENTS

| | | |
|---|---|---|
| CN | 110245685 A | 9/2019 |
| EP | 3130681 A1 | 2/2017 |
| EP | 3373238 A1 | 9/2018 |
| JP | 2007199397 A | 8/2007 |
| WO | 9106678 A1 | 5/1991 |
| WO | 2004018497 A2 | 3/2004 |
| WO | 2005065814 A1 | 7/2005 |
| WO | 2006064199 A1 | 6/2006 |
| WO | 2007010251 A2 | 1/2007 |

(56) References Cited

FOREIGN PATENT DOCUMENTS

| | | |
|---|---|---|
| WO | 2007123744 A2 | 11/2007 |
| WO | 2008154317 A1 | 12/2008 |
| WO | 2012058096 A1 | 5/2012 |
| WO | 2014142921 A1 | 9/2014 |
| WO | 2015084985 A2 | 6/2015 |
| WO | 2016145516 A1 | 9/2016 |
| WO | 2016201564 A1 | 12/2016 |
| WO | 2017184997 A1 | 10/2017 |
| WO | 2018129314 A1 | 7/2018 |
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |

OTHER PUBLICATIONS

NL 2023312, NL Search Report, dated Mar. 24, 2020, 22 pages.
NL 2023317, NL Search Report, dated Mar. 24, 2020, 16 pages.
NL 2023316, NL Search Report, dated Mar. 23, 2020, 15 pages.
MX/a/2020/014288 First Office Action, dated Mar. 10, 2021, 2 pages.
MX/a/2020/014288 Response to First Office Action, dated May 5, 2021, 390 pages.
U.S. Appl. No. 16/825,991—Notice of Allowance dated Aug. 5, 2021, 10 pages.
Krishnakumar et al., Systematic and stochastic influences on the performance of the MinION nanopore sequencer across a range of nucleotide bias. Scientific Reports, published Feb. 16, 2018, 13 pages.
Tegfalk, Application of Machine Learning techniques to perform base-calling in next-generation DNA sequencing, KTH Royal Institue of Technology, dated 2020, 53 pages.
U.S. Appl. No. 16/826,168—Office Action dated Aug. 31, 2021, 55 pages.
Kircher-etal_Improved-base-calling-for-the-Illumina-Genome-Analyzer-using-machine-learning-strategies_14August2009_10pages.
Albrecht et al., Deep learning for single molecule science, Nanotechnology, dated Sep. 18, 2017, 11 pages.
U.S. Appl. No. 16/825,987—Office Action (Quayle) dated Oct. 19, 2021, 85 pages.
PCT/US2021047763—International Search Report and Written Opinion, dated Dec. 20, 2021, 11 pages.
PCT/US2021/018422 Second Written Opinion, dated Feb. 4, 2022, 8 pages.
Adriana Romero et al., FitNets: Hints for Thin Deep Nets, published Mar. 27, 2015, 13 pages.
U.S. Appl. No. 16/874,599—Notice of Allowance dated Dec. 3, 2021, 12 pages.
U.S. Appl. No. 16/825,987—Response to Office Action (Quayle) dated Oct. 19, 2021, filed Jan. 13, 2022, 11 pages.
U.S. Appl. No. 16/825,987—Notice of Allowance, dated Jan. 28, 2022, 12 pages.
U.S. Appl. No. 16/825,987—Supplemental Notice of Allowance, dated Feb. 7, 2022, 8 pages.
U.S. Appl. No. 16/826,168—Response to Office Action dated Aug. 31, 2021, filed Jan. 31, 2022,15 pages.
CN 2020800036223—Voluntary Amendments, filed May 20, 2021, 26 pages.

EP 20719053.9—Rules 161(2) and 162 Communication, dated Oct. 28, 2021, 3 pages.
IL 279522—Notice Before Acceptance (in Hebrew), dated Aug. 1, 2021, 2 pages.
IL 279522—Response to Notice Before Acceptance dated Aug. 1, 2021, filed Nov. 28, 2021, 3 pages.
KR 10-2020-7037712—Voluntary Amendments with translation, dated Nov. 9, 2021, 7 pages.
EP 20719052.1—Rules 161(1) and 162 Communication, dated Oct. 28, 2021. 3 pages.
IL 279525—Notice Before Acceptance (in Hebrew), dated Aug. 1, 2021, 2 pages.
IL 279525—Response to Notice Before Acceptance dated Aug. 1, 2021, filed Nov. 28, 2021, 4 pages.
KR 10-2020-7037713—Voluntary Amendments with translation, dated Nov. 9, 2021, 26 pages.
ZA 2020/07998—Notice of Allowance, dated Aug. 12, 2021, 2 pages.
EP 20718112.4—Rules 161(2) and 162 Communication, dated Oct. 28, 2021, 3 pages.
IL 279527—Notice Before Examination (in Hebrew), dated Aug. 1, 2021, 2 pages.
IL 279527—Response to Notice Before Examination dated Aug. 1, 2021, filed Nov. 28, 2021, 3 pages.
KR 10-2021-7003269—Voluntary Amendments with translation, dated Nov. 9, 2021, 7 pages.
ZA 2020/07999—Notice of Allowance, dated Aug. 12, 2021, 2 pages.
EP 20719294.9—Rules 161(1) and 162 Communication, dated Oct. 28, 2021, 3 pages.
IL 281668—Notice Before Examination, dated Oct. 10, 2021, 2 pages.
IL 281668—Response to Notice Before Examination dated Oct. 10, 2021, filed Feb. 8, 2022, 4 pages.
KR 10-2021-7009877—Voluntary Amendments with translation, dated Nov. 9, 2021, 21 pages.
EP 20757979.8—Rules 161(2) and 162 Communication, dated Oct. 28, 2021, 3 pages.
IL 279533—Notice Before Examination, dated Aug. 1, 2021, 2 pages.
IL 279533—Response to Notice Before Examination dated Aug. 1, 2021, filed Nov. 29, 2021, 3 pages.
KR 10-2021-7003270—Voluntary Amendments with translation, dated Nov. 9, 2021, 29 pages.
ZA 2020/08000—Notice of Acceptance, dated Aug. 12, 2021, 2 pages.
Robinson et al., Computational Exome and Genome Analysis—Chapter 3 Illumina Technology, dated 2018, 25 pages.
Wang et al., An adaptive decorrelation method removes Illumina DNA base-calling errors caused by crosstalk between adjacent clusters—with Supplemental Materials, Scientific Reports, published Feb. 20, 2017, 17 pages.
PCT/US2020/033280—International Preliminary Reporton Patentability, dated Jul. 23, 2021, 11 pages.
Pfeiffer et al., Systematic evaluation of error rates and causes in short samples in next-generation sequencing, Scientific Reports, published Jul. 19, 2018, 14 pages.
PCT/US2020/033281—International Preliminary Reporton Patentability, dated Aug. 31, 2021, 10 pages.
PCT/US2021/018422 International Search Report and Written Opinion, dated Jun. 10, 2021, 12 pages.
Aggarwal, Neural Networks and Deep Learning: A Textbook, Springer, dated Aug. 26, 2018, 512 pages.
Wang et al., Deep Neural Netwotk Approximation for Custom Hardware: Where We've Been, Where We're Going, Cornell University, dated Jan. 21, 2019, 37 pages.
Lavin et al., Fast Algorithms for Convolutional Neural Networks, dated Nov. 10, 2015, 9 pages.
Liu et al., A Uniform Architecture Design for Accelerating 2D and 3D CNNs on FPGAs, published Jan. 7, 2019, 19 pages.
PCT/US2021/018427 International Search Report and Written Opinion, dated Jun. 1, 2021, 15 pages.

(56) References Cited

OTHER PUBLICATIONS

PCT/US2021/018913 International Search Report and Written Opinion, dated Jun. 10, 2021, 11 pages.
Zeng et al., Causalcall: Nanopore Basecalling Using a Temporal Convolutional Network, dated Jan. 20, 2020, 11 pages.
PCT/US2021/018915 International Search Report and Written Opinion, dated Jun. 15, 2021, 13 pages.
Kwon et al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et al., Efficient Processing of Deep Neural Networks: A Tutorial and Survey, Cornell University Library, dated Mar. 27, 2017, 21 pages.
Sundaram, L. et al., "Predicitng the clinical impact of human mutation with deep neural networks", Nat. Genet. 50, 1161-1170 (2018).
Jaganathan, K. et al., "Predicting splicing from primary sequence with deep learning", Cell 176, 535-548, (2019).
Kircher, Martin, et al. "A general framework for estimating the relative pathogenicity of human genetic variants." Nature genetics 46.3 (2014): 310. (Year:2014).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in oseudogenes and its evolutionary implications. J. Molec. Evol. 21, 58-71 (1984).
Grantham, R. Amino acid difference formula to help explain protein evolution. Science 185, 862-864 (1974).
LeCun, Y., Botlou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonicde novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X. Need, A. C., Petrovski, S. & Goldstein, D. B. One gene, many neuropsychiatric disorders: lessons from Mendelian diseases. Nat. Neurosci. 17, 773-781, (2014).
Leffler, E. M. et al. Revisiting an old riddle: what determines genetic diversity levels within species? PLoS Biol. 10, e1001388 (2012), 9pages.
Estrada, A. et al. Impending extinction crisis of the worid's primates—why primates matter. Sc. Adv. 3, e1600946 (2017), 17 pages.
Kent, W. J. et al. The human genome browser at UCSC. Genome Res. 12, 996-1006 (2002).
Tyner, C. et al. The UCSC Genome Browser database—2017 update. Nucleic Acids Res. 45, D626-D634 (2017).
Kabsch, W., & Sander, C. Dictionary of protein secondary structure—pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K, Zhang, X., Ren, S., & Sun, J. Identity mappings in deep residual networks. in 14th European Conference on Computer Vision—ECCV 2016. ECCV 2016. Lecture Notes in Computer Science, vol. 9908; 630 6,15 (Springer, Cham, Switzerland; 2016).
Ionita-Laza, I., McCallum, K., Xu, B., & Buxbaum, J. D. A spectral approach integrating functional genomic annotations tor coding and noncoding variants. Nat. Genet. 48, 214-220 (2016).
Li, B. et al. Automated inference of molecular mechanisms of disease from amino acid substitutions. Bioinformatics 25, 2744-2750 (2009).
Lu, Q. et al. A statistical framework to predict functional non-coding regions in the human genome through integrated analysis of annotation data Sci. Rep 5, 10576 (2015), 13pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. PLoS Comput. Biol. 6, Dec. 2, 2010, 13 pages.
Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).
De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability—an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Gilissen, C. et al. Genome sequencing identifies major causes of severe intellectual disability. Nature 511, 344-347 (2014).
Lelieveld, S. H. et al. Meta-analysis of 2,104 trios provides support for 10 new genes for intellectual disability. Nat. Neurosci. 19, 1194-1196 (2016).
Famiglietti, M. L. et al. Genetic variations and diseases in UniProtKB Swiss-Prot—the ins and outs of expert manual curation. Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).
Min, et al., "Deep Learning in Bioinformatics", Jun. 19, 2016, 46pgs.
Jiminez et al., DeepSite—protein binding site predictor using 3D CNNs, dated Oct. 1, 2017, 7 pages.
Pu et al., "DeepDrug3D: Classification of ligand-binding pockets in proteins with a convolutional neural network", dated Feb. 4, 2019, 23 pages.
Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et. al., "Predicting changes in protein thermostability upon mutation with deep 3D convolutional neural networks", dated Feb. 28, 2020, 21 pages.
Raschka et. al., "Machine Learning and AI-based approaches for bioactive ligand discovery and GPCR-ligand recognition", dated Jun. 6, 2020, 33 pages.

(56) References Cited

OTHER PUBLICATIONS

Morrone et al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et. al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Anonymous, "Transferrable end-to-end learning for protein interface prediction", dated 2019, 12 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.
Li et. al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Illumina, Low-diversity sequencing on the Illumina HiSeq Platform, 2014, 2 pages.
Hedegaard, An introduction to "Next Generation" DNA Sequencing, dated Nov. 26, 2017, 63 pages.
Jordan, An overview of semantic image segmentation, dated May 21, 2018, 28 pages retrieved on Jul. 21, 2021. Retrieved from the internet [URL: https://www.jeremyjordan.me/semantic-segmentation/ ].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/ ].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing—Assessing sequencing accuracy using Phred quality scoring, 2011, 2 pages.
Restrepo, A Gentle Introduction to Semantic Segmentation—Inputs, Labels and Outputs, 2 pages, retrieved on Jul. 21, 2021 Retrieved from [URL: http://ronny.rest/tutorials/module/seg_01/segmentation_03_inputs_outputs/].
Illumina, An Introduction to Next-Generation Sequencing Technology, 2017, 16 pages.
Belanovic, Library of Parameterized Hardware Modules for Floating-Point Arithmetic with an Example Application, Northeastern University, Boston, MA, May 2002, 83 pages.
Massingham, Base Calling: methods, problems and alternatives, EMBL Advanced Course in Analysis of Short Read Sequencing Data, Jun. 8, 2009-Jun. 10, 2009, 84 pages.
Thoma, A Survey of Semantic Segmentation, dated May 11, 2016, 16 pages.
Rodriguez-Ezpeleta, Bioinformatics for High Throughput Sequencing, Springer, 2012, 266 pages.
Illumina, Optimizing Cluster Density on Illumina Sequencing Systems, 2016, 12 pages.
Boza et al., DeepNano: Deep recurrent neural networks for base calling in MinION nanopore reads, PLOS ONE, dated Jun. 5, 2017, 13 pages.
Kircher, Understanding and Improving high-throughput sequencing data production and analysis, Leipzig University, 2011, 216 pages.
Lutteropp, Error-Profile-Aware Correction of Next Generation Sequencing Reads, Karlsruhe Institute of Technology, dated Mar. 31, 2017, 96 pages.
Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.
Zhou et. al., Incorporating Side-Channel Information into Convolutional Neural Networks for Robotic Tasks, 2017, 7 pages.
Linder, Modeling the intronic regulation of Alternative Splicing using Deep Convolutional Neural Nets, KTH Institute of Technology, dated Jun. 14, 2015, 53 pages.
Bentley et. al., Accurate Whole Human Genome Sequencing using Reversible Terminator Chemistry, Nature, Nov. 2008, 21 pages.
Illumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Albrecht et. al., Deep learning for single-molecule science, Nanotechnology (28), dated 2017, 423001, 11 pages.
MiSEQ: Imaging and Base Calling: Illumina, Inc. Online Training Course, dated Jan. 1, 2013 [retrieved on Jul. 13, 2020], Retrieved from <URL: https://support.illumina.com/training.html >, 13 pages.
MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/extemal_files/MiSeq%20Imaging%20and%20Base%20Calling%20Script.pdf >.
PCT/US2020/024087 PCT Direct Letter, dated Mar. 21, 2020, 5 pages.
PCT/US2020/024087 International Search Report and Written Opinion, dated Aug. 28, 2020, 24 pages.
PCT/US2020/024087 Article 34 Amendment, filed Mar. 21, 2020, 7 pages.
PCT/US2020/024087 Second Written Opinion, dated Apr. 7, 2021, 12 pages.
PCT/US2020/024087 Article 34 Letter Response to Second Written Opinion, dated May 7, 2021, 7 pages.
Zhao et. al., Object detection with Deep Learning: A Review, dated Jul. 15, 2018, 22 pages.
Lee et. al., Fast Object Localization Using a CNN Feature Map Based Multi-Scale Search, dated Apr. 12, 2016, 16 pages.
PCT/US2020/24088 PCT Direct Letter, filed Mar. 21, 2020, 4 pages.
PCT/US2020/024088 Article 34 Letter in response to Second Written Opinion, dated May 28, 2021, 9 pages.
PCT/US2020/024088 Second Written Opinion, dated Apr. 20, 2021, 17 pages.
PCT/US2020/024088 International Search Report and Written Opinion, dated Sep. 7, 2020, 29 pages.
PCT/US2020/024088 Article 34 Letter in Response to Written Opinion, dated Mar. 9, 2021, 11 pages.

(56) References Cited

OTHER PUBLICATIONS

PCT/US2020/024088 Partial Search Report and Invitation to Pay Fees, dated Jul. 8, 2020, 22 pages.
Misiunas et. al., QuipuNet: convolutional neural network for single-molecule nanopore sensing, dated May 30, 2018, 7 pages.
Boza et. al., Deep Recurrent Neural Networks for Base Calling in MinION Nanopore Reads, dated Mar. 30, 2016, 12 pages.
Kao et. al., BayesCall: A model-based base-calling algorithm for high-throughput short-read sequencing, Genome Research (19), pp. 1884-1895, dated 2009.
Rang et. al., From squiggle to basepair: computational approaches for improving nanopore sequencing read accuracy, Genome Biology 2018, (19), 30.
Wang et. al., An adaptive decorrelation method removes Illumina DNA base-calling errors caused by crosstalk between adjacent clusters, Scientific Reports, published Feb. 20, 2017, 11 pages.
Cacho et. al., A comparison of Base Calling Algorithms for Illumina Sequencing Technology, dated Oct. 5, 2015, Briefings in Bioinformatics 2016 (17), 786-795.
PCT/US2020/024091 PCT Direct Letter, dated Mar. 21, 2020, 5 pages.
PCT/US2020/024091 Partial Search Report and Invitation to Pay Fee, dated Jul. 3, 2020, 17 pages.
PCT/US2020/024091 International Search Report and Written Opinion, dated Oct. 23, 2020, 24 pages.
PCT/US2020/024091 Article 34 Letter in Reponse to International Search Report and Written Opinion, filed Mar. 8, 2021, 10 pages.
PCT/US2020/024091 Second Article 34 Amendment Letter, dated Mar. 22, 2021, 10 pages.
PCT/US2020/024091 Written Opinion of the International Preliminary Examining Authority (Second Written Opinon), dated Apr. 20, 2021, 14 pages.
PCT/US2020/024091 Second Article 34 Amendment in response to Second Written Opinion, dated May 30, 2021, 9 pages.
Luo et. al., G-softmax: Improving Intra-class Compactness and Inter-class Separability of Features, dated Apr. 8, 2019, 15 pages.
Luo et. al., A multi-task convolutional deep neural network for variant calling in single molecule sequencing, Nature Communications (10), No. 1, dated Mar. 1, 2019.
Kingma et. al., Adam: A method for Stochastic Optimization, ICLR 2015, dated Jul. 23, 2015.
Luo et. al., Skyhawk: An Artificial Neural Network-based discriminator for reviewing clinically significant genomic variants, dated Jan. 28, 2019, 8 pages.
MiSEQ: Imaging and Base Calling: Illumina, Inc. Online Training Course, colored version, [retrieved on Oct. 11, 2020], Retrieved from <URL: https://support.illumina.com/training.html >, 9 pages.
PCT/US2020/024092 PCT Direct Letter, dated Mar. 21, 2020, 5 pages.
PCT/US2020/024092 Partial Search Report and Invitation to Pay Fees, dated Sep. 11, 2020, 22 pages.
PCT/US2020/024092 International Search Report and Written Opinion, dated Nov. 2, 2020, 24 pages.
PCT/US2020/024092 Article 34 Amendment in Response to International Search Report and Written Opinion, dated Mar. 4, 20221, 7 pages.
PCT/US2020/024092 Second Written Opinion dated Apr. 7, 2021, 13 pages.
PCT/US2020/024092 Article 34 Amendment Response to Second Written Opinion, dated May 7, 2021, 10 pages.
PCT/US2021/018910—Partial Search Report and Invitation to Pay Fees dated May 31, 2021, 14 pgs.
PCT/US2020/033280 International Search Report and Written Opinion, dated Jul. 22, 2020, 18 pages.
PCT/US2020/033280 Article 34 Amendment, dated Apr. 19, 2021, 10 pages.
PCT/US2020/033281 International Search Report and Written Opinion, dated Aug. 14, 2020, 15 pages.
Kircher et. al., Improved base-calling for the Illumina Genome Analyzer using Machine Learning Strategies, Genome Biology, published Aug. 14, 2009, 9 pages.
PCT/US2020/033281 Second Written Opinion, dated May 10, 2021, 8 pages.
Angermueller, Christof, et. al., Deep learning for computational biology, Molecular Systems Biology, dated Jun. 6, 2016, 16 pages.
PCT/US2021/018258 International Search Report and Written Opinion, dated May 26, 2021, 17 pages.
Smith et. al., Barcoding and demultiplexing Oxford nanopore native RNA sequencing reads with deep residual learning, bioRxiv, dated Dec. 5, 2019, 18 pages.
PCT/US2021/018910 Partial Search Report and Invitation to pay fee, dated May 31, 2021, 14 pages.
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
U.S. Appl. No. 16/825,991—Notice of Allowance dated Apr. 19, 2021, 14 pages.
Arpali et. al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et. al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.
Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord, Dieleman et. al., Wavenet: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et. al., Highway Networks, 2015.
Huang et. al., Densely Connected Convolutional Networks, 2017.
Szegedy et. al., Going Deeper with Convolutions, 2014.
Ioffe et. al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.

(56) References Cited

OTHER PUBLICATIONS

Piqueras, Autoregressive Model Based on a Deep Convolutional Neural Network for Audio Generation, Tampere University of Technology, 2016.
Wu, Introduction to Convolutional Neural Networks, Nanjing University, 2017.
Scikit-image/peak.py at master, Github, retrieved on Jun. 8, 2021, 10 pages, Retrieved from the internet <URL: https://github.com/scikit-image/scikit-image/blob/main/skimage/feature/peakpy>.
3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.
Mordvintsev et. al., Image Segmentation with Watershed Algorithm, Revision 43532856, 2013, 6 pages, [retrieved on Jun. 8, 2021] Retrieved from the Internet <URL: https://opencv-python-tutroals.readthedocs.io/en/latest/py_tutorials/py_imgproc/py_watershed/py_watershed.html>.
Mzur, Watershed.py, Github, 3 pages, [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network, International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.
Assem, Predicting periodic and chaotic signals using Wavenets, Master of Science thesis, Delft University of Technology, Aug. 18, 2017, pp. 3-38.
Goodfellow et al., Convolutional Networks, Deep Learning, MIT Press, 2016.
Illumina, "Indexed Sequencing Overview Guide", Document No. 15057455, v. 5, Mar. 2019.
PCT/US2020/024090 International Preliminary Report on Patentability, dated Apr. 13, 2021, 20 pages.
PCT/US2020/024090 Written Opinion of the International Preliminary Examining Authority, dated Dec. 22, 2020, 11 pages.
PCT/US2020/024090 PCT Direct Letter, filed Mar. 21, 2020, 5 pages.
PCT/US2020/024090 International Search Report, dated Aug. 31, 2020, 8 pages.
PCT/US2020/024090 Article 34 Amendment, dated Dec. 4, 2020, 6 pages.
PCT/US2020/024090 Article 34 Amendment, dated Mar. 18, 2021, 3 pages.
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaaI4326 (2017), 19 pages.
Nakamura, K. et al. Clinical spectrum of SCN2A mutations expanding to Ohtahara syndrome. Neurology 81, 992-998 (2013).
Ioannidis, Nilah M., et al., "REVEL—An Ensemble Method for Predicting the Pathogenicity of Rare Missense Variants", Oct. 5, 2016, 9 pages.
Quang Daniel, et. al., "DANN—a deep learning approach for annotating the pathogenicity of genetic variants", Oct. 22, 2014, 3 pages.
Sundaram, et. al., "Predicting the clinical impact of human mutation with deep neural networks", Aug. 2018, 15pgs.
Xiong, et. al., "The human splicing code reveals new insights into the genetic determinants of disease", Jan. 9, 2015, 20pgs.
Yue, et. al., "Deep Learning for Genomics—A Concise Overview from internet", May 8, 2018, 40pgs.
Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et. al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et. al., "Selene—a PyTorch based deep learning library for sequence level data", Oct. 10, 2018, 15pages.
Grob, C., et. al., "Predicting variant deleteriousness in non human species Applying the CADD approach in mouse", 2018, 11 pages.
Li, et. al., "FoldingZero—Protein Folding from Scratch in Hydrophobic Polar Model", Dec. 3, 2018, 10 pages.
Rentzsch, et al.,_"CADD—predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
PCT/US2018/055840—International Search Report and Written Opinion dated Jan. 25, 2019, 18 pages.
Wei etal_The Role of Balanced Training and Testing Data Sets for Binary Classifiers in Bioinformatics dated Jul. 9, 2013 12 pages.
PCT/US2018/055878—International Search Report and Written Opinion dated Jan. 22, 2019, 20 pages.
PCT/US2018/055881—International Search Report and Written Opinion dated Jan. 25, 2019, 17 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.

(56) References Cited

OTHER PUBLICATIONS

Bahar, Protein Actions Principles and Modeling, Chapter 7, 2017 pp. 165-166.

Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.

DbSNP rs2241788 [Retrieved on Mar. 13, 2019], Retrieved from the Internet<www.ncbi.nlm.nih.gov/snp/rs2241788>, 5 pages.

Wei, et. al., "Prediction of phenotypes of missense mutations in human proteins from biological assemblies", Feb. 2013, 28 pages.

Zhang, Jun, and Bin Liu. "PSFM-DBT—identifying DNA-binding proteins by combing position specific frequency matrix and distance-bigram transformation."International journal of molecular sciences 18.9(2017) 1856.

Gao, Tingting, et al. "Identifying translation initiation sites in prokaryotes using support vector machine." Journal of theoretical biology 262.4 (2010) 644-649. (Year 2010).

Bi, Yingtao, et al. "Tree-based position weight matrix approach to model transcription factor binding site profiles." PloS one6.9(2011) e24210.

Korhonen, Janne H., et al. "Fast motif matching revisited—high-order PWMs, SNPs and indels." Bioinformatics 33.4 (2016) 514-521.

Wong, Sebastien C., et al. "Understanding data augmentation for classification—when to warp?." 2016 international conference on digital image computing—techniques and applications (DICTA) IEEE, 2016.

Chang, Chia-Yun, et al. "Oversampling to overcome overtitling—exploring the relationship between data set composition, molecular descriptors, and predictive modeling methods." Journal of chemical information and modeling 53.4 (2013) 958-971.

Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.

Martin-Navarro, Antonio, et al. "Machine learning classifier for identification of damaging missense mutations exclusive to human mitochondrial DNA-encoded polypeptides." BMC bioinformatics 18.1 (2017) p. 158.

Krizhevsky, Alex, et al, ImageNet Classification with Deep Convolutional Neural Networks, 2012, 9 Pages.

Geeks for Geeks, "Underfitting and Overfilling in Machine Learning", [retrieved on Aug. 26, 2019]. Retrieved from the Internet <www.geeksforgeeks.org/underfitting-and-overfitting-in-machine-learning/>, 2 pages.

Despois, Julien, "Memorizing is not learning!—6 tricks to prevent overfitting in machine learning", Mar. 20, 2018, 17 pages.

Bhande, Anup What is underfitting and overfitting in machine learning and how to deal with it, Mar. 11, 2018, 10pages.

PCT/US2019031621—International Search Report and Written Opinion dated Aug. 7, 2019, 17 pages.

Carter et al., "Cancer-specific high-throughput annotation of somatic mutations—computational prediction of driver missense mutations," Cancer research 69, No. 16 (2009) pp. 6660-6667.

Stenson, P. D. et al. The Human Gene Mutation Database—building a comprehensive mutation repository for clinical and molecular genetics, diagnostic testing and personalized genomic medicine. Hum. Genet. 133, 1-9 (2014).

Alipanahi, et. al., "Predicting the Sequence Specificities of DNA and RNA Binding Proteins by Deep Learning", Aug. 2015, 9pgs.

Angermueller, et. al., "Accurate Prediction of Single Cell DNA Methylation States Using Deep Learning", Apr. 11, 2017, 13pgs.

Ching, et. al., "Opportunities and Obstacles for Deep Learning in Biology and Medicine", Jan. 19, 2018, 123pgs.

Ching, et. al., "Opportunities and Obstacles for Deep Learning in Biology and Medicine", May 26, 2017, 47pgs.

Gu, et. al., "Recent Advances in Convolutional Neural Networks", Jan. 5, 2017, 37pgs.

Leung, et. al., "Deep learning of the tissue regulated splicing code", 2014, 9pgs.

Leung, et. al., "Inference of the Human Polyadenylation Code", Apr. 27, 2017, 13pgs.

Leung, et. al., "Machine Learning in Genomic Medicine", Jan. 1, 2016, 22pgs.

Park, et. al., "Deep Learning for Regulatory Genomics", Aug. 2015, 2pgs.

MacArthur, D. G. et al. Guidelines for investigating causality of sequence variants in human disease. Nature 508, 469-476 (2014).

Rehm, H. L. et al. ClinGen—the Clinical Genome Resource. N. Engl. J. Med. 372, 2235-2242 (2015).

Bamshad, M. J. et al. Exome sequencing as a tool for Mendelian disease gene discovery. Nat. Rev. Genet. 12, 745-755 (2011).

Rehm, H. L. Evolving health care through personal genomics. Nat. Rev. Genet. 18, 259-267 (2017).

Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).

Lek, M. et al. Analysis of protein-coding genetic variation in 60,706 humans. Nature 536, 285-291 (2016).

Mallick, S. et al. The Simons Genome Diversity Project—300 genomes from 142 diverse populations. Nature 538, 201-206 (2016).

Genomes Project Consortium. et al. A global reference for human genetic variation. Nature 526, 68-74 (2015).

Liu, X., Jian, X. & Boerwinkle, E. dbNSFP—a lightweight database of human nonsynonymous SNPs and their functional predictions. Human. Mutat. 32, 894-899 (2011).

Chimpanzee Sequencing Analysis Consortium. Initial sequence of the chimpanzee genome and comparison with the human genome. Nature 437, 69-87 (2005).

Takahata, N. Allelic genealogy and human evolution. Mol. Biol. Evol. 10, 2-22 (1993).

Asthana, S., Schmidt, S., & Sunyaev, S. A limited role for balancing selection. Trends Genet. 21, 30-32 (2005).

Leffler, E. M. et al. Multiple instances of ancient balancing selection shared between humans and chimpanzees. Science 339, 12 pages (2013).

Samocha, K. E. et al. A framework for the interpretation of de novo mutation in human disease. Nat. Genet. 46, 944-950 (2014).

Ohta, T. Slightly deleterious mutant substitutions in evolution. Nature 246, 96-98 (1973).

Reich, D. E. & Lander, E. S. On the allelic spectrum of human disease. Trends Genet. 17, 502-510 (2001).

Whiffin, N. et al. Using high-resolution variant frequencies to empower clinical genome interpretation. Genet. Med. 19, 1151-1158(2017).

Prado-Martinez, J. et al. Great ape genome diversity and population history. Nature 499, 471-475 (2013).

Klein, J., Satta, Y., O'HUigin, C., & Takahata, N. The molecular descent of the major histocompatibility complex. Annu. Rev. Immunol. 11, 269-295 (1993).

De Manuel, M. et al. Chimpanzee genomic diversity reveals ancient admixture with bonobos. Science 354,477-481 (2016).

Locke, D. P. et al. Comparative and demographic analysis of orang-utan genomes. Nature 469, 529-533 (2011).

Rhesus Macaque Genome Sequencing Analysis Consortium. Evolutionary and biomedical insights from the rhesus macaque genome. Science 316, 222-234 (2007).

Worley, K. C. et al. The common marmoset genome provides insight into primate biology and evolution. Nat. Genet. 46, 850-857 (2014).

Sherry, S. T. et al. dbSNP—the NCBI database of genetic variation. Nucleic Acids Res. 29, 308-211 (2001).

Schrago, C. G., & Russo, C. A. Timing the origin of New World monkeys. Mol. Biol. Evol. 20, 1620-1625 (2003).

Landrum, M. J. et al. ClinVar—public archive of interpretations of clinically relevant variants. Nucleic Acids Res. 44, D862-868 (2016).

Brandon, E. P., Idzerda, R. L. & McKnight, G. S. Targeting the mouse genome—a compendium of knockouts (Part II). Curr. Biol. 5, 758-765 (1995).

Lieschke, J. G. & Currie, P. D. Animal models of human disease—zebrafish swim into view. Nat. Rev. Genet. 8, 353-367 (2007).

(56) References Cited

OTHER PUBLICATIONS

Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations—application to cancer genomics. Nucleic Acids Res. 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels. PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
PCT/US2021/018258—Second Written Opinion, dated Jan. 25, 2022, 11 pages.
PCT/US2021/018910—International Search Report and Written Opinion, dated Aug. 25, 2021, 24 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
PCT/US2021/018910—Article 34 Amendment, filed Dec. 19, 2021, 9 pages.
PCT/US2021/018910—Second Written Opinion, dated Feb. 21, 2022, 17 pages.
PCT/US2021/018422—Article 34 Amendment, dated Dec. 20, 2021, 7 pages.
PCT/US/2021/018427—Second Written Opinion, dated Feb. 4, 2022, 9 pages.
PCT/US/2021/018427—Article 34 Amendment, filed Dec. 19, 2021, 7 pages.
PCT/US2021/018913—Second Written Opinion, dated Feb. 4, 2022, 8 pages.
Ye et al., BlindCall: ultra-fast base-calling of high-throughput sequencing data by blind deconvolution, Bioinformatics, vol. 30, No. 9, dated Jan. 9, 2014, pp. 1214-1219, 6 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
PCT/US2021/018913—Article 34 Amendment, filed Dec. 19, 2021, 18 pages.
PCT/US2021/018915—Second Written Opinion, dated Feb. 4, 2022, 9 pages.
PCT/US2021/018915—Article 34 Amendment, filed Dec. 19, 2021, 7 pages.
PCT/US2021/018917—Second Written Opinion, dated Feb. 4, 2022, 7 pages.
PCT/US2021/018917—Article 34 Amendment, filed Dec. 19, 2021, 6 pages.
U.S. Appl. No. 17/468,411—Office Action, dated Feb. 24, 2022, 36 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.
Forghani et al., Convolutional Neural Network Based Approach to In Silico Non-Anticipating Prediction of Antigenic Distance for Influenza Virus, Viruses, published Sep. 12, 2020, vol. 12, 20 pages.
Jing et al., Learning from protein structure with geometric vector perceptrons, Arxiv: 2009: 01411v2, dated Dec. 31, 2020, 18 pages.
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et. al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23, 2021. Retrieved from [URL: https://boofcv.org/index.php?title=Tutorial_Image_Segmentation ].
Illumina, Understanding Illumina Quality Scores, dated Apr. 23, 2014, 2 pages.
Yue et. al., Deep Learning for Genomics: A Concise Overview, dated May 8, 2018, 40 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].

(56) References Cited

OTHER PUBLICATIONS

Teng et. al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et. al., Chiron: translating nanopore raw signal directly into nucleotide sequence using deep learning, dated Aug. 23, 2017, 10 pages.
Stoiber et. al., BasecRAWller: Streaming Nanopore Basecalling Directly from Raw Signal, dated May 1, 2017, 15 pages.
Li et. al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, pp. 489-497, dated Jan. 18, 2011, 9 pages.
Sheikh et. al., Chapter 5 Base-Calling for Bioinformaticians, 2012, 17 pages.
Kriseman et. al., BING: Biomedical informatics pipeline for Next Generation Sequencing, Journal of Biomedical Informatics, vol. 43, 2010, pp. 428-434, 7 pages.
Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Wolowski, High-quality, high-throughput measurement of protein-DNA binding using HiTS-FLIP, Ludwig Maxmilian University, 2016, 251 pages.
Bravo et. al., Model-Based Quality Assessment and Base-Calling for Second-Generation Sequencing Data, Biometrics, 2009, 10 pages.
Illumina, RTA Theory of Operation, 2009, 8 pages.
Dash et. al., Artificial Intelligence and Evolutionary Computations in Engineering Systems, Advances in Intelligent Systems and Computing, vol. 1056, Springer 2020, 781 pages.
Ahmed, SIGNET: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Baek et. al., LncRNAnet: long non-coding RNA identification using deep learning, Bioinformatics, vol. 34 (22), 2018, pp. 3889-3897, 9 pages.
Evans et. al., Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Wang et. al., DeepDNA: a hybrid convolutional and recurrent neural network for compressing human mitochondrial genomes, IEEE International Conference on Bioinformatics and Biomedicine, 2018, 5 pages.
PCT/US2020/024092, International Preliminary Report on Patentability (IPRP), dated Jun. 30, 2021, 30 pages.
PCT/US2020/024091 International Preliminary Report and Patentability (IPRP), dated Jun. 30, 2021, 32 pages.
PCT/US2020/024088 International Preliminary Report on Patentability (IPRP), dated Jun. 30, 2021, 35 pages.
PCT/US2020/024087 International Preliminary Report on Patentability (IPRP), dated Jun. 30, 2021, 26 pages.
PCT/US2021/018917 Internation Search Report and Written Opinion, dated Jul. 1, 2021, 15 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
PCT/US2020/033281, Second Article 34 Amendment Letter in response to Second Written Opinion, dated Jul. 10, 2021, 4 pages.
U.S. Appl. No. 16/825,987, filed Mar. 20, 2020, U.S. Pat. No. 11,347,965, dated May 31, 2022, Issued.
U.S. Appl. No. 16/825,991, filed Mar. 20, 2020, U.S. Pat. No. 11,210,554, dated Dec. 28, 2021, Issued.
U.S. Appl. No. 16/826,126, filed Mar. 20, 2020, US-2020-0302297-A1, dated Sep. 24, 2020, Pending.
U.S. Appl. No. 16/826,134, filed Mar. 20, 2020, US-2020-0327377-A1, dated Oct. 15, 2020, Pending.
U.S. Appl. No. 16/826,168, filed Mar. 21, 2020, US-2020-0302224-A1, dated Sep. 24, 2020, Allowed.
U.S. Appl. No. 17/529,222, filed Nov. 17, 2021, US-2022-0147760-A1, dated May 12, 2022, Pending.
U.S. Appl. No. 17/827,612, filed May 27, 2022, Pending.
U.S. Appl. No. 17/899,539, filed Aug. 30, 2022, Pending.
U.S. Appl. No. 17/703,975, filed Mar. 24, 2022, Pending.
U.S. Appl. No. 17/175,546, filed Feb. 12, 2021, US-2021-0265009-A1, dated Aug. 26, 2021, Pending.
U.S. Appl. No. 17/180,542, filed Feb. 19, 2021, US-2021-0265017-A1, dated Aug. 26, 2021, Pending.
U.S. Appl. No. 17/176,151, filed Feb. 15, 2021, US-2021-0265018-A1, dated Aug. 26, 2021, Pending.
U.S. Appl. No. 17/411,980, filed Aug. 25, 2021, US-2022-0067489-A1, dated Mar. 3, 2022, Pending.
U.S. Appl. No. 17/687,551, filed Mar. 4, 2022, Pending.
U.S. Appl. No. 17/687,583, filed Mar. 4, 2022, Pending.
U.S. Appl. No. 17/176,147, filed Feb. 15, 2021, US-2021-0265015-A1, dated Aug. 26, 2021, Pending.
U.S. Appl. No. 17/876,528, filed Jul. 28, 2022, Pending.
U.S. Appl. No. 17/179,395, filed Feb. 18, 2021, US-2021-0265016-A1, dated Aug. 26, 2021, Pending.
U.S. Appl. No. 17/180,480, filed Feb. 19, 2021, US-2021-0264266-A1, dated Aug. 26, 2021, Pending.
U.S. Appl. No. 17/180,513, filed Feb. 19, 2021, US-2021-0264267-A1, dated Aug. 26, 2021, Pending.
U.S. Appl. No. 17/687,586, filed Mar. 4, 2022, Pending.
U.S. Appl. No. 17/232,056, filed Apr. 15, 2021, Pending.
U.S. Appl. No. 17/468,411, filed Sep. 7, 2021, Allowed.
U.S. Appl. No. 17/830,287, filed Jun. 1, 2022, Pending.
U.S. Appl. No. 17/830,316, filed Jun. 1, 2022, Pending.
U.S. Appl. No. 17/839,387, filed Jun. 13, 2022, Pending.
U.S. Appl. No. 17/839,331, filed Jun. 13, 2022, Pending.
U.S. Appl. No. 17/703,935, filed Mar. 24, 2022, Pending.
U.S. Appl. No. 17/703,958, filed Mar. 24, 2022, Pending.
PCT/US2020/033280, filed May 15, 2020, WO 2020/232409, dated Nov. 19, 2020, Nationalized.
PCT/US2020/033281, filed May 15, 2020, WO 2020/232410, dated Nov. 19, 2020, Nationalized.
PCT/US2020/024090, filed Mar. 21, 2020, WO 2020/191389, dated Sep. 24, 2020, Nationalized.
PCT/US2020/024087, filed Mar. 21, 2020, WO 2020/205296, dated Oct. 8, 2020, Nationalized.
PCT/US2020/024088, filed Mar. 21, 2020, WO 2020/191387, dated Sep. 24, 2020, Nationalized.
PCT/US2020/024091, filed Mar. 21, 2020, WO 2020/191390, dated Sep. 24, 2020, Nationalized.
PCT/US2020/024092, filed Mar. 22, 2020, WO 2020/191391, dated Sep. 24, 2020, Nationalized.

(56) References Cited

OTHER PUBLICATIONS

PCT/US2021/018258, filed Feb. 16, 2021, Pending.
PCT/US2021/018910, filed Feb. 19, 2021, Pending.
PCT/US2021/018422, filed Feb. 17, 2021, Pending.
PCT/US2021/047763, filed Aug. 26, 2021, Pending.
PCT/US2022/020460, filed Mar. 15, 2022, Pending.
PCT/US2022/020462, filed Mar. 15, 2022, Pending.
PCT/US2021/018427, filed Feb. 17, 2021, Pending.
PCT/US2022/039208, filed Aug. 2, 2022, Pending.
PCT/US2021/018913, filed Feb. 19, 2021, Pending.
PCT/US2021/018915, filed Feb. 19, 2021, Pending.
PCT/US2021/018917, filed Feb. 19, 2021, Pending.
PCT/US2022/021814, filed Mar. 24, 2022, Pending.
PCT/US2022/24911, filed Apr. 14, 2022, Pending.
PCT/US2022/24913, filed Apr. 14, 2022, Pending.
PCT/US2022/035564, filed Jun. 29, 2022, Pending.
PCT/US2022/035567, filed Jun. 29, 2022, Pending.
PCT/US2022/035847, filed Jun. 30, 2022, Pending.
PCT/US2022/24916, filed Apr. 14, 2022, Pending.
PCT/US2022/24918, filed Apr. 14, 2022, Pending.
Hacteria Wiki, HiSeq2000 - Next Level Hacking - Hackteria Wiki, retrieved on Apr. 12, 2021, retrieved from the internet URL: https://www.hackteria.org/wiki/HiSeq2000_-_Next_Level_Hacking ], 42 pages.
Pei et al., A Topological Measurement for Weighted Protein Interaction Network, IEEE Computational Systems Bioinformatics Conference dated 2005, 11 pages. no date available.
Assfalg et al., "3DString, A Feature String Kernel for 3D Object Classification on Voxelized Data", dated Nov. 6, 2006, 10 pages.

\* cited by examiner

Biosensor
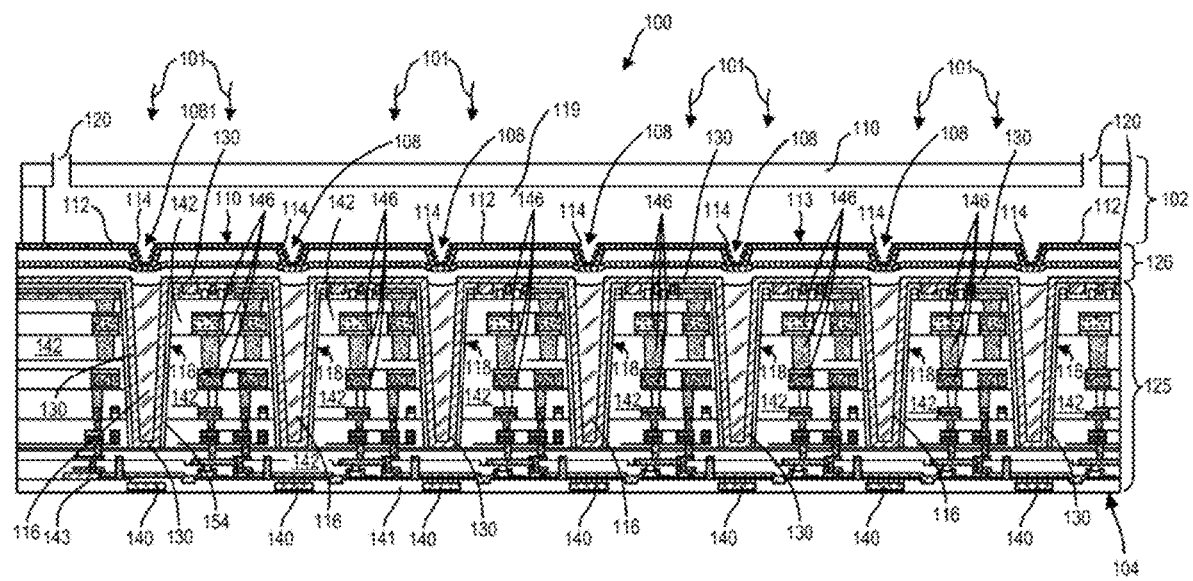
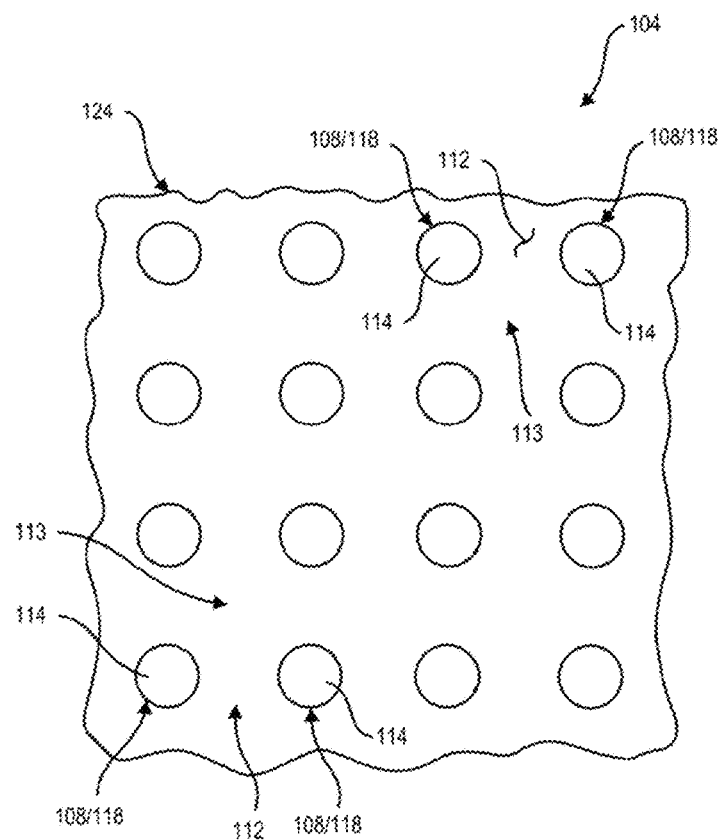
FIG. 1

Detection Device
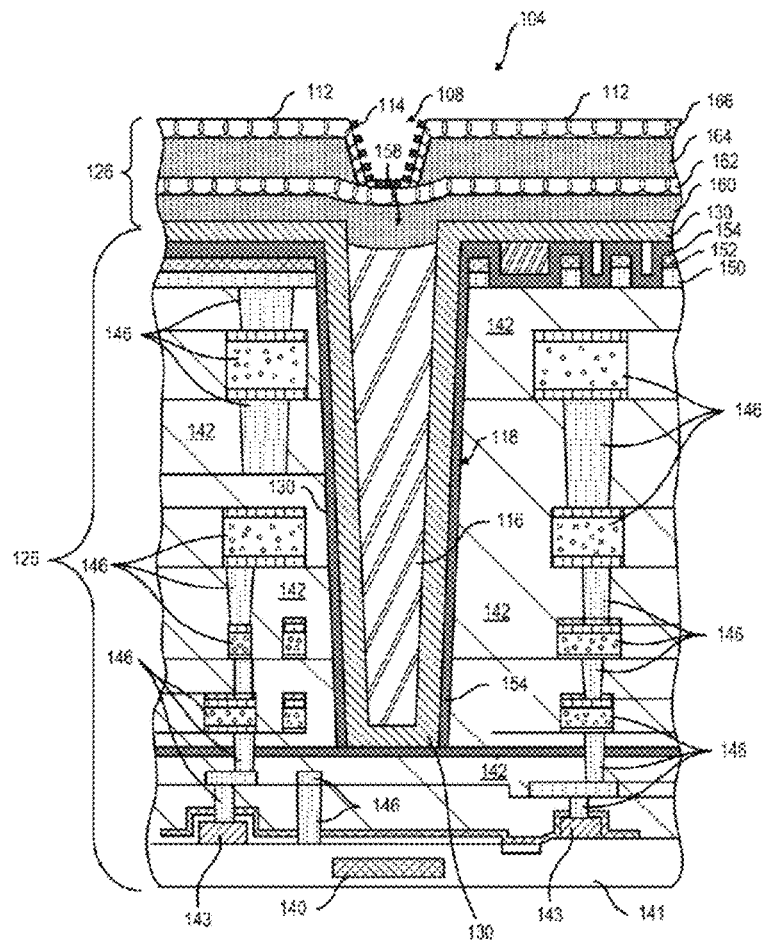
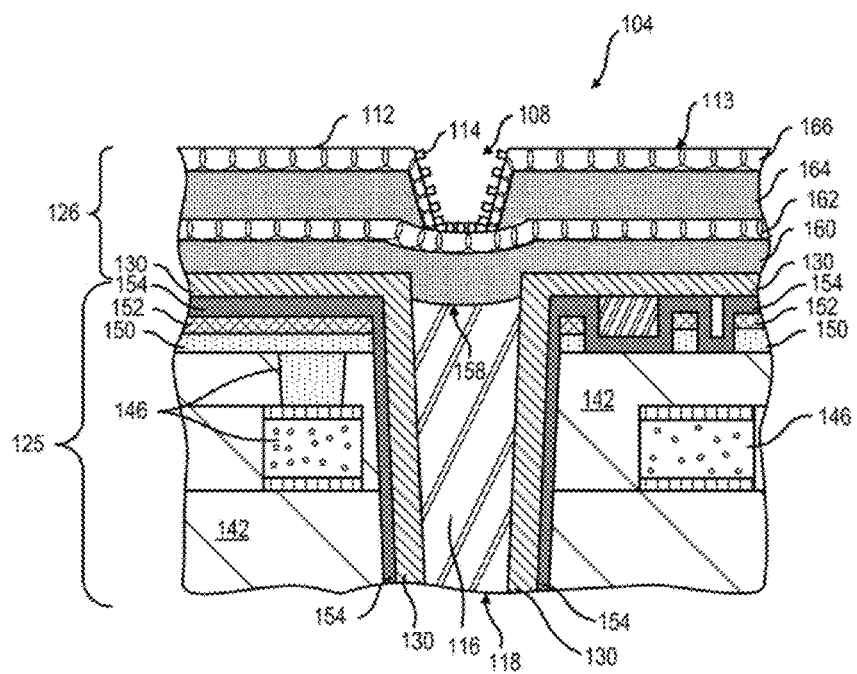
FIG. 2

Phasing and Prephasing Data

FIG. 18

Convolution Kernel

| a | b | c |
|---|---|---|

1816 ↪ recurrent transposed convolutions between the convolution kernel and its output (e.g., zero padding, one stride)

1806 α

1800

| | $i_1$ | $i_2$ | $i_3$ | $i_4$ | $i_5$ | $i_6$ | $i_7$ | $i_8$ | $i_9$ | $i_{10}$ | ... | $i_k$ |
|---|---|---|---|---|---|---|---|---|---|---|---|---|
| 1804 Cycle 1 | 1 | 0 | 0 | 0 | 0 | 0 | 0 | 0 | 0 | 0 | ... | 0 |
| 1814 Cycle 2 | $a$ | $b$ | $c$ | 0 | 0 | 0 | 0 | 0 | 0 | 0 | ... | 0 |
| 1824 Cycle 3 | $a^2$ | $2ab$ | $2ac+b^2$ | $2bc$ | $c^2$ | 0 | 0 | 0 | 0 | 0 | ... | 0 |
| 1834 Cycle 4 | $a^3$ | $3a^2b$ | $3a^2c+3ab^2$ | $3abc+b^3$ | $3ac^2+3b^2c$ | $3bc^2$ | $c^3$ | 0 | 0 | 0 | ... | 0 |
| 1844 Cycle 5 | $a^4$ | $4a^3b$ | $6a^3c+6a^2b^2$ | $9a^2bc+4ab^3$ | $6a^2c^2+9ab^2c+b^4$ | $9abc^2+4b^3c$ | $4ac^3+6b^2c^2$ | $6bc^3$ | $c^4$ | 0 | ... | 0 |
| ... | ... | ... | ... | ... | ... | ... | ... | ... | ... | ... | ... | ... |
| Cycle k | ... | ... | ... | ... | ... | ... | ... | ... | ... | ... | ... | $c^{k-1}$ |

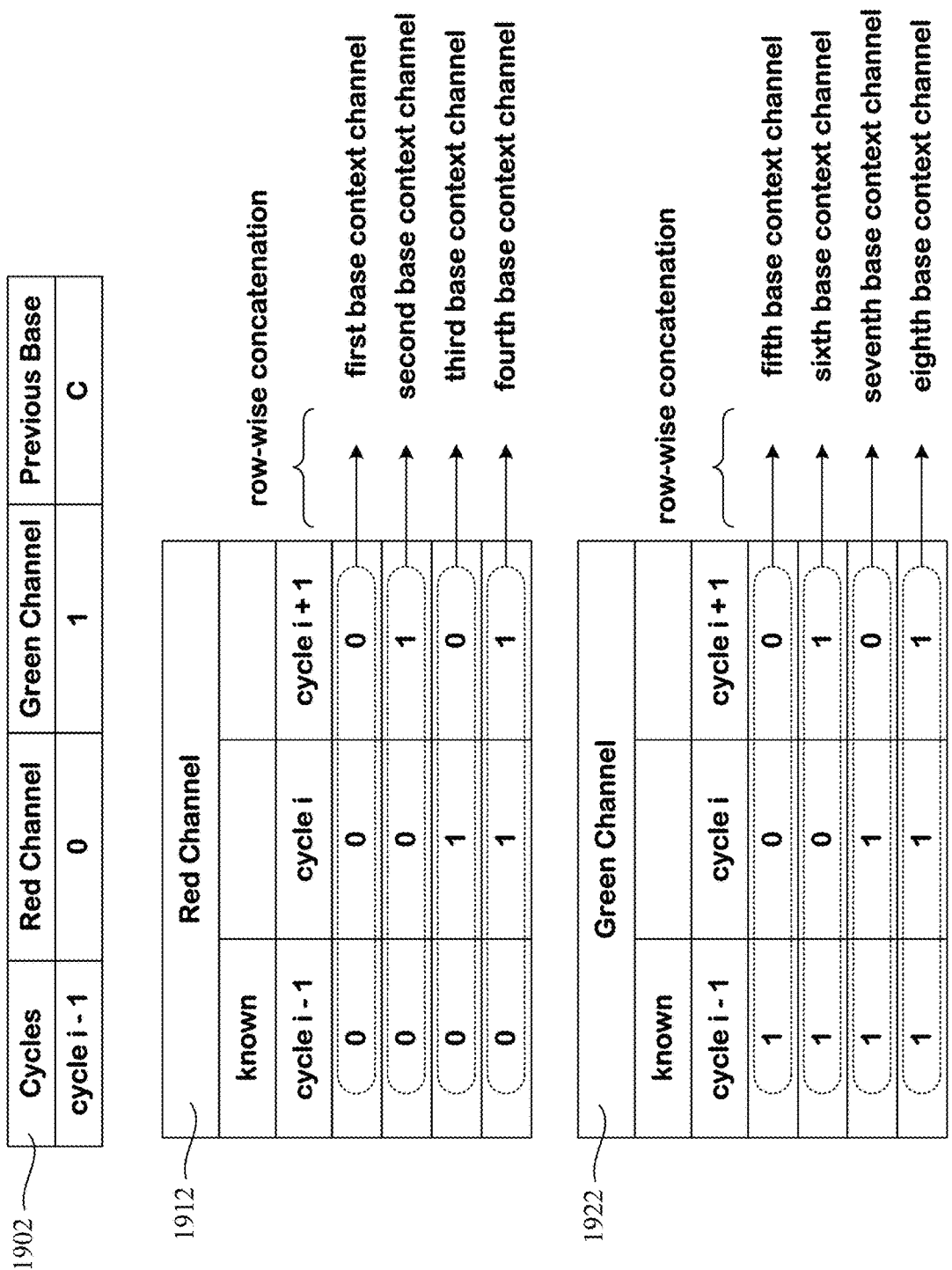

Base Context Data (Five Cycles)
| | Cycles | Red Channel | Green Channel | Previous Base |
|---|---|---|---|---|
| 2002 | cycle i - 2 | 1 | 0 | A |
| 2004 | cycle i - 1 | 0 | 1 | C |
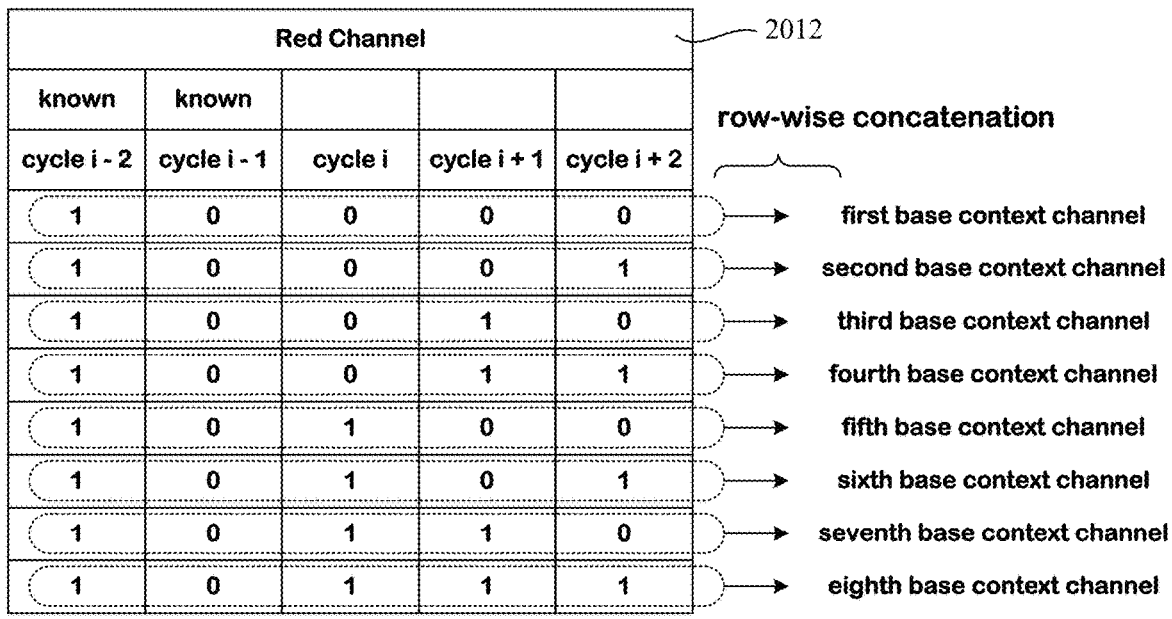
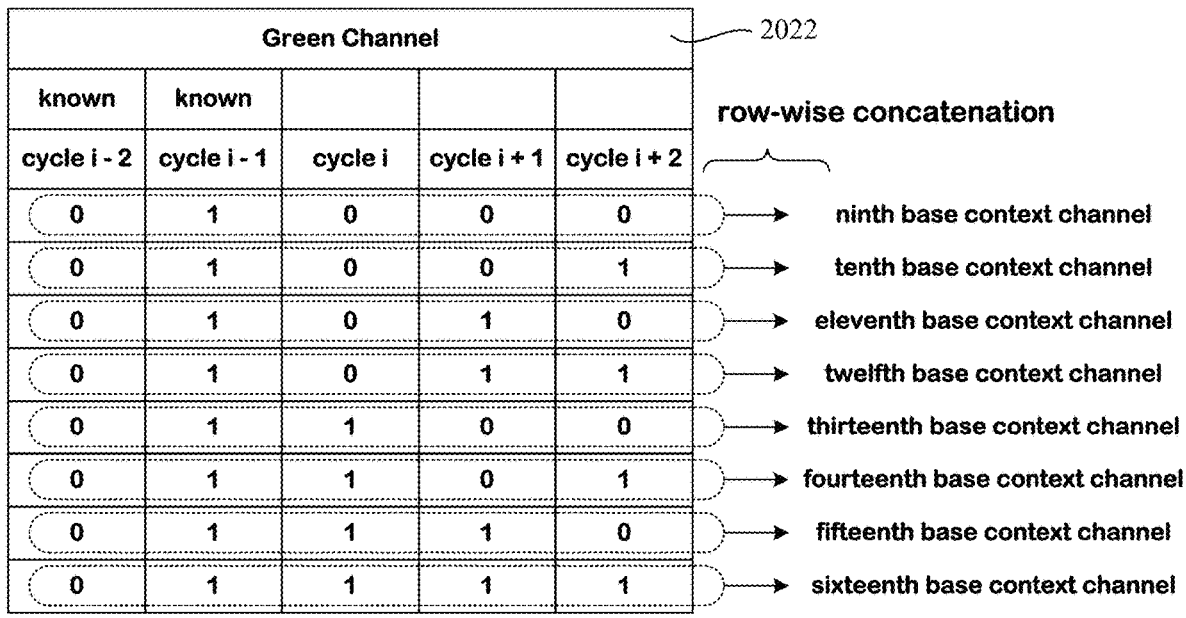
FIG. 20

FIG. 23 Convolutions in a Timestep of Compact Base Calling (3 Cycles)

Phasing and Prephasing Effect
a
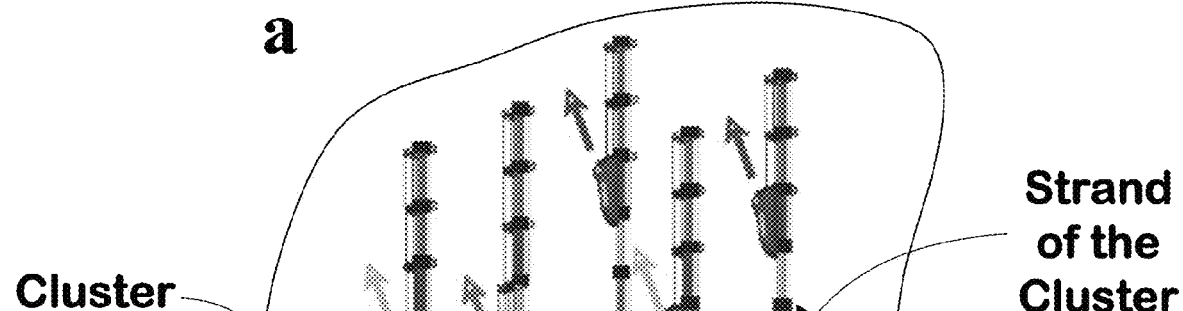
b
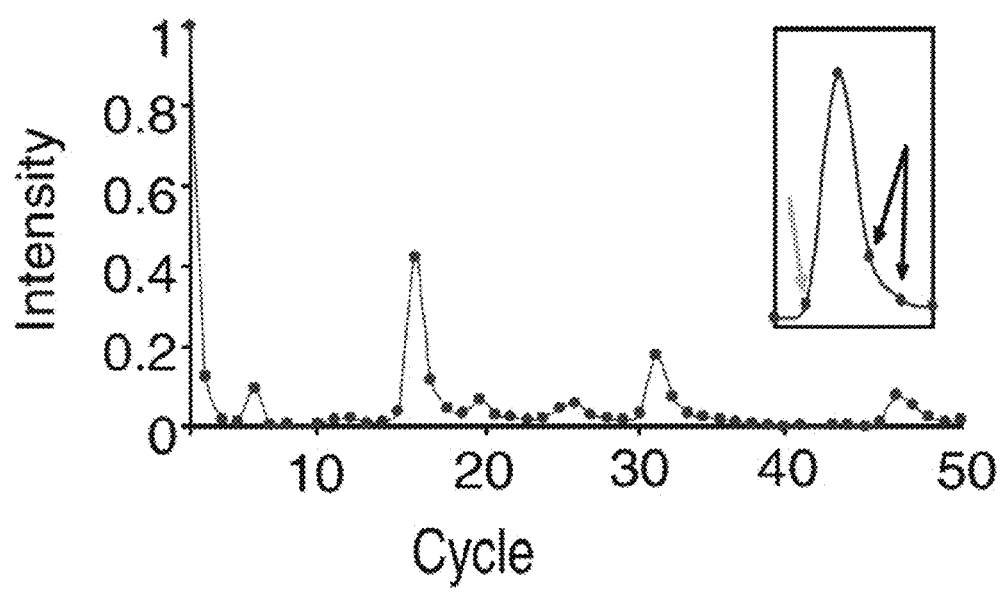
FIG. 30

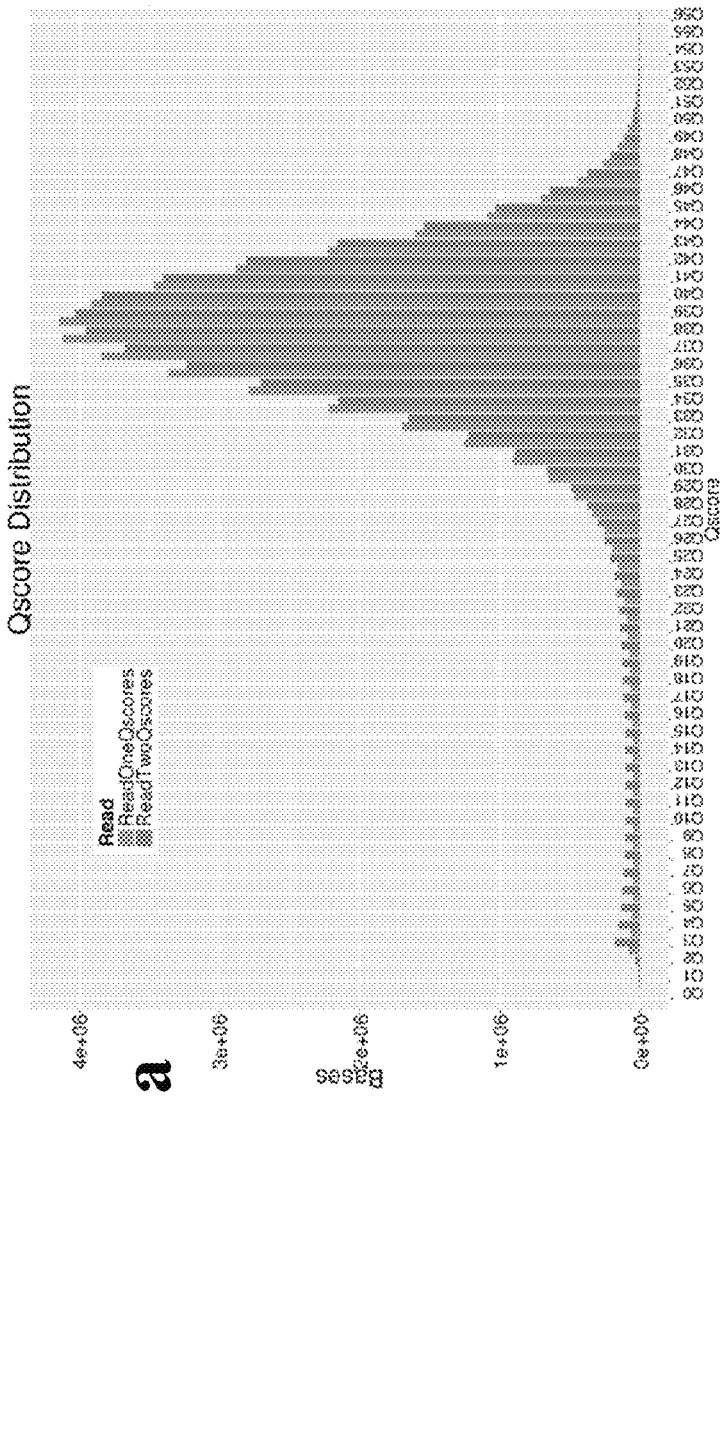
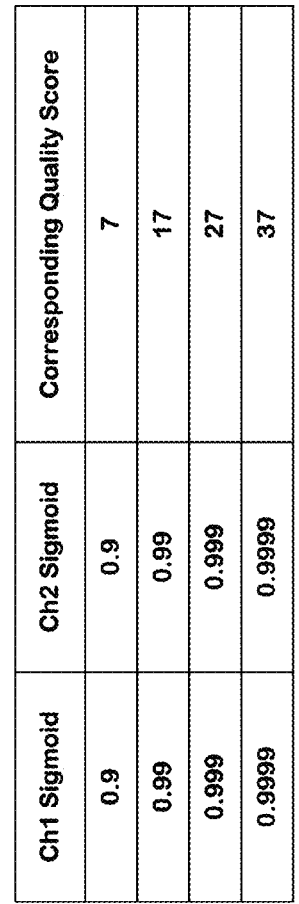
FIG. 34

BASE CALLING USING CONVOLUTIONS

PRIORITY APPLICATIONS

This application claims priority to or the benefit of U.S. Provisional Patent Application No. 62/849,091, titled, "Systems and Devices for Characterization and Performance Analysis of Pixel-Based Sequencing," filed May 16, 2019; U.S. Provisional Patent Application No. 62/849,132, titled, "Base Calling using Convolutions," filed May 16, 2019; and U.S. Provisional Patent Application No. 62/849,133, titled, "Base Calling using Compact Convolutions," filed May 16, 2019. The provisional applications are hereby incorporated by reference for all purposes.

This application claims priority to US Nonprovisional Patent Application No. 16/874,599, titled "Systems and Devices for Characterization and Performance Analysis of Pixel-Based Sequencing", filed contemporaneously. The Nonprovisional application is hereby incorporated by reference for all purposes.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

INCORPORATIONS

The following are incorporated by reference for all purposes as if fully set forth herein:

U.S. Provisional Patent Application No. 62/821,602, titled "TRAINING DATA GENERATION FOR ARTIFICIAL INTELLIGENCE-BASED SEQUENCING," filed on Mar. 21, 2019;

U.S. Provisional Patent Application No. 62/821,618, titled "TRAINING DATA GENERATION FOR ARTIFICIAL INTELLIGENCE-BASED SEQUENCING," filed on Mar. 21, 2019;

U.S. Provisional Patent Application No. 62/821,681, titled "ARTIFICIAL INTELLIGENCE-BASED BASE CALLING," filed on Mar. 21, 2019;

U.S. Provisional Patent Application No. 62/821,766, titled "ARTIFICIAL INTELLIGENCE-BASED SEQUENCING," filed on Mar. 21, 2019;

U.S. Provisional Patent Application No. 62/821,724, titled "ARTIFICIAL INTELLIGENCE-BASED QUALITY SCORING," filed on Mar. 21, 2019;

PCT Patent Application No. PCT/US2017/028883, titled "PHOTONIC STUCTURE-BASED DEVICES AND COMPOSITIONS FOR USE IN LUMINESCENT IMAGING OF MULTIPLE SITES WITHIN A PIXEL, AND METHODS OF USING THE SAME," filed on Apr. 21, 2017, subsequently published as PCT Publication No. WO 2017/184997 A1, published on Oct. 26, 2017;

PCT Patent Application No. PCT/US2016/047253, titled "IN-LINE PRESSURE ACCUMULATOR AND FLOW-CONTROL SYSTEM FOR BIOLOGICAL OR CHEMICAL ASSAYS," filed on Aug. 17, 2016, subsequently published as PCT Publication No. WO 2017/034868 A1, published on Mar. 2, 2017;

PCT Patent Application No. PCT/US2017/038259, titled "SUPER-RESOLUTION MICROSCOPY," filed on Jun. 20, 2017, subsequently published as PCT Publication No. WO 2017/223041 A1, published on Dec. 28, 2017;

U.S. patent application Ser. No. 15/077,182 titled "METHODS, CARRIER ASSEMBLIES, AND SYSTEMS FOR IMAGING SAMPLES FOR BIOLOGICAL OR CHEMICAL ANALYSIS," filed on Mar. 22, 2016, subsequently published as US 2016/0281150 A1 on Sep. 29, 2016;

U.S. Pat. No. 9,193,998 B2, titled "SUPER RESOLUTION IMAGING," issued on Nov. 24, 2015;

U.S. Pat. No. 9,937,497 B2 titled "MICRODEVICES AND BIOSENSOR CARTRIDGES FOR BIOLOGICAL OR CHEMICAL ANALYSIS AND SYSTEMS AND METHODS FOR THE SAME," issued on Apr. 10, 2018;

US Publication No. US 2017/0189904 A1, titled "SYSTEMIS AND METHODS FOR BOCHEMICAL ANALYSIS INCLUDING A BASE INSTRUMENT AND AREMOVABLE CARTRIDGE," published Jul. 6, 2017;

U.S. patent application Ser. No. 15/125,124, titled "DISPOSABLE, INTEGRATED MICROFLUIDIC CARTRIDGE AND METHODS OF MAKING AND USING SAME," filed Mar. 11, 2015, subsequently published as US 2017/0016060 A1 on Jan. 19, 2017;

European Patent Application No. 08781608.8, titled "METHOD AND APPARATUS USING ELECTRIC FIELD FOR IMPROVED BIOLOGICAL ASSAYS," EP Publication No. EP 2 173 467 B1, published May 4, 2016;

U.S. patent application Ser. No. 15/067,013, titled "INTEGRATED SEQUENCING APPARATUSES AND METHODS OF USE," filed Mar. 10, 2016, subsequently patented as U.S. Pat. No. 10,167,505 B2 and issued on Jan. 1, 2019; and U.S. patent application Ser. No. 13/882,088, titled "MICRODEVICES AND BIOSENSOR CARTRIDGES FOR BOLOGICAL OR CHEMICAL ANALYSIS AND SYSTEMS AND METHODS FOR THE SAME," filed Apr. 26, 2013, subsequently patented as U.S. Pat. No. 9,096,899 B2 and issued on Aug. 4, 2015.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Data used for base calling has known and unknown technical artifacts, biases, and error profiles. A significant challenge in base calling is to account for these imperfections in the assay data. Kinetic models used for base calling rely on substantial technical expertise and biochemistry intuition. To handle these biases, kinetic models use explicit programming for feature engineering and calculation of transition and correction matrices.

We propose a neural network-based base caller that automatically extract features from the assay data and learns to detect and account for these imperfections. An opportunity arises to use deep learning for increasing the level of accuracy and throughput in sequencing technologies.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 1 illustrates a cross-section of a biosensor in accordance with one implementation and also illustrates a top view of a detection device of the biosensor.

FIG. 2 illustrates, in one example, a cross-section of a portion of the detection device of FIG. 1 illustrating a portion of a reaction structure and a light guide thereof and also illustrates, in one example, an enlarged portion of the cross-section.

FIG. 18 shows phasing and prephasing data that specifies the probability distribution of polymerase population movement of FIG. 17 and is used as input for the compact convolution-based base calling in accordance with one implementation.

FIG. 19 illustrates base context data for three cycles that is used as input for the compact convolution-based base calling in accordance with one implementation.

FIG. 20 illustrates base context data for five cycles that is used as input for the compact convolution-based base calling in accordance with one implementation.

FIG. 30 illustrates one example of the phasing and prephasing effect.

FIG. 34 shows one example of quality score mapping produced by a quality score mapper.

DETAILED DESCRIPTION

Figure 3:
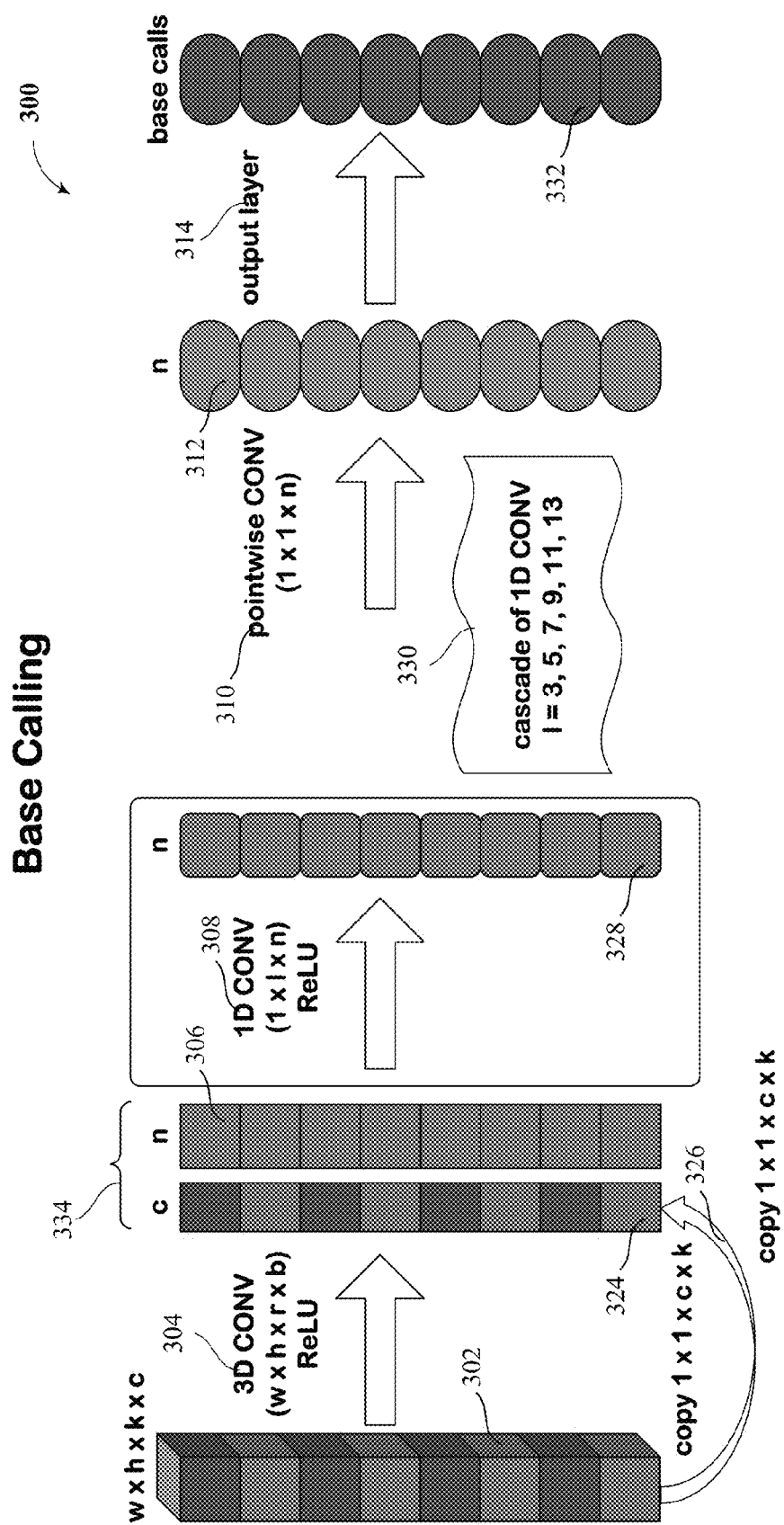
FIG. 3 depicts one implementation of base calling using convolutions.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

We propose a neural network-based base caller that detects and accounts for stationary, kinetic, and mechanistic properties of the sequencing process, mapping what is observed at each sequence cycle in the assay data to the underlying sequence of nucleotides. The neural network-based base caller combines the tasks of feature engineering, dimension reduction, discretization, and kinetic modelling into a single end-to-end learning framework. In particular, the neural network-based base caller uses a combination of 3D convolutions, 1D convolutions, and pointwise convolutions to detect and account for assay biases such as phasing and prephasing effect, spatial crosstalk, emission overlap, and fading.

Deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters.

Biosensor

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channel that delivers reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially alkaline/basic, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7.

In some examples, the reaction sites are provided or spaced apart in a predetermined manner, such as in a uniform or repeating pattern. In some other examples, the reaction sites are randomly distributed. Each of the reaction sites may be associated with one or more light guides and one or more light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, a designated reaction is a positive binding event, such as incorporation of a fluorescently labeled biomolecule with an analyte-of-interest, for example. More generally, a designated reaction may be a chemical transformation, chemical change, or chemical interaction. A designated reaction may also be a change in electrical properties. In particular examples, a designated reaction includes the incorporation of a fluorescently-labeled molecule with an analyte. The analyte may be an oligonucleotide and the fluorescently-labeled molecule may be a nucleotide. A designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore, or decrease fluorescence by co-locating a quencher and fluorophore.

As used herein, a "reaction solution," "reaction component" or "reactant" includes any substance that may be used to obtain at least one designated reaction. For example, potential reaction components include reagents, enzymes, samples, other biomolecules, and buffer solutions, for example. The reaction components may be delivered to a reaction site in a solution and/or immobilized at a reaction site. The reaction components may interact directly or indirectly with another substance, such as an analyte-of-interest immobilized at a reaction site. As noted above, the reaction solution may be substantially acidic (i.e., include a relatively high acidity) (e.g., comprising a pH of less than or equal to about 5, a pH less than or equal to about 4, or a pH less than or equal to about 3) or substantially alkaline/basic (i.e., include a relatively high alkalinity/basicity) (e.g., comprising a pH of greater than or equal to about 8, a pH of greater than or equal to about 9, or a pH of greater than or equal to about 10).

As used herein, the term "reaction site" is a localized region where at least one designated reaction may occur. A reaction site may include support surfaces of a reaction structure or substrate where a substance may be immobilized thereon. For example, a reaction site may include a surface of a reaction structure (which may be positioned in a channel of a flow cell) that has a reaction component thereon, such as a colony of nucleic acids thereon. In some such examples, the nucleic acids in the colony have the same sequence, being for example, clonal copies of a single stranded or double stranded template. However, in some examples a reaction site may contain only a single nucleic acid molecule, for example, in a single stranded or double stranded form.

A plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" or "reaction recess" includes a defined spatial region of the support structure (which is often in fluid communication with a flow channel). A reaction recess may be at least partially separated from the surrounding environment other or spatial regions. For example, a plurality of reaction recesses may be separated from each other by shared walls, such as a detection surface. As a more specific example, the reaction recesses may be nanowells comprising an indent, pit, well, groove, cavity or depression defined by interior surfaces of a detection surface and have an opening or aperture (i.e., be open-sided) so that the nanowells can be in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids or solutions that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include four types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

FIG. 1 illustrates a cross-section of a biosensor 100 in accordance with one implementation. As shown, the biosensor 100 may include a flow cell 102 that is coupled directly or indirectly to a light detection device 104. The flow cell 102 may be mounted to the light detection device 104. In the illustrated example, the flow cell 102 is affixed directly to the light detection device 104 through one or more securing mechanisms (e.g., adhesive, bond, fasteners, and the like). In some examples, the flow cell 102 may be removably coupled to the light detection device 104.

The biosensor 100 and/or detection device 104 may be configured for biological or chemical analysis to obtain any information or data that relates thereto. In particular examples, the biosensor 100 and/or detection device 104 may comprise a nucleic acid sequencing system (or sequencer) configured for various applications, including but not limited to de novo sequencing, resequencing of whole genomes or target genomic regions, and metagenomics. The sequencing system may be configured to perform DNA or RNA analysis. In some examples, the biosensor 100 and/or detection device 104 is configured to perform a large number of parallel reactions within the biosensor 100 and/or detection device 104 to obtain information relating thereto.

The flow cell 102 may include one or more flow channels that direct a solution to or toward reaction sites 114 on the detection device 104, as explained further below. The flow cell 102 and/or biosensor 100 may thereby include, or be in fluid communication with, a fluid/solution storage system (not shown) that may store various reaction components or reactants that are used to conduct the designated reactions therein, for example. The fluid storage system may also store fluids or solutions for washing or cleaning a fluid network and the biosensor 100 and/or detection device 104, and potentially for diluting the reactants. For example, the fluid storage system may include various reservoirs to store samples, reagents, enzymes, other biomolecules, buffer solutions, aqueous, oil and other non-polar solutions, and the like. As noted above, the fluid or solution provided on the reaction structure 126 may be relatively acidic (e.g., pH less than or equal to about 5) or basic/alkaline (e.g., pH greater than or equal to about 8). Furthermore, the fluid storage system may also include waste reservoirs for receiving waste products from the biosensor 100 and/or detection device 104.

In the illustrated example, the light detection device 104 includes a device base 125 and a reaction structure 126 overlying the device base 125. In particular examples, the device base 125 includes a plurality of stacked layers (e.g., silicon layer or wafer, dielectric layer, metal-dielectric layers, etc.). The device base 125 may include a sensor array 124 of light sensors 140, and a guide array of light guides 118. The reaction structure 126 may include an array of reaction recesses 108 that have at least one corresponding reaction site 114 provided therein (e.g., immobilized on a surface thereof). In certain examples, the light detection device 104 is configured such that each light sensor 140 corresponds (and potentially aligns) with a single light guide 118 and/or a single reaction recess 108 such that it receives photons only therefrom. However, in other examples, a single light sensor 140 may receive photons through more than one light guide 118 and/or from more than one reaction recess 108. A single light sensor 140 may thereby form one pixel or more than one pixel.

The array of reaction recesses 108 and/or light guides 118 (and potentially light sensors 140) may be provided in a defined repeating pattern such that at least some of the recesses 108 and/or light guides 118 (and potentially light sensors 140) are equally spaced from one another in a defined positional pattern. In other examples, the reaction recesses 108 and/or light guides 118 (and potentially light sensors 140) may be provided in a random pattern, and/or at least some of the reaction recesses 108 and/or light guides 118 (and potentially light sensors 140) may be variably spaced from each other.

As shown in FIGS. 1 and 2, the reaction structure 126 of the detection device 104 may define a detector surface 112 over which a reaction solution may flow and reside, as explained further below. The detector surface 112 of the reaction structure 126 may be the top exposed surface of the detection device 104. The detector surface 112 may comprise the surfaces of the recesses 108 and interstitial areas 113 extending between and about the recesses 108.

The detector surface 112 of the light detection device 104 may be functionalized (e.g., chemically or physically modified in a suitable manner for conducting designated reactions). For example, the detector surface 112 may be functionalized and may include a plurality of reaction sites 114 having one or more biomolecules immobilized thereto. As noted above, the detector surface 112 may include an array of reaction recesses 108 (e.g., open-sided reaction chambers). Each of the reaction recesses 108 may include one or more of the reaction site 114. The reaction recesses 108 may be defined by, for example, a change in depth (or thickness) along the detector surface 112. In other examples, the detector surface 112 may be substantially planar.

The reaction sites 114 may be distributed in a pattern along the detector surface 112, such as within the reaction recesses 108. For instance, the reactions sites 114 may be located in rows and columns along the reaction recesses 108 in a manner that is similar to a microarray. However, it is understood that various patterns of reaction sites 114 may be used. The reaction sites 114 may include biological or chemical substances that emit light signals, as explained further below. For example, the biological or chemical substances of the reactions sites 114 may generate light emissions in response to the excitation light 101. In particular examples, the reaction sites 114 include clusters or colonies of biomolecules (e.g., oligonucleotides) that are immobilized on the detector surface 112 within the reaction recesses 108. The reactions sites 114 may generate light emissions in response to incident excitation light after treatment with the reaction solution. For example, the reaction solution may initiate a reaction and/or form a reaction product at the reactions sites 114 (but potentially not at other reaction sites of the reaction structure 126 of the device 104) that generates light emissions in response to the excitation light.

The excitation light 101 may be emitted from any illumination source (not shown), which may or may not be part of the bioassay system, biosensor 100 or light detection device 104. In some examples, the illumination system may include a light source (e.g., one or more LED) and, potentially, a plurality of optical components to illuminate at least the reaction structure 126 of the detection device 104. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In a particular example, the illumination system is configured to direct the excitation light 101 to reaction sites 114 within the recesses 108 of the reaction structure 126 of the detection device 104. In some examples, the illumination system may emit the excitation light 101 within a range of wavelengths, such as within the range of about 300 nm to about 700 nm for example, or more particularly within the range of about 400 nm to about 600 nm for example. In some examples, the illumination system may emit the excitation light 101 at a certain wavelength or wavelengths that excites the biological or chemical substance(s) of the reaction sites 108 (e.g., a reaction initiated by the reaction solution and/or reaction product form by the reaction solution at the reactions sites 114) to emit light emissions of a differing wavelength or wavelengths. For example, in one example where the reaction sites 108 include fluorophores excited by green wavelengths of light, the excitation light may be about 532 nm and the light emissions may be about 570 nm or more.

Detection Device

FIG. 2 shows the detection device 104 in greater detail than FIG. 1. More specifically, FIG. 2 shows a single light sensor 140, a single light guide 118 for directing and passing light emissions from at least one reaction site 114 associated therewith toward the light sensor 140, and associated circuitry 146 for transmitting signals based on the light emissions (e.g., photons) detected by the light sensor 140. It is understood that the other light sensors 140 of the sensor array 124 and associated components may be configured in an identical or similar manner. It is also understood, however, the light detection device 104 is not required to be manufactured uniformly throughout. Instead, one or more light sensors 140 and/or associated components may be manufactured differently or have different relationships with respect to one another.

The circuitry 146 may include interconnected conductive elements (e.g., conductors, traces, vias, interconnects, etc.) that are capable of conducting electrical current, such as the transmission of data signals that are based on detected photons. For example, in some examples, the circuitry 146 may comprise a microcircuit arrangement. The light detection device 104 and/or the device base 125 may comprise at least one integrated circuit having an array of the light sensors 140. The circuitry 146 positioned within the detection device 104 may be configured for at least one of signal amplification, digitization, storage, and processing. The circuitry 146 may collect (and potentially analyze) the detected light emissions and generate data signals for communicating detection data to a bioassay system. The circuitry 146 may also perform additional analog and/or digital signal processing in the light detection device 104.

The device base 125 and the circuitry 146 may be manufactured using integrated circuit manufacturing processes, such as processes used to manufacture charged-coupled devices or circuits (CCD) or complementary-metal-oxide semiconductor (CMOS) devices or circuits. For example, as shown in FIG. 2, the device base 125 may be a CMOS device comprising of a plurality of stacked layers including a sensor base 141, which may be a silicon layer (e.g., a wafer) in some examples. The sensor base 141 may include the light sensor 140, and gates 143 formed thereon. The gates 143 may be electrically coupled to the light sensor 140. When the light detection device 104 is configured as shown in FIG. 2, the light sensor 140 may be electrically coupled to the circuitry 146 through the gates 143, for example.

Convolution-Based Base Calling

FIG. 3 depicts one implementation of base calling 300 using convolutions. The base calling 300 is operationalized by the neural network-based base caller 2614. That is, the three-dimensional (3D) convolution filters 304, the skip connection 326, the one-dimensional (1D) convolution filters 308, the pointwise convolution filters 310, and the output layer 314 are components of the neural network-based base caller 2614, which processes the input data 2632 through its components and produces the base calls 332 as output. The convolution operations of the neural network-based base caller 2614 are operationalized by a convolution operator 2615, which is also a component of the neural network-based base caller 2614. The convolution operator 2615 in turn comprises a 3D convolution operator 2616, a 1D convolution operator 2617, a pointwise convolution operator 2618, and a transposed convolution operator 2619.

In one implementation, the input data 2632 is image data 302 based on intensity signals depicting analyte emissions (e.g., in the case of Illumina). The image data 302 is derived from sequencing images produced by a sequencer during a sequencing run. In one implementation, the image data 302 comprises w×h image patches extracted from the sequencing images, where w (width) and h (height) are any numbers ranging from 1 and 10,000 (e.g., 3×3, 5×5, 7×7, 10×10, 15×15, 25×25). In some implementations, w and h are the same. In other implementations, w and h are different.

The sequencing run produces c image(s) per sequencing cycle for corresponding c imaged channels, and an image patch is extracted by an input preparer 2625 from each of the c image(s) to prepare the image data for a particular sequencing cycle. In different implementations such as 4-, 2-, and 1-channel chemistries, c is 4 or 2. In other implementations, c is 1, 3, or greater than 4. The image data 302 is in the optical, pixel domain in some implementations, and in the upsampled, subpixel domain in other implementations.

The image data 302 comprises data for multiple sequencing cycles (e.g., a current sequencing cycle, one or more preceding sequencing cycles, and one or more successive sequencing cycles). In one implementation, the image data 302 comprises data for three sequencing cycles, such that data for a current (time t) sequencing cycle to be base called is accompanied with (i) data for a left flanking/context/previous/preceding/prior (time t−1) sequencing cycle and (ii) data for a right flanking/context/next/successive/subsequent (time t+1) sequencing cycle. In other implementations, the image data 302 comprises data for a single sequencing cycle. In yet other implementations, the image data 302 comprises data for 58, 75, 92, 130, 168, 175, 209, 225, 230, 275, 318, 325, 330, 525, or 625 sequencing cycles.

The image data 302 depicts intensity emissions of one or more clusters and their surrounding background. In one implementation, when a single target cluster is to be base called, the image patches are extracted from the sequencing images by the input preparer 2625 in such a way that each image patch contains intensity signal data from the target cluster in its center pixel.

The image data 302 is encoded in the input data 2632 using intensity channels (also called imaged channels). For each of the c images obtained from the sequencer for a particular sequencing cycle, a separate imaged channel is used to encode its intensity signal data. Consider, for example, that the sequencing run uses the 2-channel chemistry which produces a red image and a green image at each sequencing cycle. In such a case, the input data 2632 comprises (i) a first red imaged channel with w×h pixels that depict intensity emissions of the one or more clusters and their surrounding background captured in the red image and (ii) a second green imaged channel with w×h pixels that depict intensity emissions of the one or more clusters and their surrounding background captured in the green image.

In another implementation, the input data 2632 is based on pH changes induced by the release of hydrogen ions during molecule extension. The pH changes are detected and converted to a voltage change that is proportional to the number of bases incorporated (e.g., in the case of Ion Torrent).

In yet another implementation, the input data 2632 is constructed from nanopore sensing that uses biosensors to measure the disruption in current as an analyte passes through a nanopore or near its aperture while determining the identity of the base. For example, the Oxford Nanopore Technologies (ONT) sequencing is based on the following concept: pass a single strand of DNA (or RNA) through a membrane via a nanopore and apply a voltage difference across the membrane. The nucleotides present in the pore will affect the pore's electrical resistance, so current measurements over time can indicate the sequence of DNA bases passing through the pore. This electrical current signal (the 'squiggle' due to its appearance when plotted) is the raw data gathered by an ONT sequencer. These measurements are stored as 16-bit integer data acquisition (DAC) values, taken at 4 kHz frequency (for example). With a DNA strand velocity of ~450 base pairs per second, this gives approximately nine raw observations per base on average. This signal is then processed to identify breaks in the open pore signal corresponding to individual reads. These stretches of raw signal are base called—the process of converting DAC values into a sequence of DNA bases. In some implementations, the input data 2632 comprises normalized or scaled DAC values.

The dimensionality of the image data 302 can be expressed as w×h×k×c, where "w" represents the width of the image data 302, "h" represents the height of the image data 302, "k" represents the number of sequencing cycles for which the image data 302 is obtained, and "c" represents the number of imaged channels in the image data 302. In one implementation, w can be 3, 5, 6, 10, 15, or 25 and h can be the same as w. In one implementation, k can be 1, 3, 5, 7, 9, 11, 13, 15, 17, 19, 21, 23, 25, 58, 75, 92, 130, 168, 175, 209, 225, 230, 275, 318, 325, 330, 525, or 625. In one implementation, c can be 1, 2, 3, 4, 6, or 10.

The 3D convolution filters 304 apply 3D convolutions (3D CONV) on the image data 302 and produce output features 306. The dimensionality of the 3D convolutions can be expressed as w×h×r×n, where "w" represents the width of a 3D convolution kernel, "h" represents the height of the 3D convolution kernel, "r" represents the receptive field of the 3D convolution kernel, and "n" represents a total number of the 3D convolution filters 304. In one implementation, w can be 3, 5, 6, 10, 15, or 25 and h can be the same as w. In one implementation, r can be 3, 5, 7, 10, 15, or 25. In one implementation, n can be 3, 5, 10, 50, 100, 150, 198, 200, 250, or 300. The 3D convolutions are operationalized by the 3D convolution operator 2616.

Figure 27:
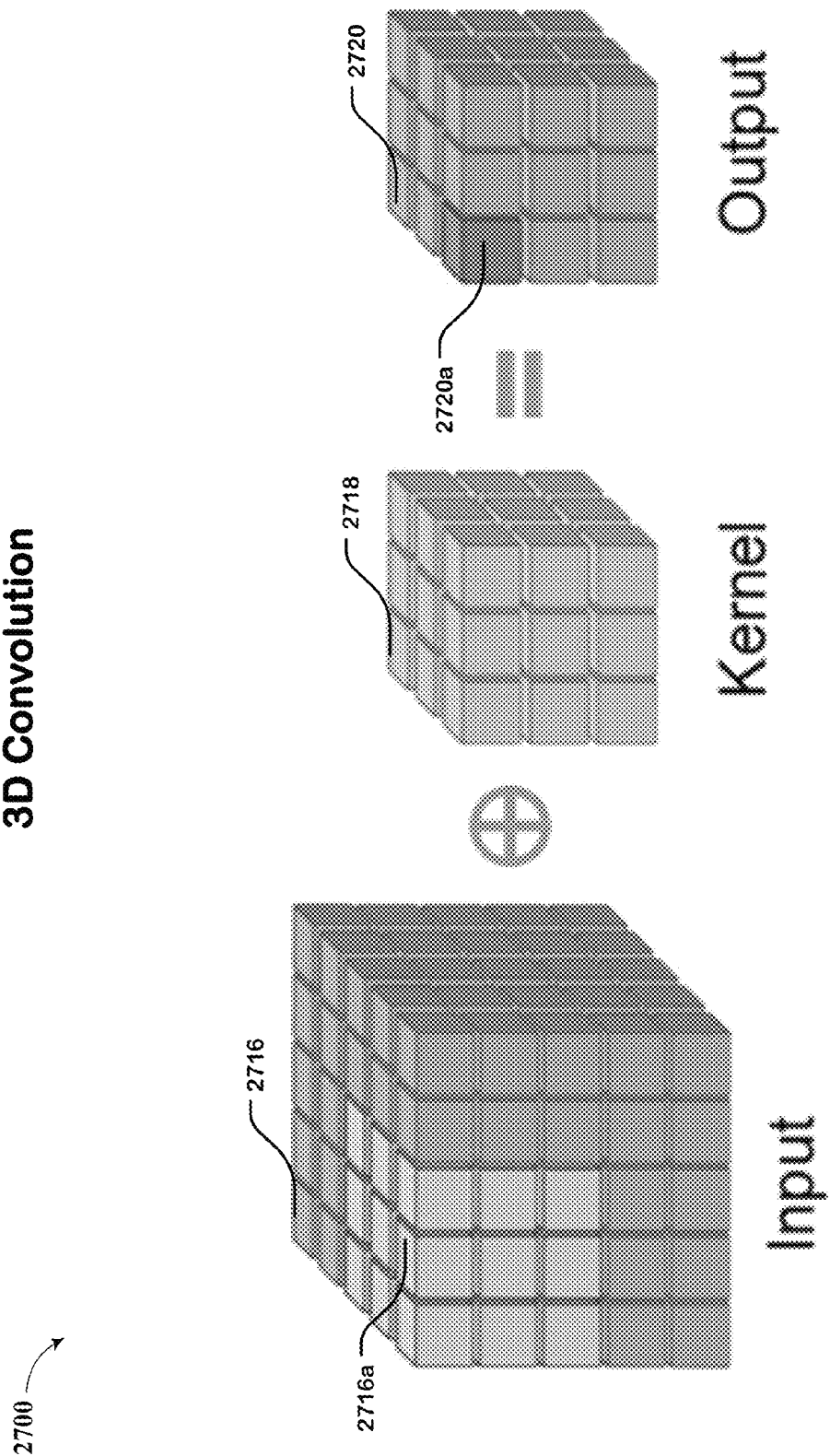
FIG. 27 illustrates one implementation of a 3D convolution used in the convolution-based base calling.

FIG. 27 illustrates one implementation of a 3D convolution 2700 used in the convolution-based base calling 300. A 3D convolution is a mathematical operation where each voxel present in the input volume is multiplied by a voxel in the equivalent position of the convolution kernel. At the end, the sum of the results is added to the output volume. In FIG. 27, it is possible to observe the representation of the 3D convolution, where the voxels 2716a highlighted in the input 2716 are multiplied with their respective voxels in the kernel 2718. After these calculations, their sum 2720a is added to the output 2720.

Since the coordinates of the input volume are given by (x, y, z) and the convolution kernel has size (P, Q, R), the 3D convolution operation can be mathematically defined as:

$$O_{xyz} = \sum_{p=0}^{P-1} \sum_{q=0}^{Q-1} \sum_{r=0}^{R-1} K_{pqr} I_{(x+p)(y+q)(z+r)},$$

where
O is the result of the convolution,
I is the input volume,
K is the convolution kernel, and
(p, q, r) are the coordinates of K.

The bias term is omitted from the above equation to improve clarity.

Thus, 3D convolutions, in addition to extracting spatial information from matrices like 2D convolutions, extract information present between consecutive matrices. This allows them to map both spatial information of 3D data and temporal information of a set of sequential images.

In some implementations, the output features 306 are subjected to nonlinear activation functions such as rectifying linear unit (ReLU), leaky ReLU, exponential linear unit (ELU), parametric ReLU (PReLU), sigmoid, and hyperbolic tangent (tanh) to produce activated output features. The nonlinear activation functions are operationalized by a nonlinear activation function applier 504, which is also a component of the neural network-based base caller 2614. In some implementations, batch normalization is applied either before or after the 3D convolutions. The batch normalization is operationalized by a batch normalizer 2622, which is also a component of the neural network-based base caller 2614.

In some implementations, a skip connection 326 combines parts 324 of the image data 302 (or the input data 2632) with the output features 306 (or the activated output features). In other implementations, the skip connection 326 combines all of the image data 302 (or the input data 2632) with the output features 306 (or the activated output features). The combining can be accomplished by concatenation or summation. The resulting combined data is referred to as supplemented features 334. In one implementation, when a single target cluster is to be base called, information about the single target cluster is selected from the image data 302 (or the input data 2632) and combined with the output features 306 (or the activated output features). In some implementations, from the image data 302, intensity signal data depicted by a pixel (1×1) associated with the single target cluster is selected for each of the imaged channels (c) and for each of the sequencing cycles (k) and combined with the output features 306 (or the activated output features). The skip connection 326 is operationalized by a skip connector 2620, which is also a component of the neural network-based base caller 2614.

The 1D convolution filters 308 apply 1D convolutions (1D CONV) on the supplemented features 334 and produce further output features 328. In one implementation, a cascade of the 1D convolutions 330 is applied. That is, a first 1D convolution in the cascade 330 processes the supplemented features 334 as starting input and produces a first set of the further output features 328. A second 1D convolution in the cascade 330 then processes the first set of the further output features 328 and produces a second set of the further output features 328. A third 1D convolution in the cascade 330 then processes the second set of the further output features 328 and produces a third set of the further output features 328. An ultimate 1D convolution in the cascade 330 processes the penultimate set of the further output features 328 and produces an ultimate set of the further output features 328, which is then fed as starting input to the pointwise convolutions (pointwise CONV).

In yet other implementations, instead of the cascade, just one 1D convolution is applied.

Each 1D convolution in the cascade 330 uses a bank (n) of the 1D convolution filters 308. In some implementations, each 1D convolution in the cascade 330 has a different kernel width or receptive field (l). For example, l can be 3, 5, 7, 9, 11, and 13. In other implementations, some 1D convolutions in the cascade 330 have the same 1, while other 1D convolutions in the cascade 330 have a different l. In the cascade 330, as the 1D convolutions are applied, l can be progressively increased, progressively decreased, randomly varied, or randomly maintained. The 1D convolutions are operationalized by the 1D convolution operator 2617.

Figure 28:
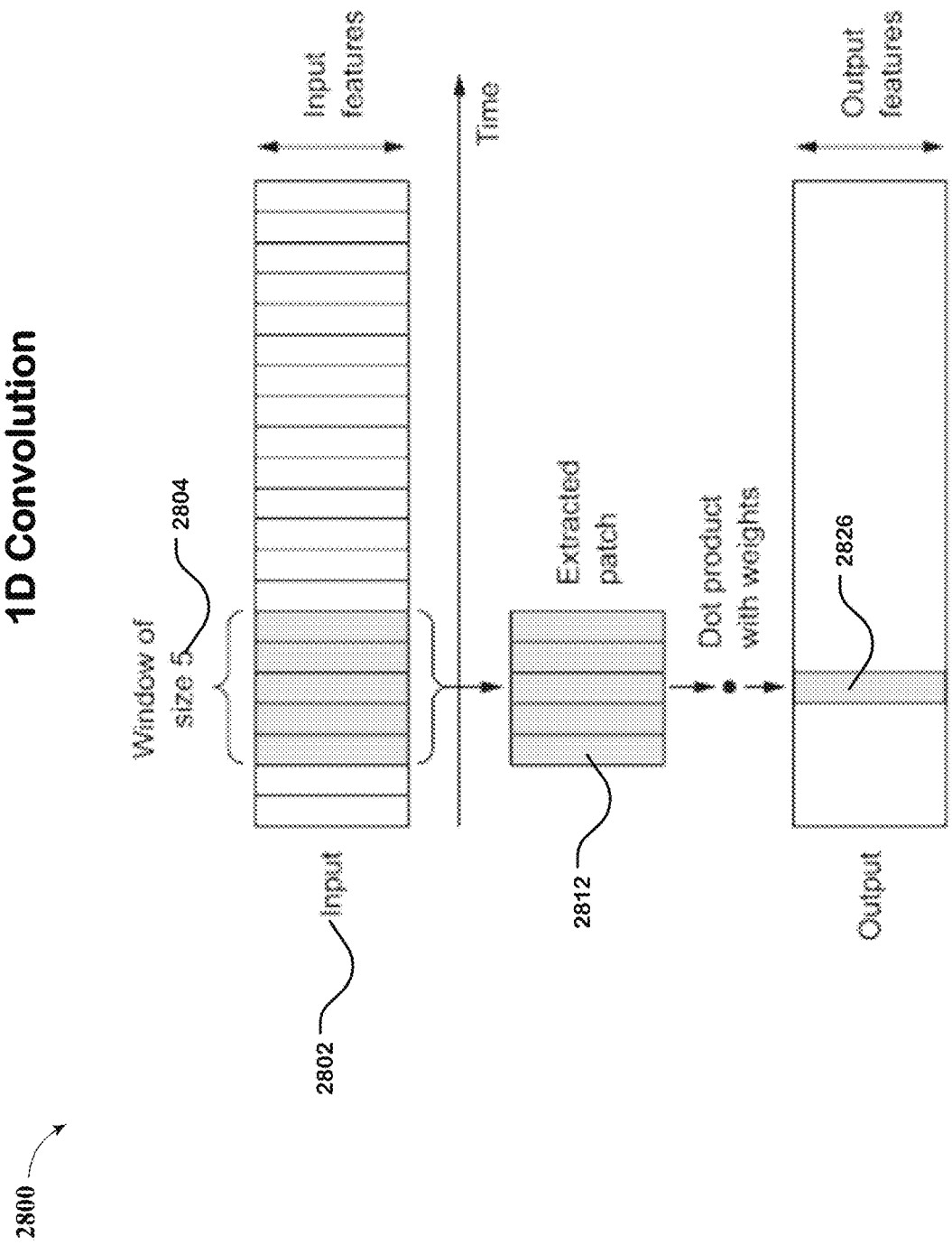
FIG. 28 illustrates one implementation of a 1D convolution used in the convolution-based base calling.

FIG. 28 illustrates one implementation of a 1D convolution 2800 used in the convolution-based base calling 300. A 1D convolution extracts local 1D patches 2812 or subsequences from an input sequence 2802 and obtains an output 2826 from each such 1D patch 2812. The 1D convolution recognizes local patters in the input sequence 2802. Because the same input transformation is performed on every patch 2812, a pattern learned at a certain position in the input sequence 2802 can be later recognized at a different position, making the 1D convolution invariant to temporal translations. For instance, when the 1D convolution processes the input sequence 2802 using convolution windows of size five 2804, it learns sequence patterns of length five or less, and thus recognizes base motifs in the input sequence 2802. This way the 1D convolution is able to learn the underlying base morphology.

In some implementations, the further output features 328 are subjected to nonlinear activation functions such as rectifying linear unit (ReLU), leaky ReLU, exponential linear unit (ELU), parametric ReLU (PReLU), sigmoid, and hyperbolic tangent (tanh) to produce activated further output features. In some implementations, batch normalization is applied either before or after each 1D convolution in the cascade.

Figure 29:
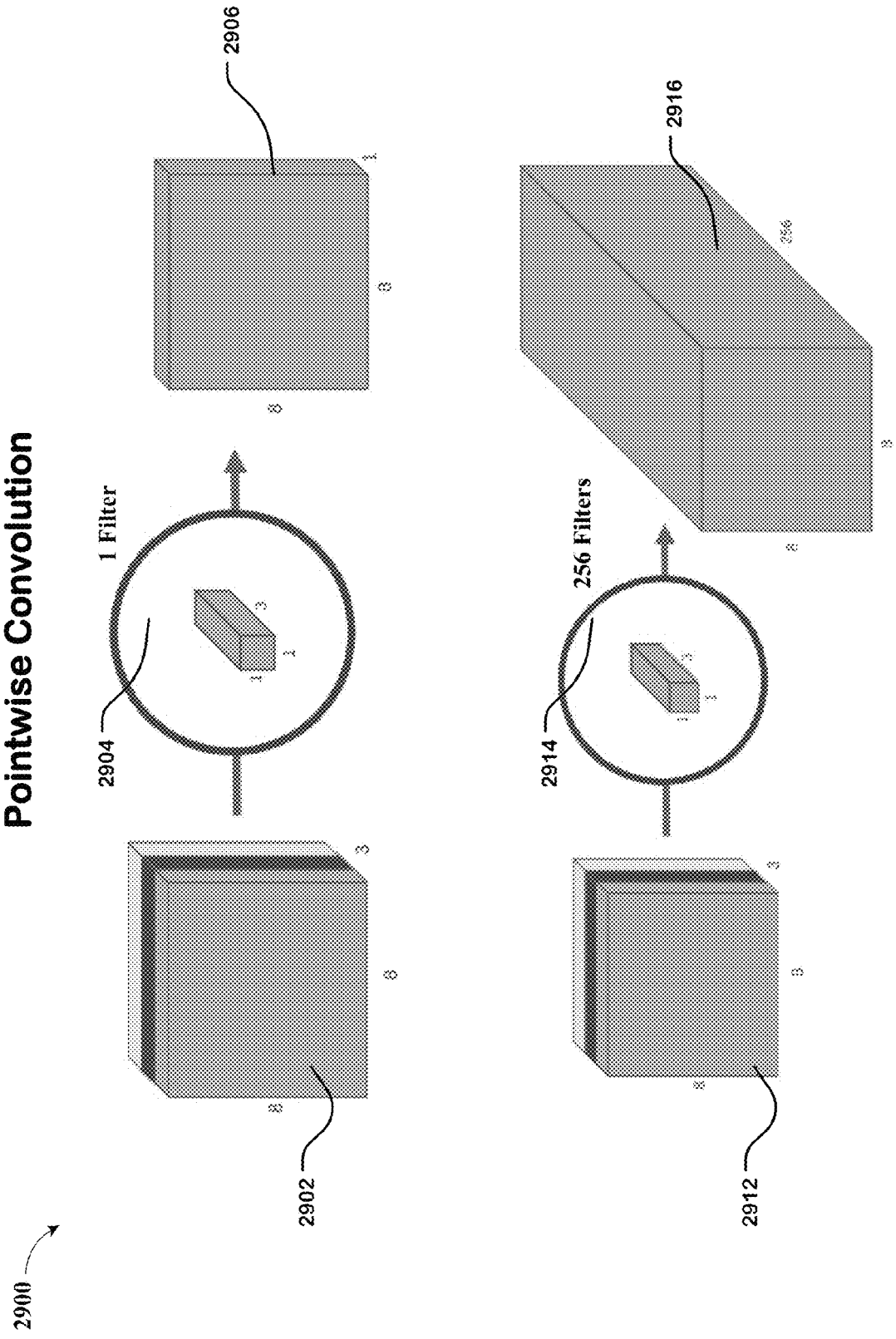
FIG. 29 illustrates one implementation of a pointwise convolution used in the convolution-based base calling.

The pointwise convolution filters 310 apply pointwise convolutions (pointwise CONV) on the ultimate set of the further output features 328 (or activated further output features) and produce final output features 312. The pointwise convolutions are operationalized by the pointwise convolution operator 2618. FIG. 29 illustrates one implementation of a pointwise convolution 2900 used in the convolution-based base calling 300. A pointwise convolution is a convolution with a 1×1 receptive field/kernel width/window/spatial dimensions. When a pointwise convolution having a bank of n filters is applied on an input with n channels, the resulting output has b channels. However, the output that has the same spatial dimensionality as the input, i.e., the pointwise convolution carries the spatial dimensionality of the input onto the output. In FIG. 29, when an input 2902 is convolved over by a single pointwise convolution filter 2904, the resulting output 2906 has only one channel. Similarly, when another input 2912 is convolved over by a bank of 256 pointwise convolution filters 2914, the resulting output 2916 has 256 channels. Note that, in both the examples, the output spatial dimensionality matches the input spatial dimensionality, i.e., 8×8.

In some implementations, the final output features 312 are subjected to nonlinear activation functions such as rectifying linear unit (ReLU), leaky ReLU, exponential linear unit (ELU), parametric ReLU (PReLU), sigmoid, and hyperbolic tangent (tanh) to produce activated final output features. In some implementations, batch normalization is applied either before or after the pointwise convolutions.

The output layer 314 processes the final output features 312 and produces base calls 332. The output layer 314 can comprise a fully-connected network 2348, a sigmoid layer, a softmax layer, and/or a regression layer.

In one implementation, the neural network-based base caller 2614 uses 3D convolutions that mix information between the input channels and 1D convolutions that also mix information between the input channels. In another implementation, the neural network-based base caller 2614 uses 3D convolutions that mix information between the input channels, but 1D convolutions that do not mix information between the input channels. In yet another implementation, the neural network-based base caller 2614 uses 3D convolutions that do not mix information between the input channels, but 1D convolutions that mix information between the input channels. In yet further implementation, the neural network-based base caller 2614 uses 3D convolutions that do not mix information between the input channels and 1D convolutions that also do not mix information between the input channels.

The 3D convolutions, the 1D convolutions, the pointwise convolutions, and the transposed convolutions can use padding. In one implementation, the padding is SAME or zero padding and produces at least one feature element corresponding to each sequencing cycle. In another implementation, the padding is VALID padding. Also, the intermediate calculations of the neural network-based base caller 2614 are stored as intermediate features 2605.

3D Convolutions

Figure 4:
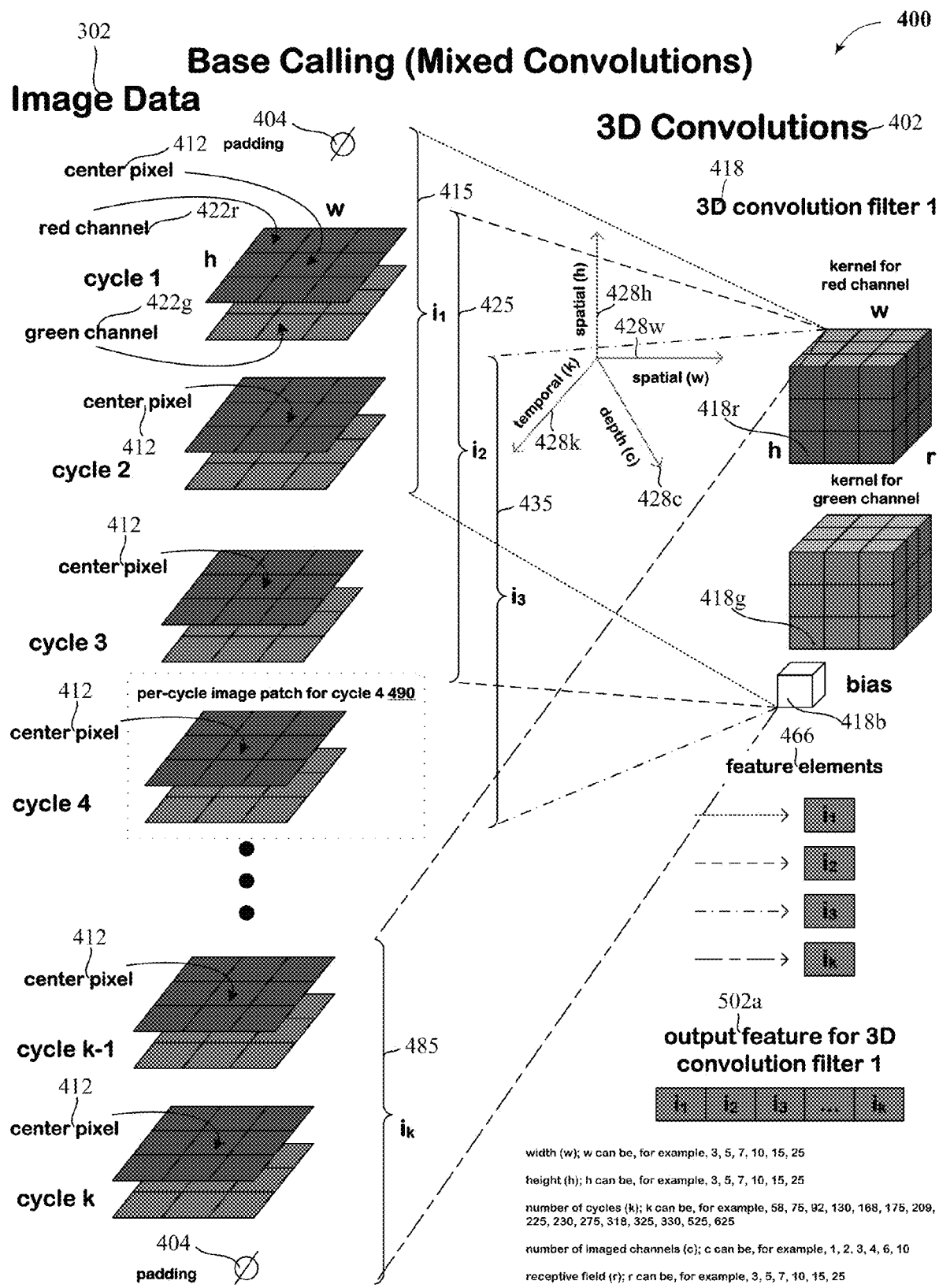
FIG. 4 depicts three-dimensional (3D) convolutions used in the convolution-based base calling in accordance with one implementation that mixes information between the imaged channels.

FIG. 4 depicts 3D convolutions 402 used in the convolution-based base calling 400 in accordance with one implementation that mixes information between the imaged channels. The 3D convolutions 402 convolve over the image data 302. We first describe how the image data 302 includes pixels that contain intensity data for associated analytes and how the intensity data is obtained for one or more imaged channels by corresponding light sensors configured to detect emissions from the associated analytes.

Image Data

The biosensor 100 comprises an array of light sensors. A light sensor is configured to sense information from a corresponding pixel area (e.g., a reaction site/well/nanowell) on the detection surface of the biosensor 100. An analyte disposed in a pixel area is said to be associated with the pixel area, i.e., the associated analyte. At a sequencing cycle, the light sensor corresponding to the pixel area is configured to detect/capture/sense emissions/photons from the associated analyte and, in response, generate a pixel signal for each imaged channel. In one implementation, each imaged channel corresponds to one of a plurality of filter wavelength bands. In another implementation, each imaged channel corresponds to one of a plurality of imaging events at a sequencing cycle. In yet another implementation, each imaged channel corresponds to a combination of illumination with a specific laser and imaging through a specific optical filter.

Pixel signals from the light sensors are communicated to a signal processor coupled to the biosensor 100 (e.g., via a communication port). For each sequencing cycle and each imaged channel, the signal processor produces an image whose pixels respectively depict/contain/denote/represent/characterize pixel signals obtained from the corresponding light sensors. This way, a pixel in the image corresponds to: (i) a light sensor of the biosensor 100 that generated the pixel signal depicted by the pixel, (ii) an associated analyte whose emissions were detected by the corresponding light sensor and converted into the pixel signal, and (iii) a pixel area on the detection surface of the biosensor 100 that holds the associated analyte.

Consider, for example, that a sequencing run uses two different imaged channels: a red channel and a green channel. Then, at each sequencing cycle, the signal processor produces a red image and a green image. This way, for a series of k sequencing cycles of the sequencing run, a sequence with k pairs of red and green images is produced as output.

Pixels in the red and green images (i.e., different imaged channels) have one-to-one correspondence within a sequencing cycle. This means that corresponding pixels in a pair of the red and green images depict intensity data for the same associated analyte, albeit in different imaged channels. Similarly, pixels across the pairs of red and green images have one-to-one correspondence between the sequencing cycles. This means that corresponding pixels in different pairs of the red and green images depict intensity data for the same associated analyte, albeit for different acquisition events/timesteps (sequencing cycles) of the sequencing run.

Corresponding pixels in the red and green images (i.e., different imaged channels) can be considered a pixel of a "per-cycle image" that expresses intensity data in a first red channel and a second green channel. A per-cycle image whose pixels depict pixel signals for a subset of the pixel areas, i.e., a region (tile) of the detection surface of the biosensor 100, is called a "per-cycle tile image." A patch extracted from a per-cycle tile image is called a "per-cycle image patch." In one implementation, the patch extraction is performed by the input preparer 2625.

The image data 302 comprises a sequence of per-cycle image patches generated for a series of k sequencing cycles of a sequencing run. The pixels in the per-cycle image patches contain intensity data for associated analytes and the intensity data is obtained for one or more imaged channels (e.g., a red channel 422r and a green channel 422g) by corresponding light sensors configured to detect emissions from the associated analytes. In one implementation, when a single target cluster is to be base called, the per-cycle image patches are centered at a center pixel 412 that contains intensity data for a target associated analyte and non-center pixels in the per-cycle image patches contain intensity data for associated analytes adjacent to the target associated analyte. In one implementation, the image data 302 is prepared by the input preparer 2625.

As an example, a per-cycle image patch for cycle 4 is referenced in FIG. 4 by numerical 490. Also note that, in FIG. 4, the repeated reference to the center pixel 412 across the k per-cycle image patches illustrates the pixel-to-pixel correspondence discussed above. The image data 302 is padded with padding 404. In one implementation, the padding 404 is SAME or zero padding and produces at least one feature element corresponding to each of the k sequencing cycles. In another implementation, the padding 404 is VALID padding.

Convolution Window

The 3D convolutions 402 are applied on the image data 302 on a sliding convolution window basis. FIG. 4 shows four convolution windows 415, 425, 435, and 485. A convolution window covers a plurality of the per-cycle image patches (e.g., anywhere between 2 to 200 per-cycle image patches forming the plurality) and produces a feature element as output. In FIG. 4, feature elements 466 corresponding to the convolution windows 415, 425, 435, and 485 of a first 3D convolution filter 418 are i1, i2, i3, and ik. The feature elements 466 are arranged in an output feature 502*a*.

Convolution Kernels

The 3D convolutions 402 use imaged channel-specific convolution kernels such that a convolution kernel convolves over data for its own imaged channel and does not convolve over data for another imaged channel. For example, in FIG. 4, the red convolution kernel 418*r* convolves over the data in the red channel 422*r* and the green convolution kernel 418*g* convolves over the data in the green channel 422*g* (along with bias 418*b*). The output of a convolution kernel convolving over the plurality of the per-cycle image patches is an intermediate feature element (not shown). A feature element like i1, i2, i3, or ik is a result of accumulating (summing) respective intermediate feature elements produced by all the convolution kernels of a 3D convolutions filter.

For example, the feature element i1 produced by the first 3D convolution filter 418 for the convolution window 415 is made up of a red intermediate feature element i1*r* (not shown) produced by the red convolution kernel 418*r* and a green intermediate feature element i1*g* (not shown) produced by the green convolution kernel 418*g*. In FIG. 4, the red and green intermediate feature elements are combined or mixed to produce the feature elements 466. This is referred to herein as "channel mixing" or "mixed convolutions."

When the respective outputs of convolution kernels of a convolution filter are not combined and instead maintained as separate channels for downstream processing, such an implementation is referred to herein as "channel segregation" or "segregated convolutions." As discussed above, depending on the implementation, the neural network-based base caller 2614 can use (i) mixed 3D and 1D convolutions, (ii) mixed 3D convolutions but segregated 1D convolutions, (iii) segregated 3D convolutions but mixed 1D convolutions, and/or (iv) segregated 3D and 1D convolutions.

Biases in the Image Data

The image data 302 is subject to biases such as phasing and prephasing effect, spatial crosstalk, emission overlap, and fading.

Phasing and Prephasing Effect

In the ideal situation, the lengths of all nascent strands within an analyte would be the same. Imperfections in the cyclic reversible termination (CRT) chemistry create stochastic failures that result in nascent strand length heterogeneity, introducing lagging (too short) and leading (too long) nascent strands within the analyte and reduces the purity of signal output from the interrogated position by contamination with signals from adjacent nucleotides. Phasing and prephasing effect refers to contamination of the signal for a specific cycle by the signal of the cycles before and after. Phasing and pre-phasing leads to the loss of synchrony in the readout of the sequence copies of an analyte.

Phasing is caused by incomplete removal of the 3' terminators and fluorophores as well as sequences in the analyte missing an incorporation cycle. Prephasing is caused by the incorporation of nucleotides without effective 3'-blocking. Phasing and prephasing effect is a nonstationary distortion and thus the proportion of sequences in each analyte that are affected by phasing and prephasing increases with cycle number; hampering correct base identification and limiting the length of useful sequence reads.

Incomplete extension due to phasing results in lagging strands (e.g., t-1 from the current cycle). Addition of multiple nucleotides or probes in a population of identical strands due to prephasing results in leading strands (e.g., t+1 from the current cycle). Other terms used to refer to phasing and phasing include falling behind, moved ahead, lagging, leading, dephasing, post-phasing, out-of-phase, out-of-sync, out-of-step nucleotide synthesis, asynchronicity, carry-forward (CF), incomplete or premature extension (IE), and droop (DR).

FIG. 30 illustrates one example of the phasing and prephasing effect 3000. FIG. 30*a* shows that some strands of an analyte lead (red) while others lag behind (blue), leading to a mixed signal readout of the analyte. FIG. 30*b* depicts the intensity output of analyte fragments with "C" impulses every 15 cycles in a heterogeneous background. Notice the anticipatory signals (gray arrow) and memory signals (black arrows) due to the phasing and prephasing effect 3000.

Spatial Crosstalk

Spatial crosstalk refers to a signal or light emission from one or more non-associated analytes (or pixel areas) that is detected by a corresponding light detector of an associated analyte (or pixel area). Spatial crosstalk is caused by unwanted emissions from adjacent analytes. Ideally, the intensities of each analyte should correspond to just one analyte sequence. However, the observed intensities often contain signals from neighboring analyte sequences, other than the interrogated/target one, and, hence, are not pure.

Figure 31:
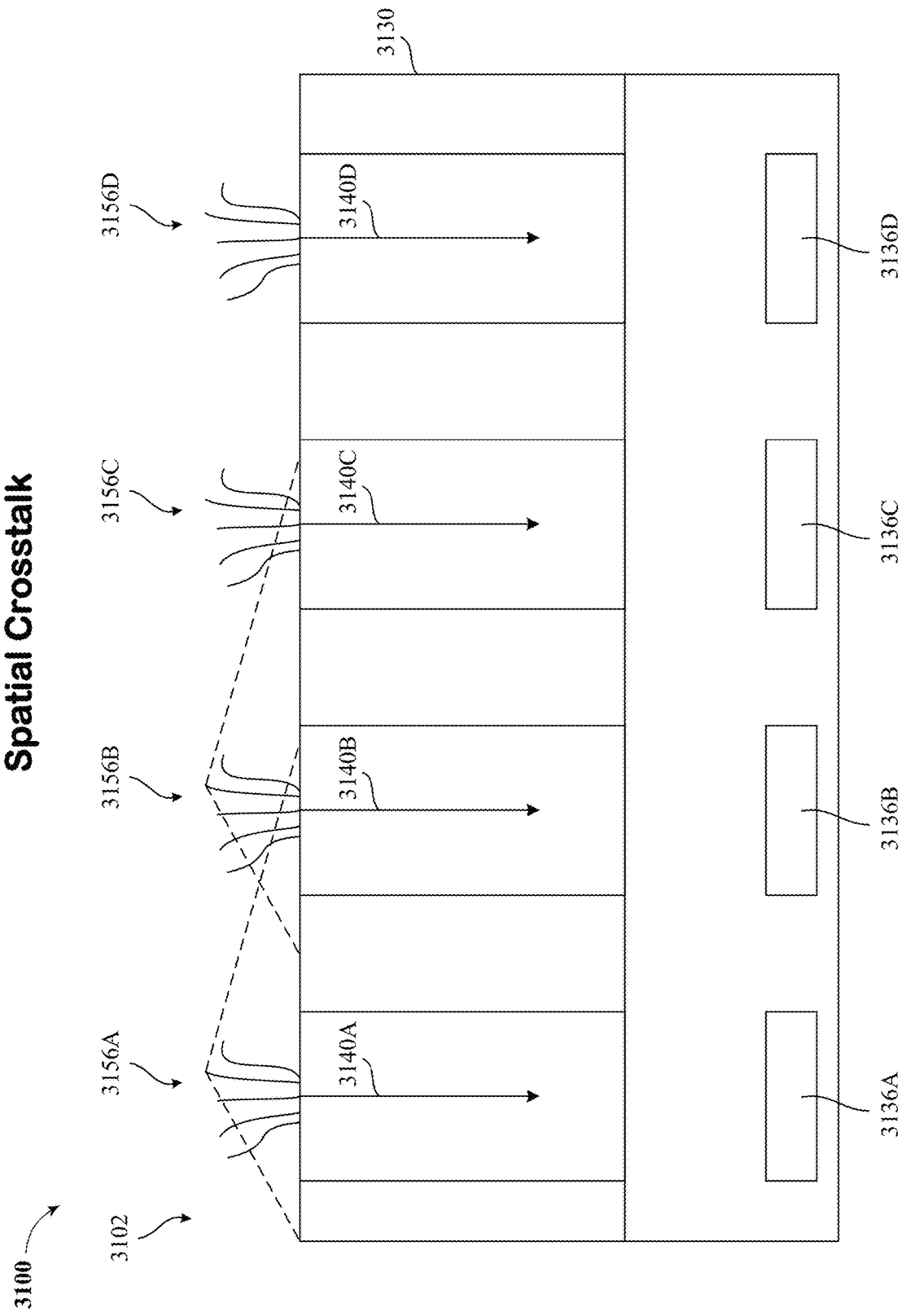
FIG. 31 illustrates one example of spatial crosstalk.

FIG. 31 illustrates one example of spatial crosstalk. FIG. 31 illustrates a detection device 3100 having a plurality of pixel areas 3156A-3156D on a detector surface 602. The detection device 3100 includes light sensors 3136A-3136D. The light sensors 3136A-3136D are associated with and correspond to the pixel areas 3156A-3156D, respectively. Corresponding detection paths 3140A-3140D extend between the light sensors 3136A-3136D and corresponding pixel areas 3156A-3156D. The arrows that indicate the detection paths 3140A-3140D are merely to illustrate a general direction that the light propagates through the respective detection path.

During an imaging event, the detection device 3100 is configured to detect light using the light sensors 3136A-3136D. As demonstrated in FIG. 31 by pyramidal hash marked areas or zones, light emissions (or emission signals)

are propagating from the pixel areas 3156A and 3156B, but light emissions are not propagating from 3156C or 3156D. The light emissions may be indicative of, for example, a positive binding event between the analytes located at the corresponding pixel area and another biomolecule. In particular implementations, the pixel areas 3156A-3156D are illuminated by an excitation light (e.g., 532 nm). The pixel areas 3156A and 3156B are bound to respective biomolecules having light labels (e.g., fluorescent moieties). In response to the excitation stimulus, the pixel areas 3156A and 3156B provide light emissions as demonstrated in FIG. 31.

However, the pixel areas 3156 and the light sensors 3136 may be located relatively close to one another such that light emissions from a non-associated pixel area may be detected by a light sensor. Such light emissions may be referred to as crosstalk emissions or spatial crosstalk. By way of example, the light emissions propagating from the pixel area 3156A include a crosstalk signal and a pixel signal. The pixel signal of the light emissions from the pixel area 3156A is that signal of the light emissions that is configured to be detected by the light sensor 3136A. In other words, the pixel signal includes the light emissions that propagate at an angle that is generally toward the light sensor 3136A such that filter walls 3130 defining the detection path 3140A are capable of directing the light emissions toward the light sensor 3136A. The crosstalk signal is that signal of the light emissions that clears the filter walls 3130 defining the detection path 3140A and propagates into, for example, the detection path 3140B. In such cases, the crosstalk signal may be directed to the light sensor 3136B, which is not associated with the pixel area 3156A. Thus, the light sensor 3136B may be referred to as a non-associated light sensor with respect to the pixel area 3156A.

Using the implementation shown in FIG. 31 as an example, the light sensor 3136A may detect the pixel emissions from the pixel area 3156A and the crosstalk emissions from the pixel area 3156B. Likewise, the light sensor 3136B may detect the pixel emissions from the pixel area 3156B and the crosstalk emissions from the pixel area 3156A. The light sensor 3136C may detect the crosstalk emissions from the pixel area 3156B. However, the pixel area 3156C is not providing light emissions in FIG. 31. Thus, an amount of light detected by the light sensor 3136C is less than the corresponding amounts of light detected by the light sensors 3136A and 3136B. As shown in FIG. 31, the light sensor 3136C only detects crosstalk emissions from the pixel area 3156B, and the light sensor 3136D does not detect crosstalk emissions or pixel emissions.

Emission Overlap

Emission overlap refers to the recording of light from a single fluorophore in multiple channels. In an ideal cyclic reversible termination (CRT) reaction, the different fluorophores would have distinct emission spectra and similar yields. However, the emission spectra of the fluorophores used for sequencing are broad and overlap with one another. Thus, when one fluorophore is excited, its signal also passes through the optical filters of the other channels.

Figure 32:
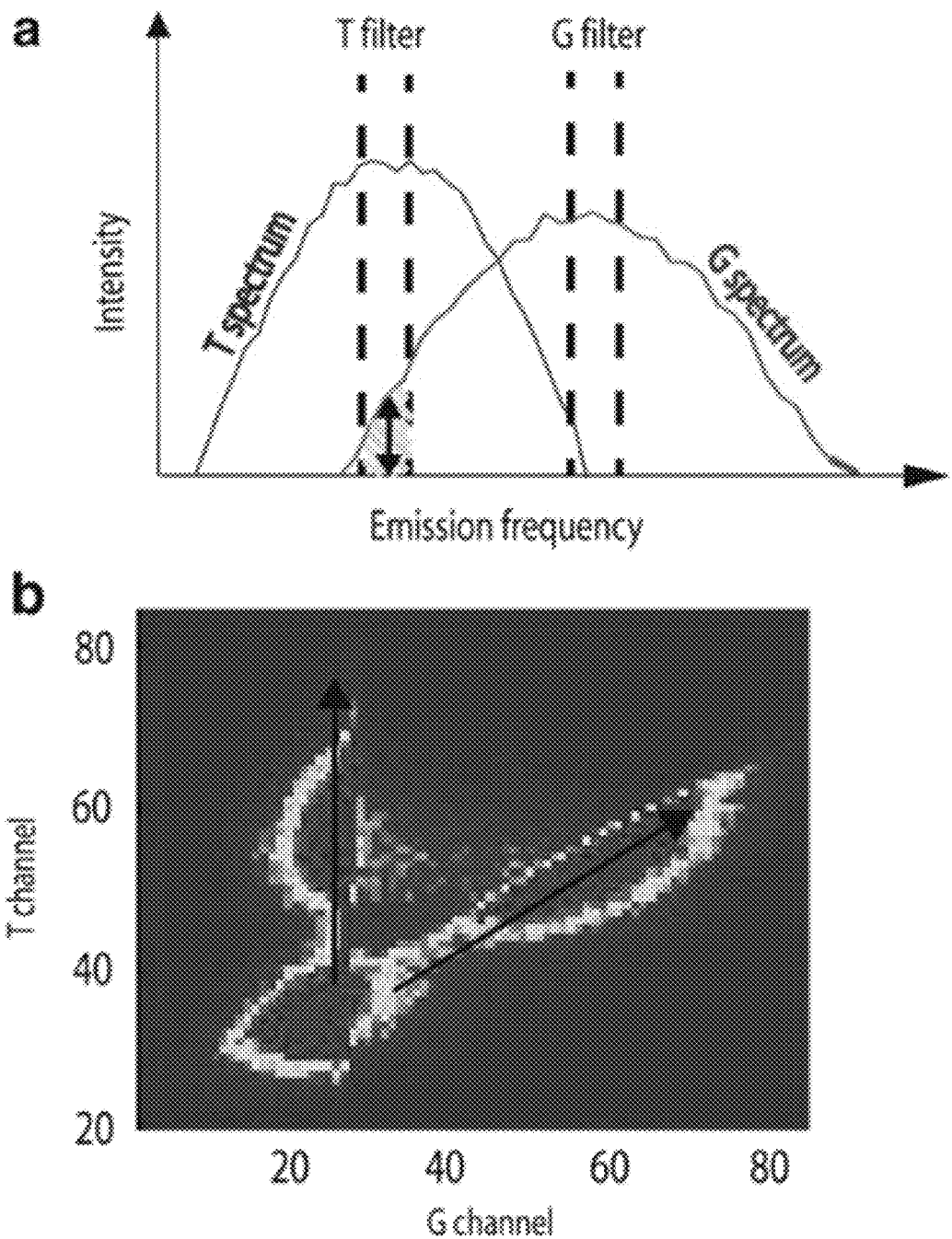
FIG. 32 illustrates one example of emission overlap.

FIG. 32 illustrates one example of emission overlap 3200. FIG. 32*a* shows that the spectrum of the G fluorophore (red) bleeds into the optical spectrum of the T filter (pink hatched region). Thus, when a G fluorophore is excited, a T signal will also be detected.

FIG. 32*b* is a two-dimensional histogram of intensity data of the T channel versus G channel. The G fluorophores (right arrow) transmit to the T channel, hence the positive linearity. On the other hand, the T fluorophores (left arrow) do not transmit to the G channel. Note that there is strong overlap between the "A" and the "C" channels, and the "G" and "T" channels—each pair of fluorescence channels is excited by the same laser.

Fading

Figure 33:
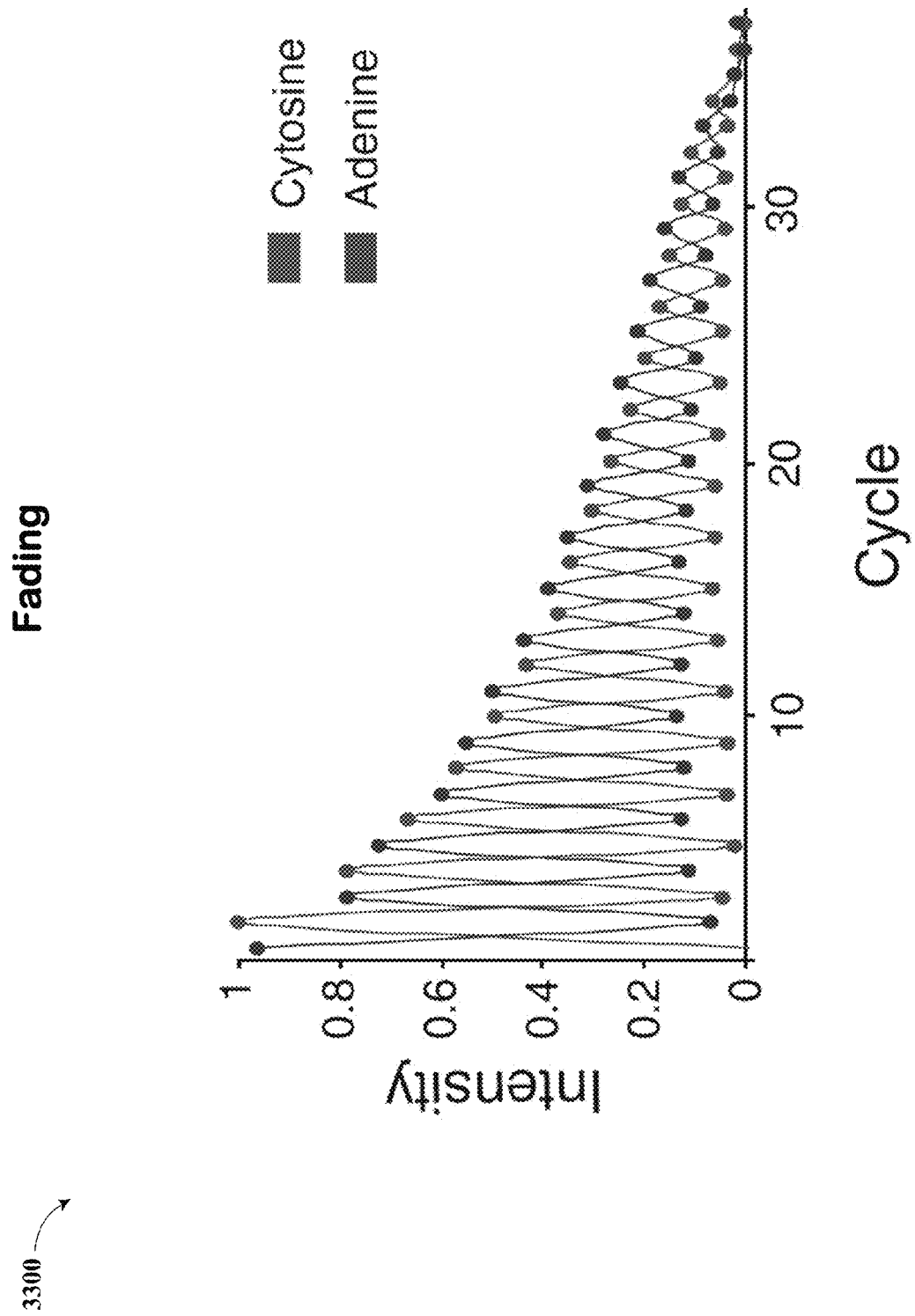
FIG. 33 illustrates one example of fading.

Fading is an exponential decay in fluorescent signal intensity as a function of cycle number. As the sequencing run progress, the analyte strands are washed excessively, exposed to laser emissions that create reactive species, and subject to harsh environmental conditions. All of these lead to a gradual loss of fragments in each analyte, decreasing its fluorescent signal intensity. Fading is also called dimming or signal decay. FIG. 33 illustrates one example of fading 3300. In FIG. 33, the intensity values of analyte fragments with AC microsatellites show exponential decay.

Biases Accounted for by 3D Convolutions

The 3D convolutions 402 detect and account for these biases during the convolution-based base calling 400. Within a same convolution window, the 3D convolution filters 304 of the 3D convolutions 402, such as the first 3D convolution filter 418, convolve over—(i) a plurality of the per-cycle image patches along a temporal dimension 428*k* to detect and account for phasing and prephasing effect between successive ones of the sequencing cycles caused by asynchronous readout of sequence copies of an associated analyte, (ii) a plurality of pixels in each of the per-cycle image patches along spatial dimensions 428*w*, 428*h* to detect and account for spatial crosstalk between adjacent analytes caused by detection of emissions from a non-associated analyte by a corresponding light sensor of an associated analyte, and (iii) each of the imaged channels along a depth dimension 428*c* to detect and account for emission overlap between the imaged channels caused by overlap of dye emission spectra.

By virtue of convolving over a volume that brings image data for a current sequencing cycle and flanking sequencing cycles within a same convolution window, the 3D convolution filters 304 learn to associate observed inter-cycle emissions that cumulatively create intensity patterns representative of: (i) the signal of the underlying base morphology at the current sequencing cycle and (ii) the noise contributed by the flanking sequencing cycles as the phasing and prephasing effect 3000,—with the correct base call prediction for the current sequencing cycle (which, during training, is communicated via the ground truth 2608).

By virtue of convolving over an image patch that brings pixel data from a group of spatially contiguous analytes (pixels) within a same convolution window, the 3D convolution filters 304 learn to associate observed inter-analyte emissions that cumulatively create intensity patterns representative of: (i) the signal of the interrogated/target analyte and (ii) the noise contributed by the adjacent analytes as the spatial crosstalk 3100,—with the correct base call prediction for the interrogated/target analyte (which, during training, is communicated via the ground truth 2608).

By virtue of convolving over image data that expresses intensities captured in each of the imaged channels within a same convolution window, the 3D convolution filters 304 learn to associate observed inter-channel emissions that cumulatively create intensity patterns representative of: (i) the signal of the excited fluorophore in the corresponding imaged channel and (ii) the noise contributed by the non-excited fluorophore(s) in the non-corresponding imaged channel(s) as the emission overlap 3200,—with the correct base call prediction component for the corresponding imaged channel (which, during training, is communicated via the ground truth 2608).

By virtue of convolving the same 3D convolution filters 304 over the sequence of per-cycle image patches, the 3D convolution filters 304 learn to associate observed progressive decrease of the intensity values in the elapsed cycles caused by the fading 3300—with the correct base call prediction for the sequencing cycles (which, during training, is communicated via the ground truth 2608).

The 3D convolution filters 304 are trained on image data obtained for a variety of flow cells, sequencing instruments, sequencing runs, sequencing protocols, sequencing chemistries, sequencing reagents, and analyte densities, and therefore learn many different types of such associations found in the raw data and are optimized over many instances or examples of each type of association. In some implementations, hundreds, thousands, or millions of training examples are used. The optimization includes adjusting/evolving/updating the coefficients/weights/parameters of the convolution kernels (and biases) of the 3D convolution filters 304 to minimize the loss between the predicted base calls and the correct base calls identified by the ground truth. The loss is minimized using stochastic gradient descent with backpropagation.

Output Features

Figure 5:
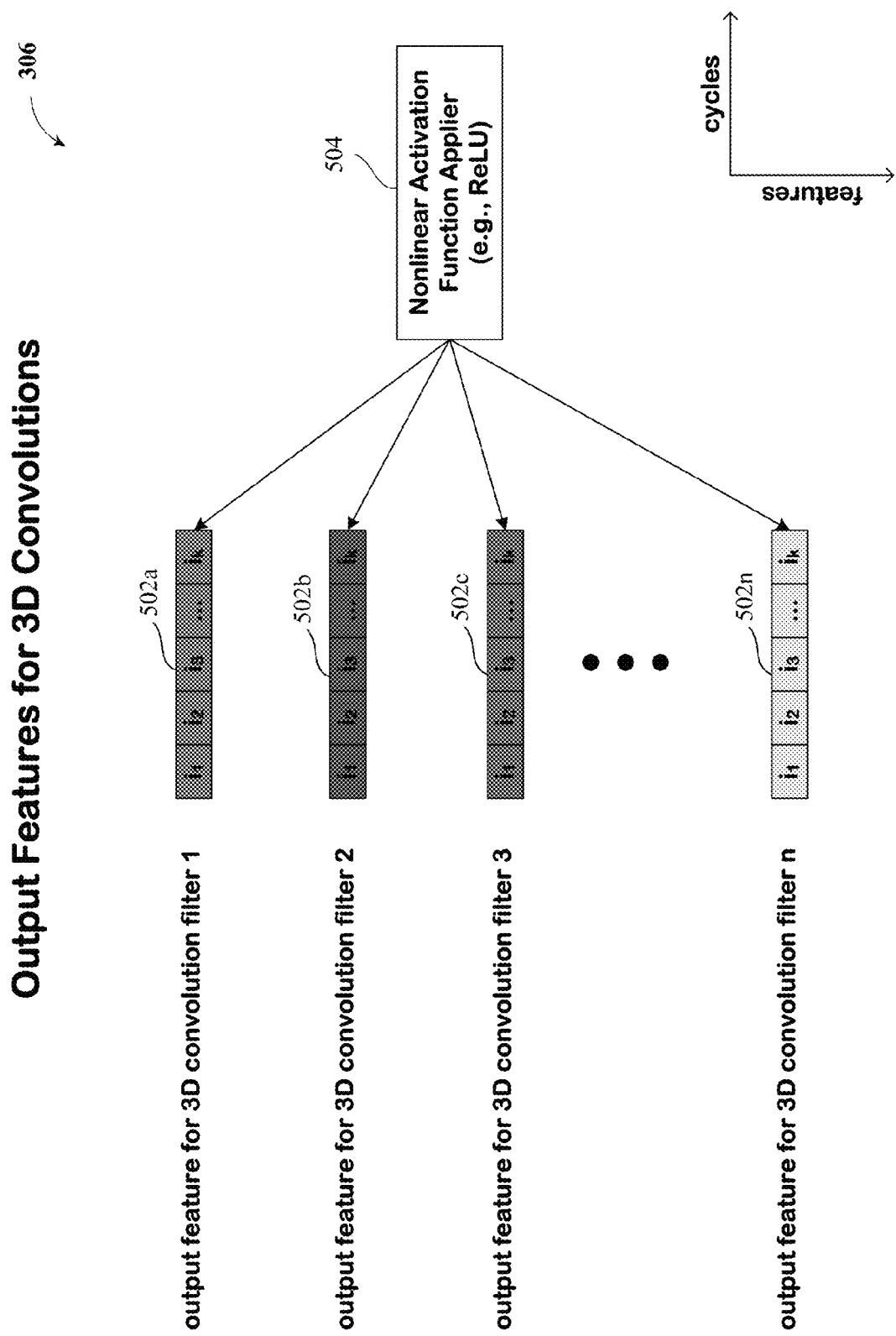
FIG. 5 shows output features produced by the 3D convolutions in accordance with one implementation.

A 3D convolution filter produces at least one output feature as a result of convolving over the sequence of per-cycle image patches on the sliding convolution window basis. For example, the first 3D convolution filter 418 produces the output feature 502a. FIG. 5 shows output features 502a-n produced by n 3D convolution filters 304, respectively. An output feature comprises k feature elements corresponding to k sequencing cycles. The neural network-based base caller 2614 uses this configuration to produce a base call for each sequencing cycle in a prediction. In one implementation, the output features 502a-n are subjected to ReLU by the nonlinear activation function applier 504 to produce activated output features 502a-n.

Supplemental Features

Figure 6:
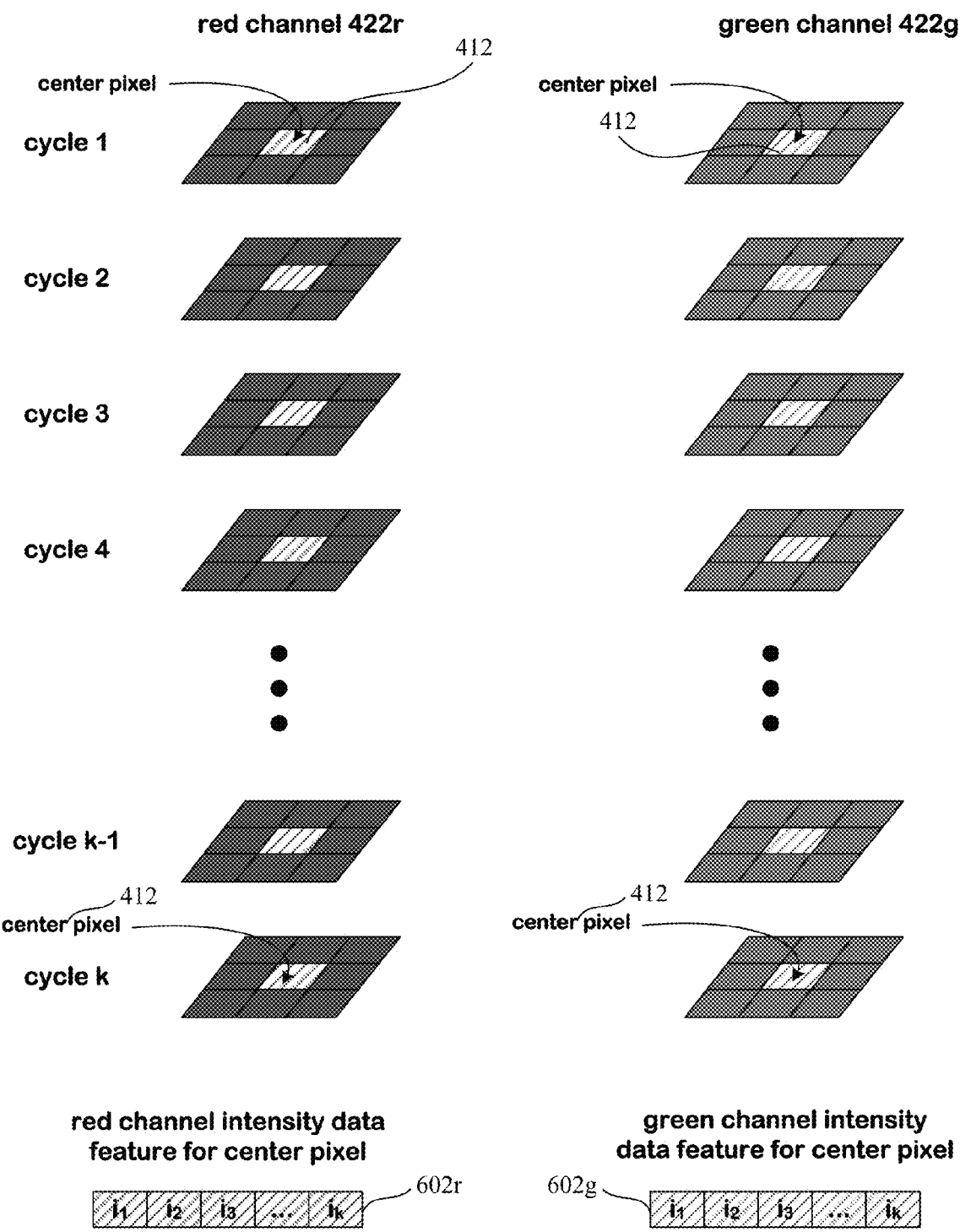
FIG. 6 shows intensity data features generated for a center pixel and used as supplemental input in the convolution-based base calling in accordance with one implementation.

FIG. 6 shows intensity data features generated for the center pixel 412 and used as supplemental input 324 in the convolution-based base calling 400 in accordance with one implementation. The skip connection 326 selects intensity values of the center pixel 412 across the per-cycle pixel patches of the k sequencing cycles and creates intensity data features for the center pixel 412. The selection is done separately for each of the imaged channels. For example, the skip connection 326 accesses the pixel patches for the red channel 422r and selects intensity values of the center pixel 412 in the red channel 422r to create a red channel intensity data feature 602r. Similarly, the skip connection 326 accesses the pixel patches for the green channel 422g and selects intensity values of the center pixel 412 in the green channel 422g to create a green channel intensity data feature 602g. In one implementation, the skip connection 326 concatenates the per-cycle intensity values to create the intensity data features. In another implementation, the skip connection 326 sums the per-cycle intensity values to create the intensity data features.

Figure 7:
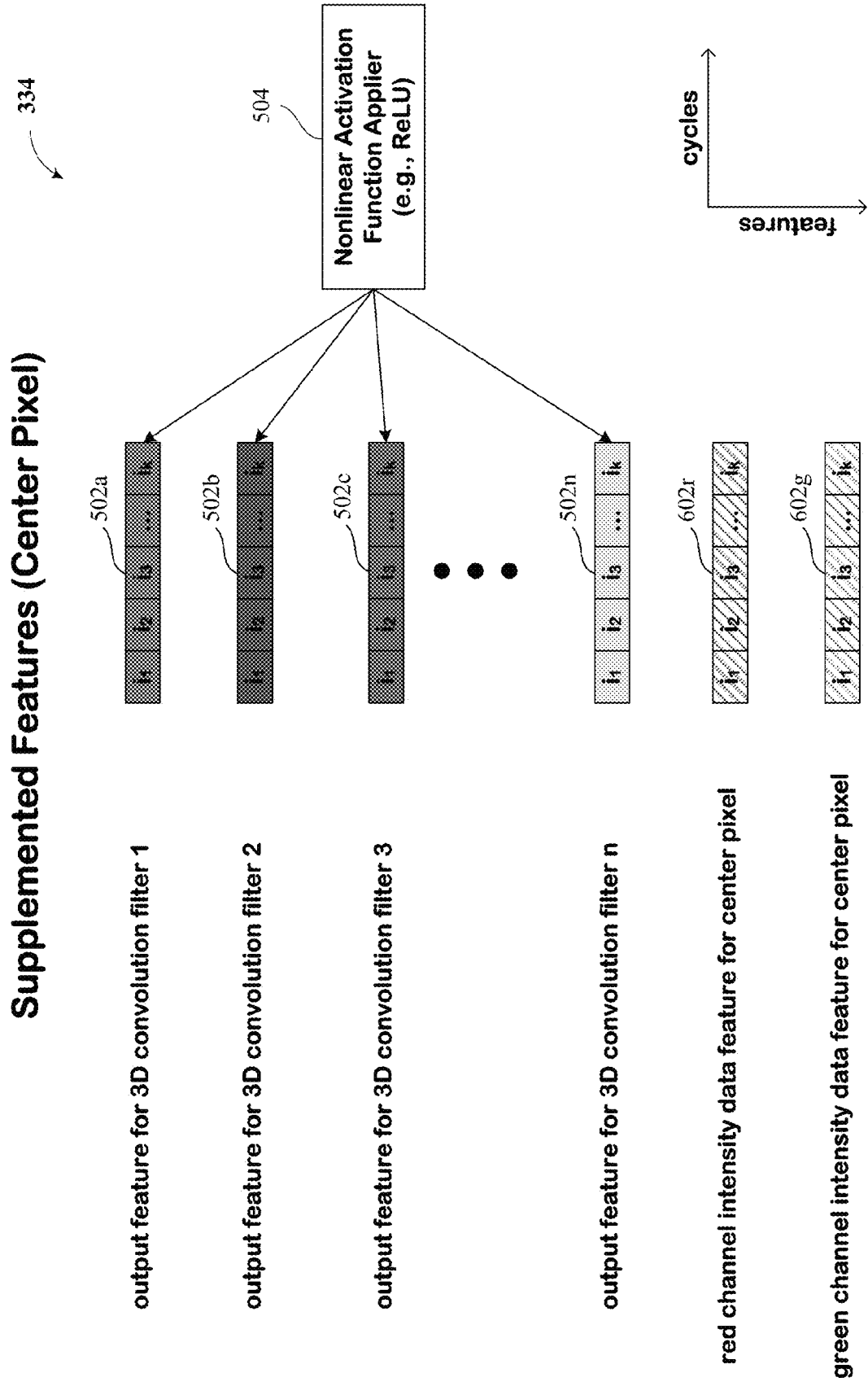
FIG. 7 illustrates the output features of FIG. 5 supplemented with the intensity data features of FIG. 7 in accordance with one implementation.

As shown in FIG. 7, the skip connection 326 supplements the output features 502a-n (or the activated output features 502a-n) with the red and green channel intensity data features 602r, 602g. This causes the neural network-based base caller 2614 to further attend to the intensity data of the center pixel 412.

Cascade of 1D Convolutions

Beginning with the output features 306 supplemented with the intensity data features 324 as starting input, the cascade 330 of 1D convolutions 308 is applied to produce the further output features 312. The 1D convolutions 308 use different receptive fields to detect varying degrees of the asynchronous readout caused by the phasing and prephasing effect 3000.

Figure 8:
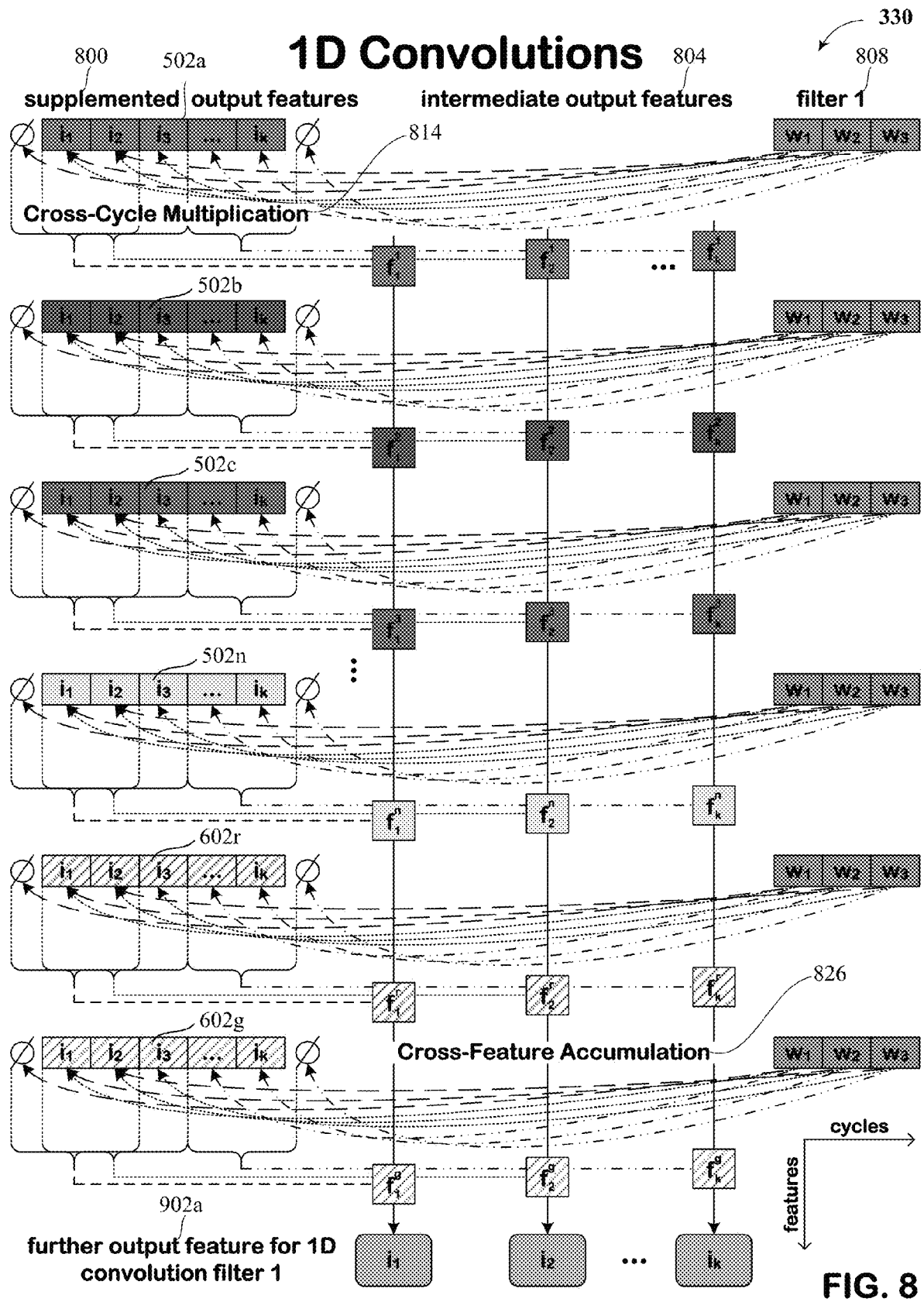
FIG. 8 illustrates one-dimensional (1D) convolutions used in the convolution-based base calling in accordance with one implementation.
Figure 9:
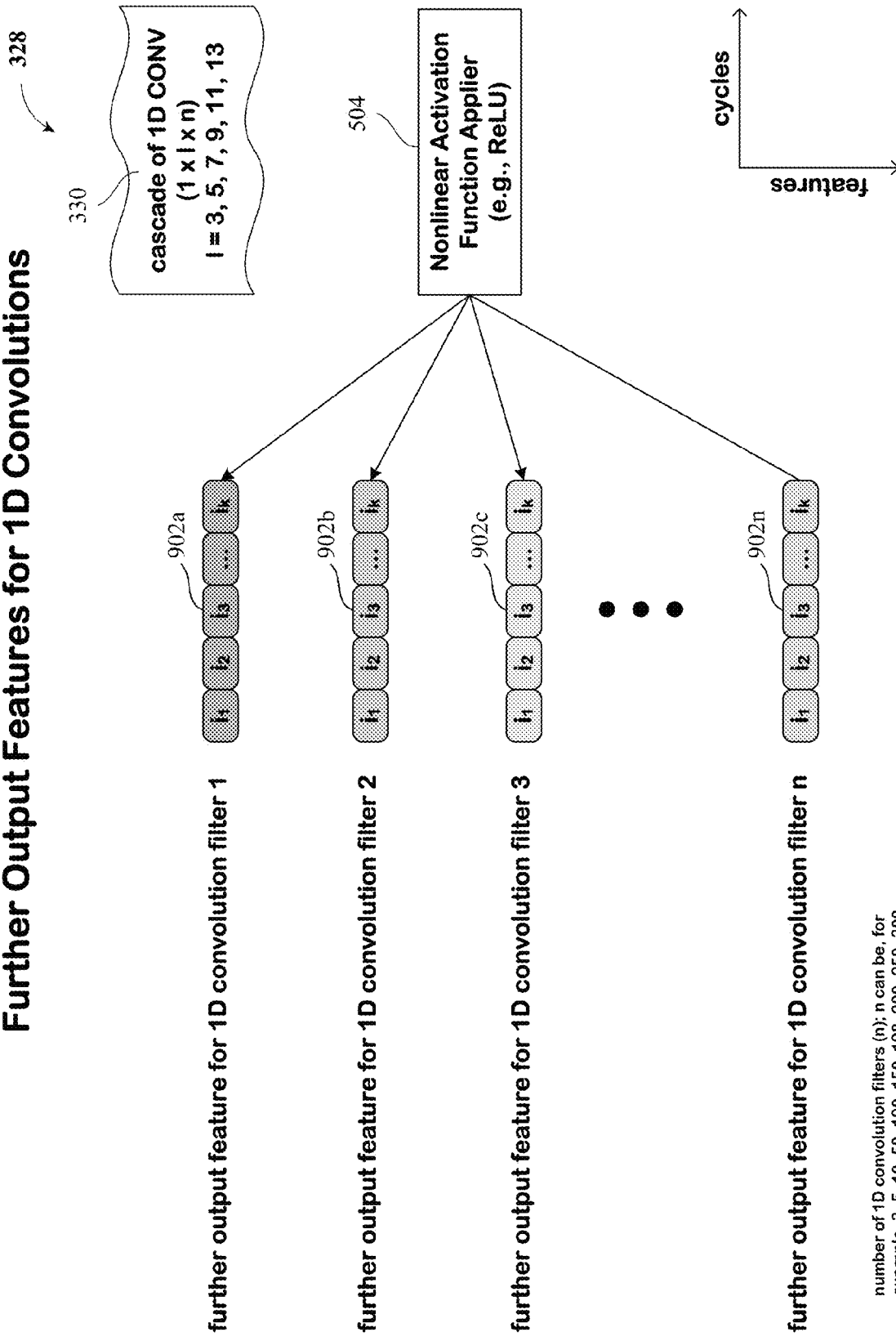
FIG. 9 depicts further output features produced by the 1D convolutions in accordance with one implementation.

Varying Receptive Field to Account for Different Orders of Phasing and Prephasing FIG. 8 shows one implementation of a first 1D convolution filter 808 convolving over the supplemented output features 800, which comprise the output features 502a-n and the intensity data features 602r, 602g. The receptive field/kernel width (l) of the first 1D convolution filter 808 is three because it has three weights/coefficients w1, w2, w3, i.e., l=3. Similarly, for a 1D convolution filter with eleven weights,—l=11. For each l, a bank of 1D convolution filters is applied. That is, the cascade 330 uses a plurality of 1D convolution banks, with each bank comprising a set of 1D convolution filters. In some implementations, each 1D convolution filter bank uses a different l. In other implementations, some of the banks have the same l. Within the cascade 330, from one bank to the next, l can progressively increase, progressively decrease, randomly increase, randomly decrease, or randomly kept the same.

The weights in the 1D convolution filters 308 are element-wise multiplied with the feature elements of the supplemented output features 800. Since each feature element corresponds to one of the k sequencing cycles, element-wise multiplication between the weights and the corresponding feature elements is referred to herein as "cross-cycle multiplication." In one implementation, the cross-cycle multiplication results in mixing of information between the sequencing cycles. As l changes, the window of sequencing cycles between which the information is mixed also changes to account for different number of flanking sequencing cycles that contribute to the signal of a current sequencing cycle (t), i.e., different levels/orders/degrees of phasing (t−1, t−2, t−3, etc.) and prephasing (t+1, t+2, t+3, etc.).

Further Output Features

One instance of the cross-cycle multiplication and subsequent summation yields an intermediate output feature. In FIG. 8, the intermediate output features 804 are identified using the notation $f_j^i$, where i denotes the output feature or the intensity data feature and j denotes the cycle number. By use of SAME padding, the cross-cycle multiplication and summation across the supplemented output features 800 results in k intermediate output features corresponding to the k sequencing cycles.

The output of the first 1D convolution filter 808 convolving over the supplemented output features 800 is a further output feature 902a. The further output feature 902a is produced by cross-feature accumulation 826 of the intermediate output features 804 such that intermediate output features at the same cycle position (same j) are summed to produce a feature element for that cycle position in the further output feature 902a. For example, the intermediate output features at the first cycle (j=1) are summed across the supplemented output features 800 to produce the first feature element (j=1) of the further output feature 902a. The cross-feature accumulation 826 results in the further output feature 902a having k feature elements that correspond to the k sequencing cycles. The neural network-based base caller 2614 uses this configuration to produce a base call for each sequencing cycle in a prediction.

As discussed above, each bank in the cascade 330 uses a set of 1D convolution filters. Each 1D convolution filter, as a result of convolving over the supplemented output features 800, produces a further output feature. Thus, further output features 902a-n are produced by n 1D convolution filters 308, respectively. In one implementation, the further output features 902a-n are subjected to ReLU by the nonlinear activation function applier 504 to produce activated further output features 902a-n.

Pointwise Convolutions

The further output features produced by the last bank of 1D convolution filters in the cascade 330 (i.e., the ultimate further output features) are fed as input to the pointwise convolution filters 310. In some implementations, the activated further output features are fed as input.

In one implementation, the number of pointwise convolution filters applied on the ultimate further output features is a function of the number of analytes (pixels) that are to be base called (p). In another implementation, it is a function of: (i) the number of analytes (pixels) that are to be base called (p) as well as (ii) the number of imaged channels for which a base call prediction component (c) is generated by the neural network-based base caller 2614.

For example, the convolution-based base calling 400 is directed at base calling the center pixel 412 (i.e., p=1) and involves generating a first base call prediction component 1112 for the red channel 422r and a second base call prediction component 1132 for the green channel 422g (i.e., c=2). Here, the number of pointwise convolution filters is pxc, i.e., 2. Similarly, when base calling the entire pixel patch (i.e., p=9) for the red and green channels 422r, 422g, 18 pointwise convolution filters are used.

Figure 10:
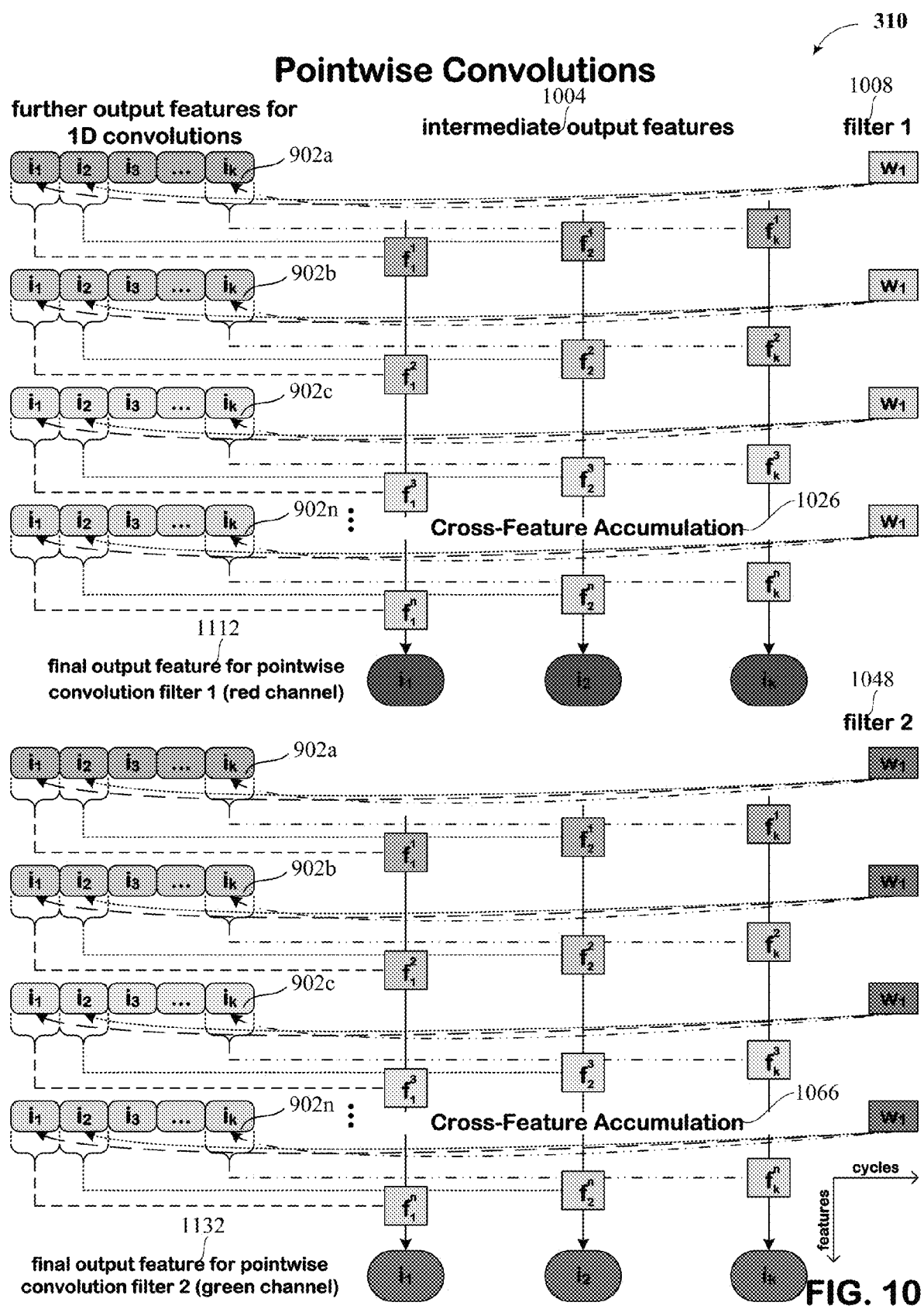
FIG. 10 depicts pointwise convolutions used in the convolution-based base calling in accordance with one implementation.

In FIG. 10, two pointwise convolution filters 1008, 1048 produce the final output features 1112, 1132 by cross-feature accumulations 1026, 1066, respectively. The pointwise convolution filters 1008, 1048 have their own respective kernel weight/coefficient, which is separately applied on the further output features 328.

Final Output Features

The resulting final output features 312 have k feature elements corresponding to the k sequencing cycles. Each final output feature corresponds to one of the imaged channels for which a base call prediction component is generated by the neural network-based base caller 2614. For example, the first final output feature 1112 corresponds to the base call prediction component generated for the red channel 422r and the second final output feature 1132 corresponds to the base call prediction component generated for the green channel 422g.

Output Layer

Figure 11:
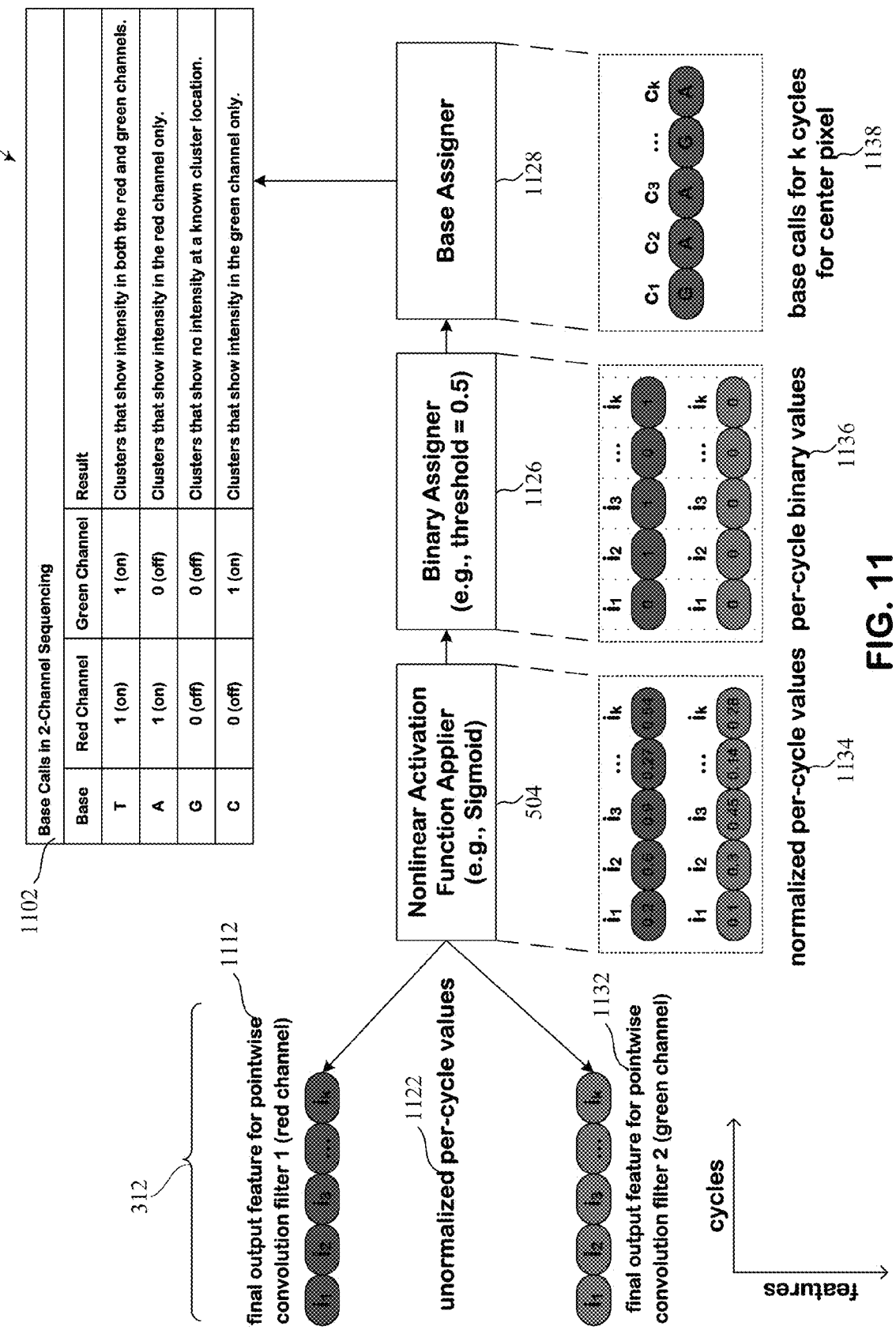
FIG. 11 shows an output layer that processes the final output features produced by the pointwise convolutions and emits base calls for a center pixel in accordance with one implementation.

The output layer 314 operates on the final output features 312 and produces the base calls 1138. The final output features 312 comprise unnormalized per-cycle values 1122. The nonlinear activation function applier 504 converts the unnormalized per-cycle values 1122 into normalized per-cycle values 1134. In one implementation, the nonlinear activation function applier 504 applies a sigmoid function that squashes the unnormalized per-cycle values 1122 between zero and one, as shown in FIG. 11 with respect to the normalized per-cycle values 1134.

A binary assigner 1126 then converts the normalized per-cycle values 1134 into per-cycle binary values 1136 based on a threshold (e.g., 0.5). The binary assigner 1126 can be part of the output layer 314. In one implementation, those squashed per-cycle values that are below the threshold are assigned a zero value and those squashed per-cycle values that are above the threshold are assigned a one value.

A base assigner 1128 then base calls the associated analyte of the center pixel 412 at each of the k sequencing cycles based on the per-cycle binary values 1136 at corresponding positions (e.g., i1, i2, i3, ik) in the final output features 312. The base assigner 1128 can be part of the output layer 314. In FIG. 11, the base calls 1138 are assigned using a 2-channel sequencing base calling scheme 1102 that uses on (1) and off (0) bits to assign a base letter.

In some implementations, the output layer 314 comprises a softmax function that produces an exponentially normalized probability distribution of a base incorporated at a sequencing cycle in an associated analyte to be base called being A, C, T, and G, and classifies the base as A, C, T, or G based on the distribution. In one implementation, the softmax function is applied by a softmax operator 2623, which can be part of the output layer 314.

Regarding softmax, softmax is an output activation function for multiclass classification. Formally, training a so-called softmax classifier is regression to a class probability, rather than a true classifier as it does not return the class but rather a confidence prediction of each class's likelihood. The softmax function takes a class of values and converts them to probabilities that sum to one. The softmax function squashes a k-dimensional vector of arbitrary real values to k-dimensional vector of real values within the range zero to one. Thus, using the softmax function ensures that the output is a valid, exponentially normalized probability mass function (nonnegative and summing to one).

Consider that $\tilde{y}_i$ is the i th element of the vector $\tilde{y}=[\tilde{y}_1, \tilde{y}_2, \ldots \tilde{y}_n]$:

$$\tilde{y}_i = (\text{softmax}(\tilde{z}))_i = \frac{\exp(\tilde{z}_i)}{\sum_{j=1}^{j=N} \exp(\tilde{z}_j)},$$

where $\tilde{y}$ is a vector of length n, where n is the number of classes in the classification. These elements have values between zero and one, and sum to one so that they represent a valid probability distribution.

An example softmax activation function 13406 is shown in FIG. 134. Softmax 13406 is applied to three classes as z|>softmax $$([z; \frac{z}{10}; -2z]).$$

Note that the three outputs always sum to one. They thus define a discrete probability mass function.

When used for classification, $\tilde{y}_i$ gives the probability of being in class i.

$$P(Y=i|\tilde{z})=(\text{softmax }(\tilde{z}))_i=\tilde{y}_i$$

The name "softmax" can be somewhat confusing. The function is more closely related to the argmax function than the max function. The term "soft" derives from the fact that the softmax function is continuous and differentiable. The argmax function, with its result represented as a one-hot vector, is not continuous or differentiable. The softmax function thus provides a "softened" version of the argmax. It would perhaps be better to call the softmax function "softargmax," but the current name is an entrenched convention.

Base Calling Pixel Patch

Figure 12:
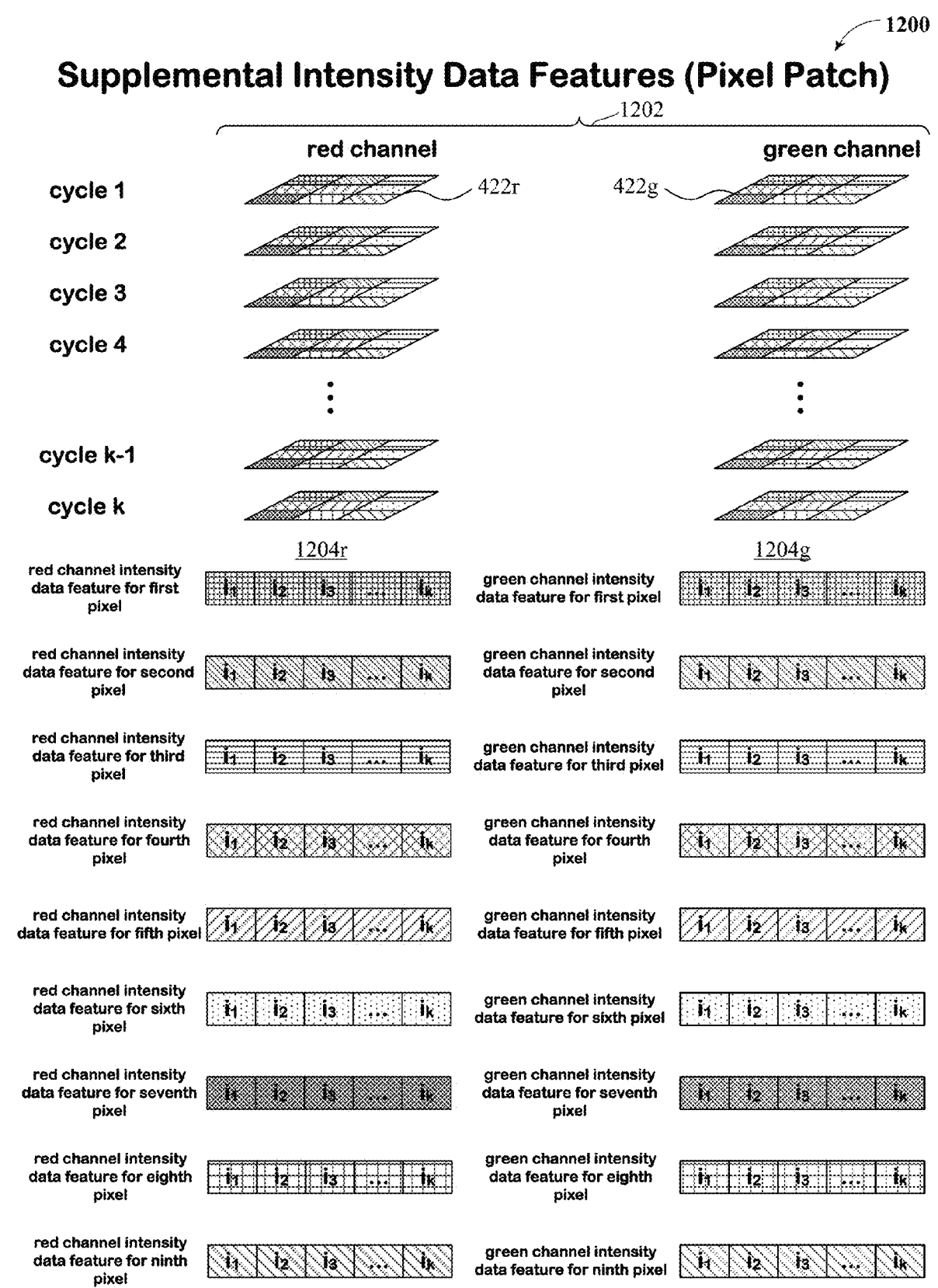
FIG. 12 shows intensity data features generated for a pixel patch and used as supplemental input in the convolution-based base calling in accordance with one implementation.

The neural network-based base caller 2614 can simultaneously base call a plurality of associated analytes depicted by corresponding pixels in a pixel patch 1202. FIG. 12 shows intensity data features 1204r, 1204g generated for the pixel patch 1202 and used as supplemental input 1200 in the convolution-based base calling 1400 in accordance with one implementation.

Figure 13:
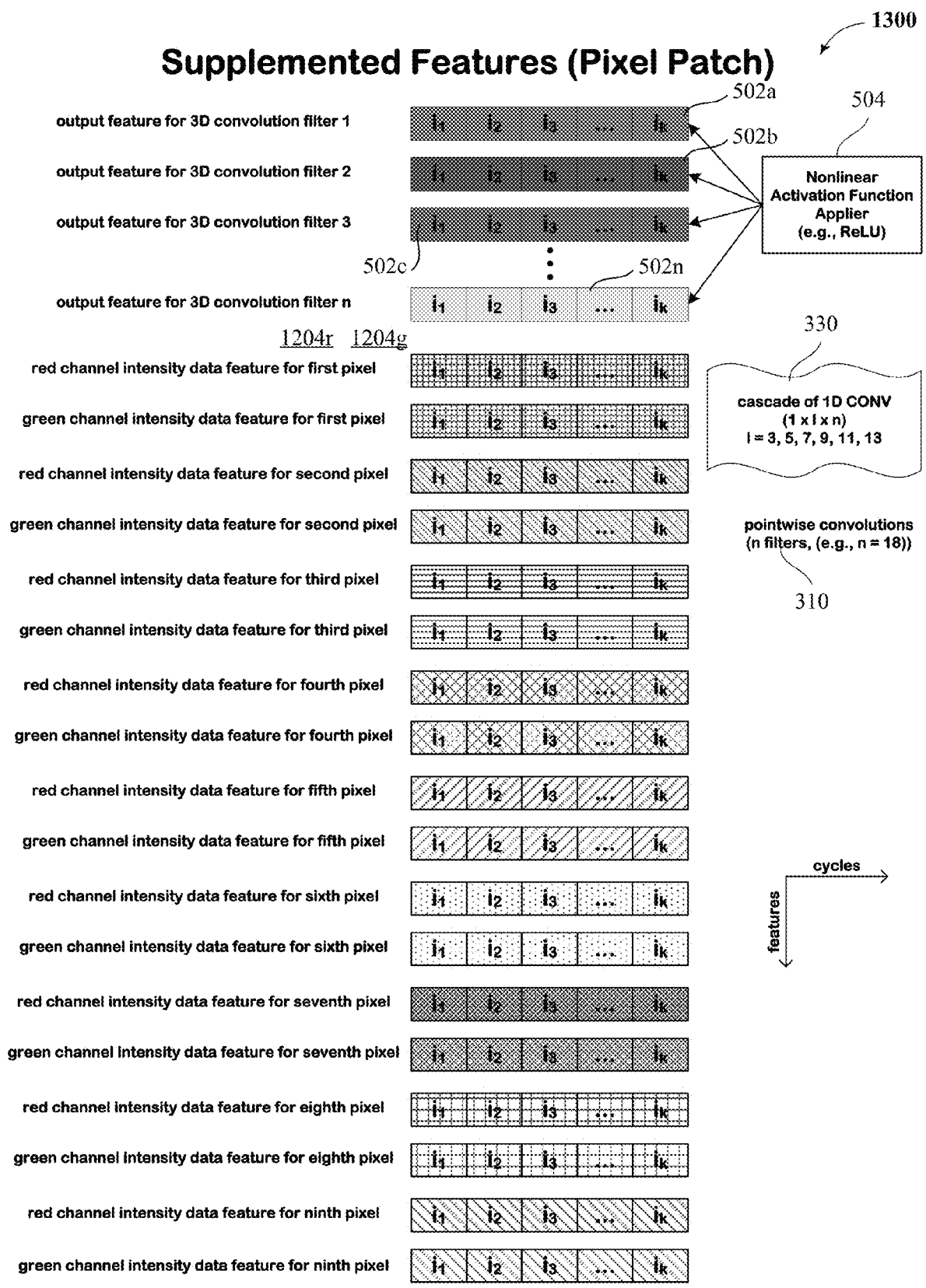
FIG. 13 illustrates the output features of FIG. 5 supplemented with the intensity data features of FIG. 12 in accordance with one implementation.
Figure 14:
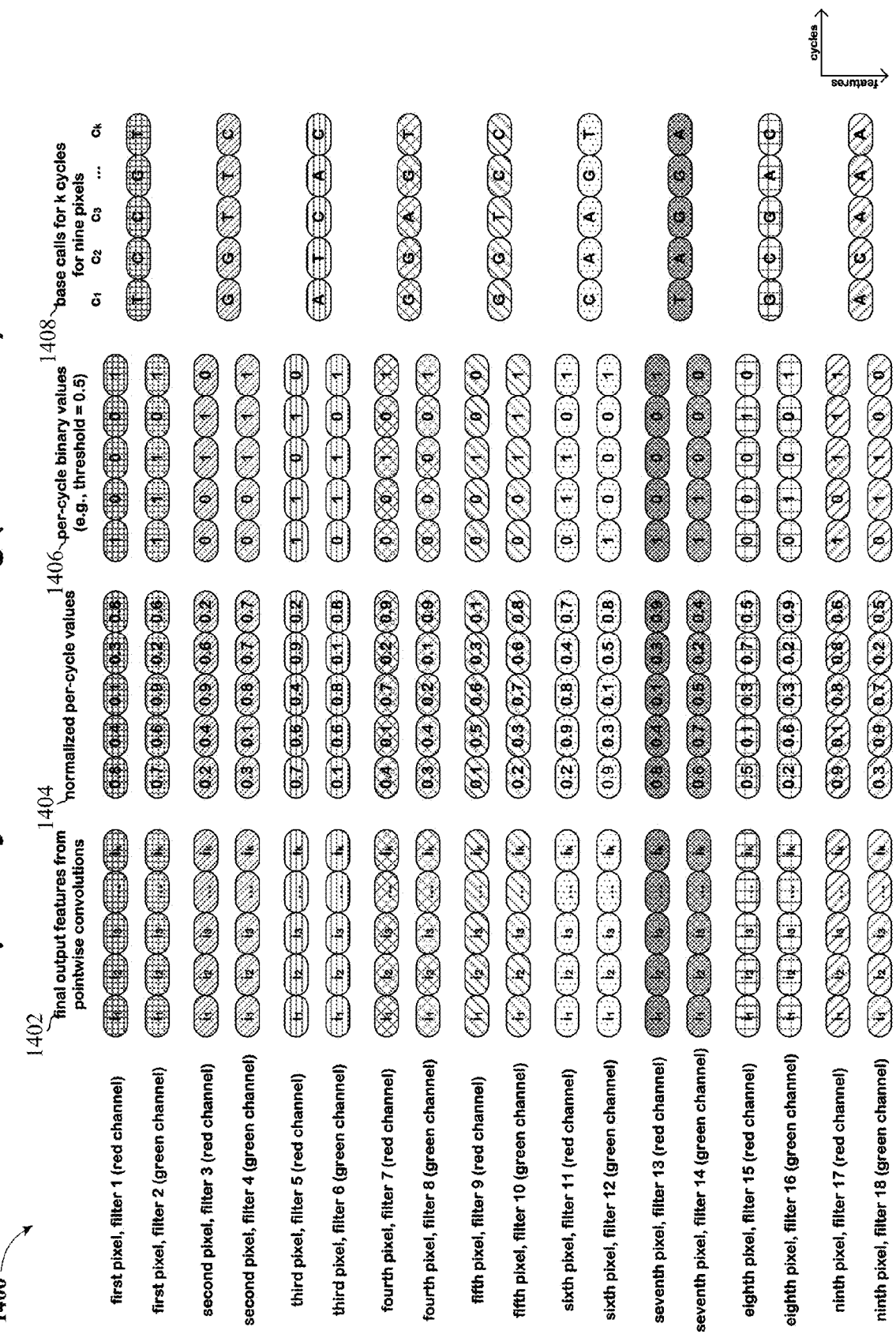
FIG. 14 illustrates the output layer processing the final output features produced by the pointwise convolutions and emitting base calls for pixels in the pixel patch in accordance with one implementation.

FIG. 13 illustrates the output features 502*a*-*n* supplemented 1300 with the intensity data features 1204*r*, 1204*g* in accordance with one implementation. FIG. 14 illustrates the output layer 314 processing the final output features 1402 produced by the pointwise convolutions and emitting base calls 1408 for pixels in the pixel patch 1202 in accordance with one implementation. FIG. 14 also shows the normalized per-cycle values 1404 for the pixel patch 1202 and the per-cycle binary values 1406 for the pixel patch 1202.

Base Calling—Segregated Convolutions

Figure 15:
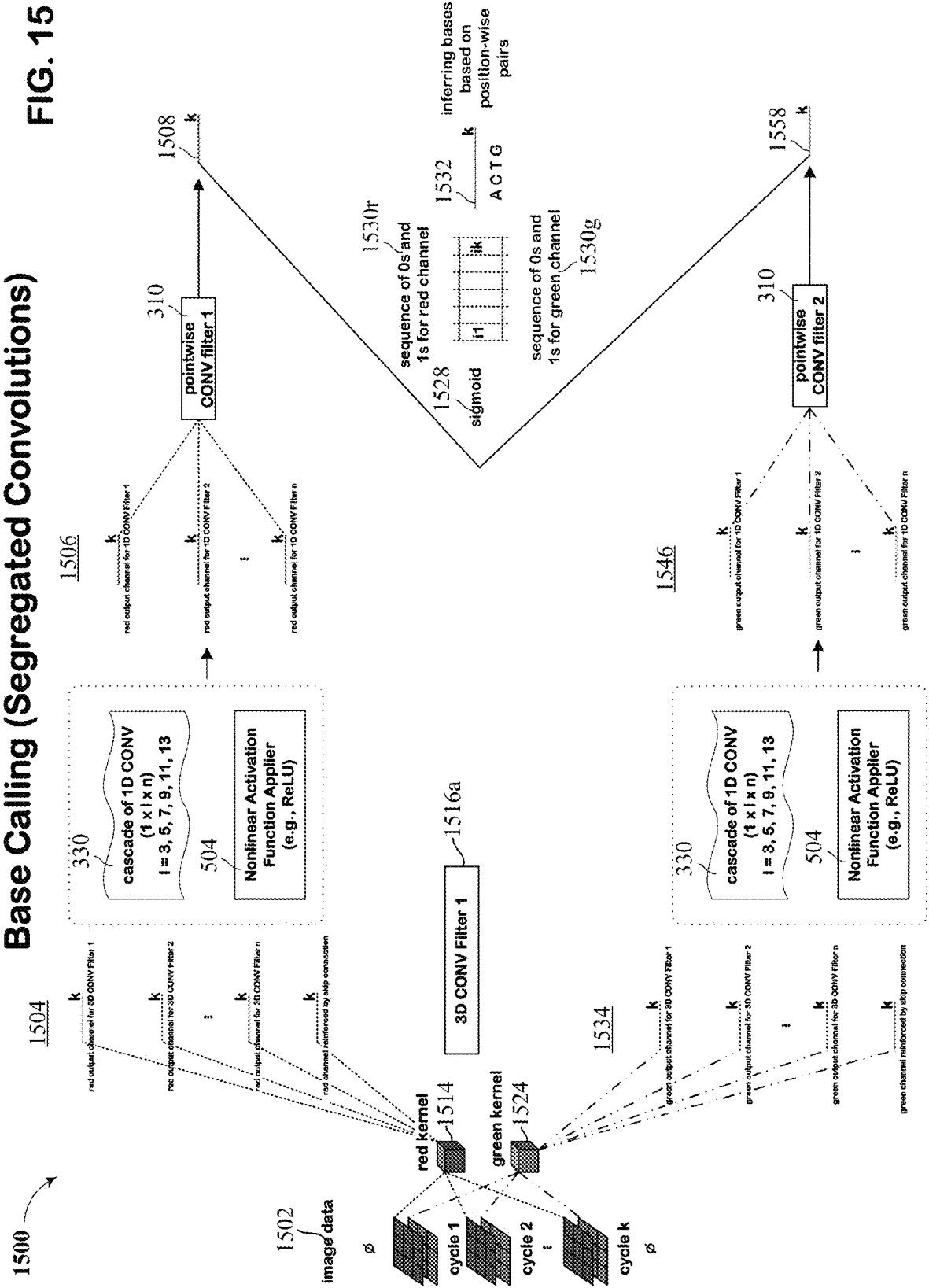
FIG. 15 depicts one implementation of the convolution-based base calling using segregated convolutions that do not mix information between the imaged channels.

FIG. 15 depicts one implementation of the convolution-based base calling 1500 using segregated convolutions that do not mix information between the imaged channels. In FIG. 15, the image data 1502 has pixel intensity data in two channels, a red channel and a green channel. A first 3D convolution filter 1516*a* has two convolution kernels: a red kernel 1514 and a green kernel 1524. The red kernel 1514 convolves over the pixel intensity data in the red channel and the green kernel 1524 convolves over the pixel intensity data in the green channel.

Red kernels of n 3D convolution filters produce n red output channels 1504. Green kernels of the n 3D convolution filters produce n green output channels 1534. The outputs of the red and green kernels are not mixed and kept segregated. Then, separate processing pipelines are initiated for the red and green output channels 1504, 1534 such that downstream convolutions that operate on the red and green output channels 1504, 1534 do not mix information between the red and green output channels 1504, 1534.

The downstream convolutions (e.g., 1D convolutions and pointwise convolutions) produce separate red and green output channels such as 1506 (red), 1546 (green) and 1508 (red), 1558 (green). Then, a sigmoid function 1528 produces a binary sequence for the red channel 1530*r* and a binary sequence for the green channel 1530*g*, which are in turn used to infer base calls 1532 based on the position-wise pairs.

Base Calling—Segregated 3D Convolutions, Mixed 1 Convolutions

Figure 16:
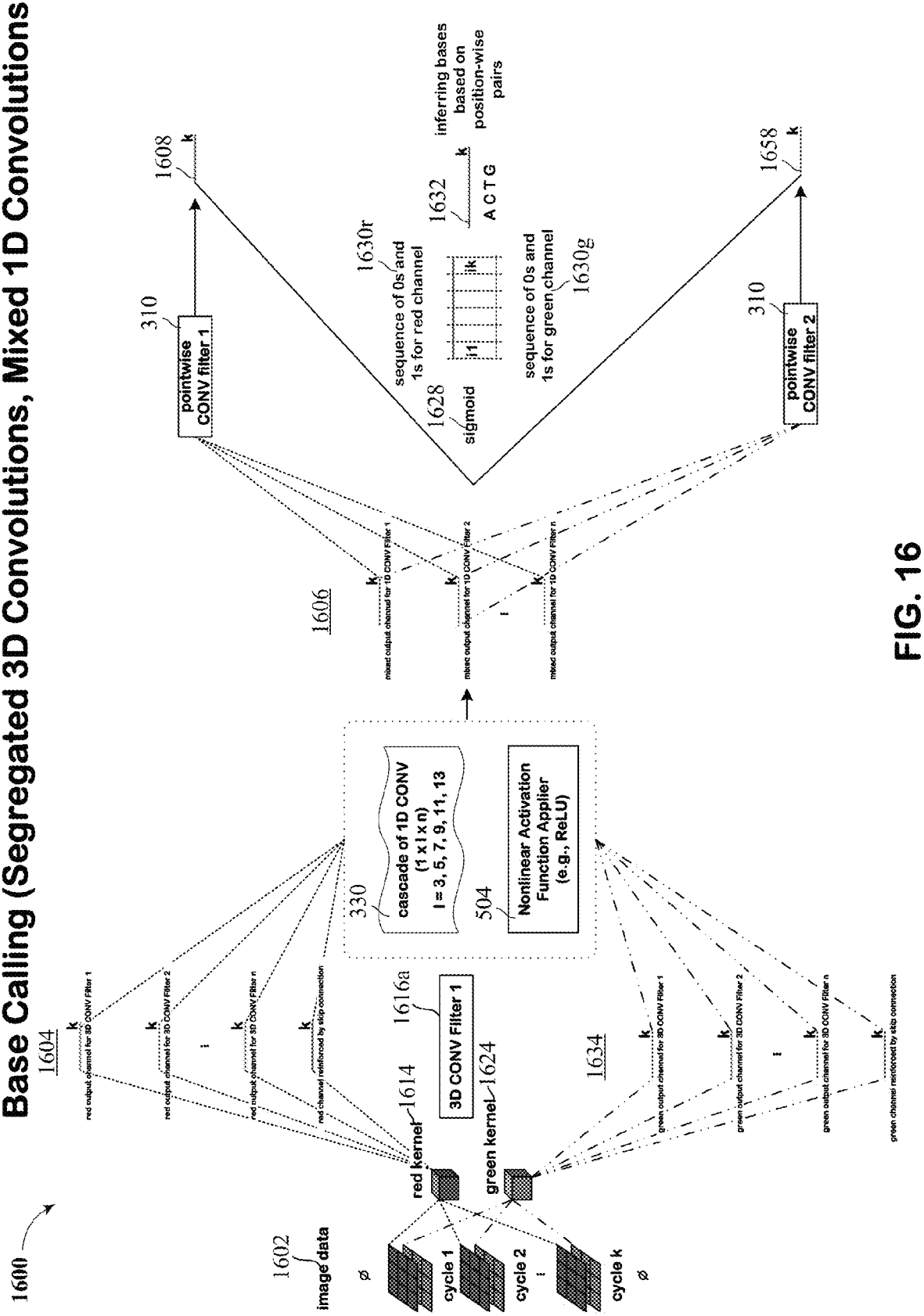
FIG. 16 depicts one implementation of the convolution-based base calling using segregated 3D convolutions that do not mix information between the imaged channels and 1D convolutions that mix information between the imaged channels.

FIG. 16 depicts one implementation of the convolution-based base calling 1600 using segregated 3D convolutions that do not mix information between the imaged channels and 1D convolutions that mix information between the imaged channels. In FIG. 16, the image data 1602 has pixel intensity data in two channels, a red channel and a green channel. A first 3D convolution filter 1616*a* has two convolution kernels: a red kernel 1614 and a green kernel 1624. The red kernel 1614 convolves over the pixel intensity data in the red channel and the green kernel 1624 convolves over the pixel intensity data in the green channel.

Red kernels of n 3D convolution filters produce n red output channels 1604. Green kernels of the n 3D convolution filters produce n green output channels 1634. The outputs of the red and green kernels 1604, 1634 are not mixed and kept segregated.

Then, downstream convolutions (e.g., 1D convolutions) that operate on the red and green output channels 1604, 1634 mix information between the red and green output channels 1504, 1534 and produce mixed output channels 1606.

The mixed output channels 1606 are subjected to pointwise convolutions to produce separate red and green final output channels 1608 (red), 1658 (green). Then, a sigmoid function 1628 produces a binary sequence for the red channel 1630*r* and a binary sequence for the green channel 1630*g*, which are in turn used to infer base calls 1632 based on the position-wise pairs.

Quality Scoring

In one implementation, the neural network-based base caller 2614 uses the normalized per-cycle values 1134 in the final output features 312 of the imaged channels to assign quality scores 2610 to base call predictions emitted by the output layer 314 based on a quality score mapping. The quality score mapping is determined by: (i) calculating predicted error rates for base call predictions made on training data 2505 and determining corresponding predicted quality scores, (ii) determining a fit between the predicted quality scores and empirical quality scores determined from empirical base calling error rates derived from test data, and (iii) correlating the predicted quality scores to the empirical quality scores based on the fit.

In one implementation, the sigmoid outputs as the normalized per-cycle values 1134 can be used to interpret the quality scores 2610 as follows:

| Red Channel Sigmoid | Green Channel Sigmoid | Threshold | Red Channel-Assigned Binary & Confidence | Green Channel-Assigned Binary & Confidence | Base Call Probability | Probability of Error | Logarithmic Probability | Quality Score |
|---|---|---|---|---|---|---|---|---|
| Cycle 1 | | | | | | | | |
| 0.7 | 0.1 | 0.5 | 1 with 90% confidence | 0 with 70% confidence | 0.7 * 0.9 = 0.63 | (1 − 0.63) = 0.37 | −10 * log10 (0.37) = 4.3 | Q = 4 |
| Cycle 2 | | | | | | | | |
| 0.9 | 0.8 | 0.5 | 1 with 90% confidence | 1 with 780% confidence | 0.9 * 0.8 = 0.72 | (1 − 0.72) = 0.28 | −10 * log10 (0.28) = 5.5 | Q = 5 |

In one implementation, the quality scores 2610 are generated by a quality score mapper 2613, which can be part of the neural network-based base caller 2614. FIG. 34*a* shows one example of quality score mapping 3400 produced by the quality score mapper 2613 from raw quality scores with a mean around Q37. FIG. 34*b* shows the observed correspondence between the channel-wise sigmoid scores and the predicted quality scores.

Compact Convolution-Based Base Calling

The discussion now turns to so-called "compact convolution-based base calling." The compact convolution-based base calling uses image data from a subset of the k sequencing cycles to predict a base call on a cycle-by-cycle basis. It also uses fewer convolution filters per convolution window compared to the convolution-based base calling 300 discussed above. For these reasons, the compact convolution-based base calling is more suited for real-time base calling and implementation on central processing unit (CPU) computing.

The compact convolution-based base calling uses signals from a previous timestep/convolution window/sequencing cycle to predict a base call for a current timestep/convolution window/sequencing cycle. These signals include: (i) the base call predicted in the previous timestep/convolution window/sequencing cycle and (ii) the probability distribution of the polymerase population movement in the previous sequencing cycle. Within each timestep/convolution window, the compact convolution-based base calling uses 3D convolutions, 1D convolutions, and pointwise convolutions to predict the base call.

In particular, the compact convolution-based base calling involves processing the sequence of per-cycle image patches on a sliding convolution window basis such that, in a timestep/convolution window/sequencing cycle, it uses as input: (i) image data comprising a per-cycle image patch for a current sequencing cycle (t), per-cycle image patches for one or more successive sequencing cycles (t+1, t+2, . . . ), and per-cycle image patches for one or more preceding sequencing cycles (t−1, t−2, . . . ), (ii) phasing and prephasing data, and (iii) base context data, and produces, as output, a base call for the current timestep/convolution window/sequencing cycle (t) and for one or more of the associated analytes to be base called. The compact convolution-based base calling further involves sequentially outputting the base call at each successive timestep/convolution window/sequencing cycle and base calling the associated analytes at each of the sequencing cycles.

Phasing and Prephasing Data

The phasing and prephasing data 1800 represents probability distribution of the polymerase population movement 1700. The probability distribution 1700 is across sequence copies of an associated analyte 1702 for: (i) a current sequence position 1724 corresponding to the current sequence cycle (t), (ii) leading sequence positions 1728 corresponding to the successive sequencing cycles (t+1, t+2, . . . ), and (iii) lagging sequence positions 1722 corresponding to the preceding sequencing cycles (t−1, t−2, . . . ).

Figure 17:
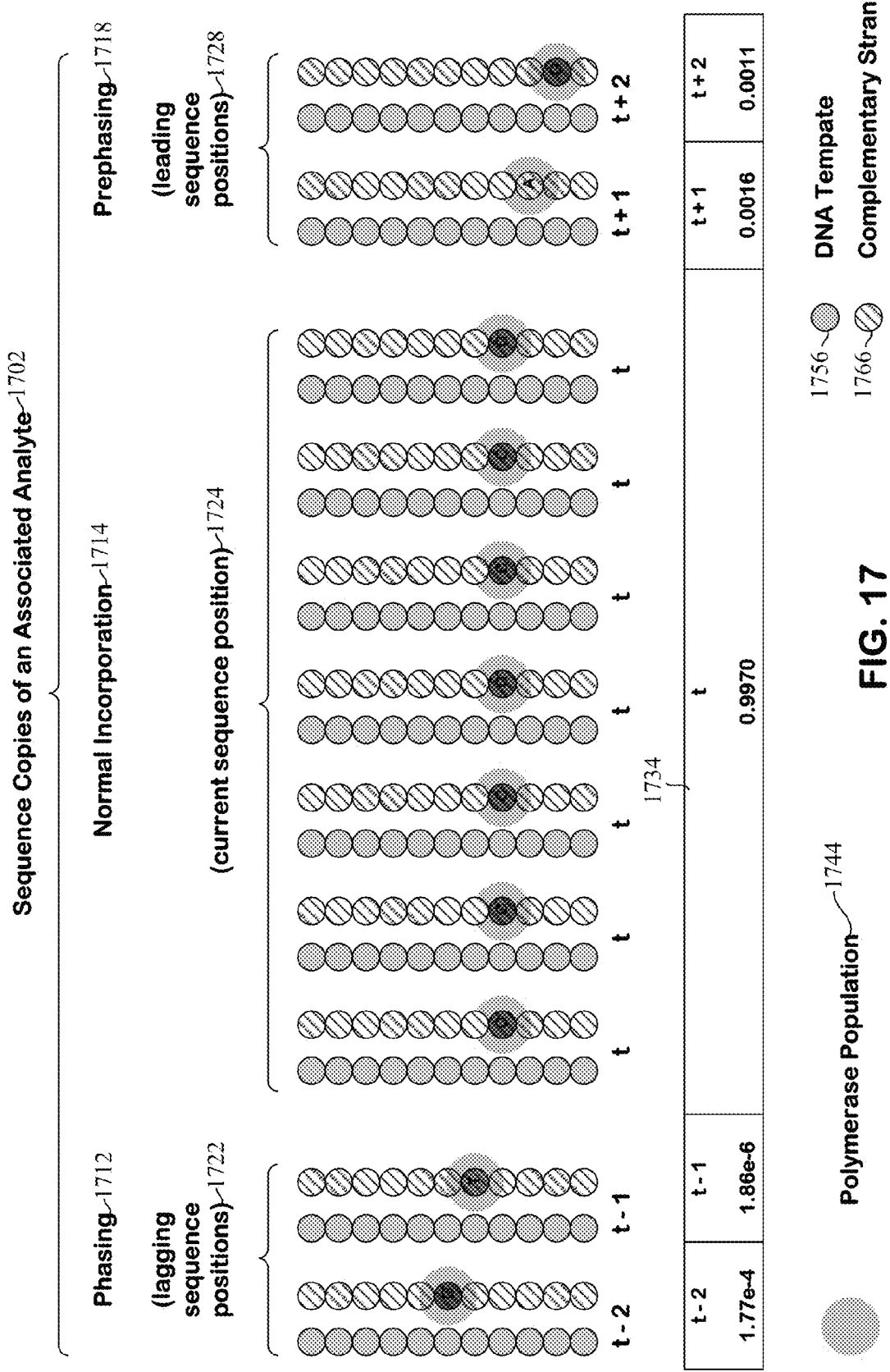
FIG. 17 shows probability distribution of polymerase population movement in accordance with one implementation.

In the example illustrated in FIG. 17, a majority of the polymerase population 1744 observes a normal incorporation 1714 of base C in a complementary strand 1766 of DNA template 1756. A first minority of the polymerase population 1744 observes prephasing 1718 at a first successive sequencing cycle (t+1, base A) and at a second successive sequencing cycle (t+2, base G) in the complementary strand 1766 of the DNA template 1756. A second minority of the polymerase population 1744 observes the phasing 1712 at a first preceding sequencing cycle (t−1, base G) and at a second preceding sequencing cycle (t−2, base T) in the complementary strand 1766 of the DNA template 1756.

FIG. 17 also shows an example 1734 of the probability distribution of the polymerase population movement 1700. The probability distribution sums to one. Other examples of probability distribution are 0.0017, 0.9970, 0.0012 (three cycles); 0.0017, 0.9972, 0.0011 (three cycles); and 3.70e-4, 1.28e-4, 8.04e-5, 9.77e-8, 1.05e-7, 1.22e-4, 1.57e-6, 1.67e-3, 9.96e-1, 1.04e-3 (ten cycles).

The phasing and prephasing data 1800 is generated by transposed convolution 3500 using one or more convolution kernels. FIG. 18 shows one example of generating the phasing and prephasing data 1800 using a convolution kernel 1802. The convolution kernel 1802 has three weights/coefficients a, b, c, which are learned during the training. In FIG. 18, the polynomials represented by alphabets a, b, c are for illustration purposes and, in operation, are numbers resulting from the transposed convolution 3500.

In one implementation, for the first sequencing cycle (cycle 1), an initial probability distribution 1804 of the polymerase population movement assumes that all of the polymerase population 1744 is at a first sequence position, i.e., [1, 0, 0, 0, . . . ]. This way, the initial probability distribution 1804 is preset to specify that, at the first sequencing cycle, the polymerase population movement is limited to the first sequence position.

In another implementation, for the first sequencing cycle (cycle 1), the initial probability distribution 1804 of the polymerase population movement includes position-specific parameters (a) 1806. The position-specific parameters (a) 1806 start from the first sequence position and span one or more successive sequence positions. They are learned during the training to account for the polymerase population movement extending beyond the first sequence position at the first sequencing cycle.

Beginning with the initial probability distribution 1804 of the polymerase population movement as starting input, the phasing and prephasing data 1800 is determined by transposed convolution 3500 of the convolution kernel 1802 with a probability distribution of the polymerase population movement at a preceding sequencing cycle (t−1). In one implementation, the transposed convolution 3500 is applied recurrently or repeatedly 1816 until a probability distribution for each of the k sequencing cycles is generated.

For example, the probability distribution 1814 at cycle 2 is produced as a result of transposed convolution 3500 between the convolution kernel 1802 and the initial probability distribution 1804 at cycle 1; the probability distribution 1824 at cycle 3 is produced as a result of transposed convolution 3500 between the convolution kernel 1802 and the probability distribution 1814 at cycle 2; the probability distribution 1834 at cycle 4 is produced as a result of transposed convolution 3500 between the convolution kernel 1802 and the probability distribution 1824 at cycle 3; and the probability distribution 1844 at cycle 5 is produced as a result of transposed convolution 3500 between the convolution kernel 1802 and the probability distribution 1834 at cycle 4. In one implementation, SAME or zero padding is used when the convolution kernel 1802 transposedly convolves over the initial probability distribution 1804.

In one implementation, the transposed convolution 3500 produces a k×k phasing and prephasing matrix 1800 in which: (i) the rows respectively denote the k sequencing cycles and (ii) the columns also respectively denote the k sequencing cycles. Each row represents the probability distribution of the polymerase population at the corresponding sequencing cycle. Each column specifies the probability of the polymerase population being at a corresponding current sequencing cycle or at a flanking sequencing cycle.

Figure 35:
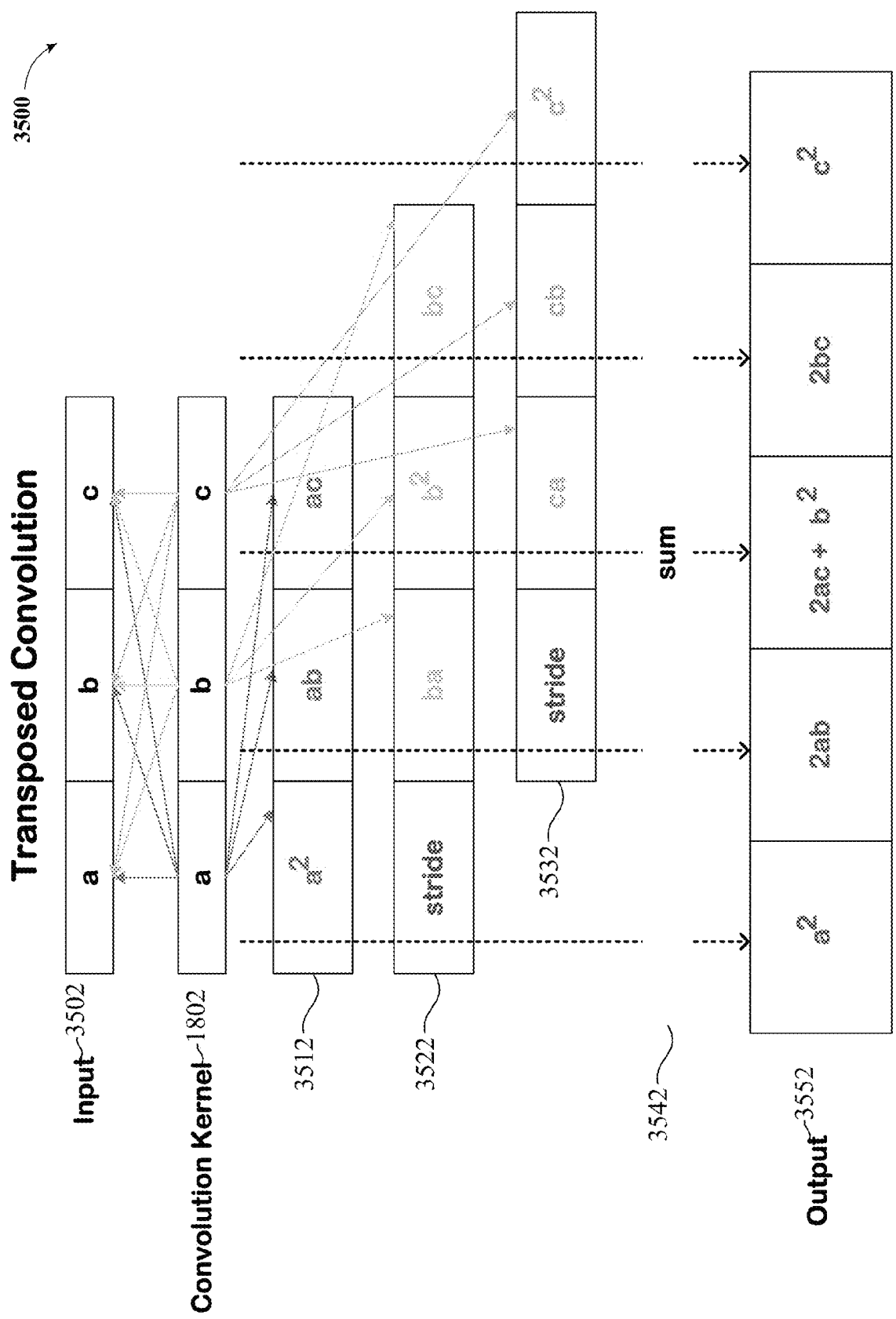
FIG. 35 depicts one example of transposed convolution.

FIG. 35 shows one example of how the transposed convolution 3500 is used to calculate the probability distribution as output 3552. The example uses one stride and sums 3542 the intermediate outputs 3512, 3522, 3532 at overlapping positions. The intermediate outputs 3512, 3522, 3532 are calculated by multiplying each element of the convolution kernel 1802 with each element of input 3502. In one implementation, the transposed convolution 3500 is operationalized by the transposed convolution operator 2619, which can be part of the neural network-based base caller 2614.

In some implementations, m convolution kernels are used to generate the phasing and prephasing data 1800 and the weights/coefficients of the m convolution kernels are learned during the training. That is, each of the m convolution kernels is used to generate a respective k×k phasing and prephasing matrix by use of recurrent transposed convolution. Accordingly, the phasing and prephasing data 1800 comprises m phasing and prephasing channels 2606 determined for the current sequencing cycle (t) from corresponding convolution kernels in the m convolution kernels.

A phasing and prephasing channel for a corresponding current sequencing cycle includes a subset of elements (also called "window-of-interest") from a row of a k×k phasing and prephasing matrix generated by a convolution kernel. The row represents the probability distribution of the polymerase population at the corresponding current sequencing cycle.

The window-of-interest comprises as many elements as the number of sequencing cycles for which the image data is used as input. The window-of-interest is centered at a probability value for the corresponding current sequencing cycle and includes left and right flanking probability values for the left and right flanking sequencing cycles. For example, if the image data is for three sequencing cycles: a current sequencing cycle (t), a successive/right flanking sequencing cycle (t+1), and a preceding/left flanking sequencing cycle (t−1), then the window-of-interest includes three elements.

In one implementation, the phasing and prephasing data 1800 is generated by a phasing, prephasing data generator 2630, which can be part of the neural network-based base caller 2614.

Base Context Data

The base context data 1900, 2000 identifies: (i) bases called in one or more preceding sequencing cycles and (ii) base call possibilities in the current sequencing cycle and the successive sequencing cycles. In one implementation, the base context data 1900, 2000 identifies the bases called and the base call possibilities using a base encoding that represents each base by assigning a value for each of the imaged channels. In one implementation, the base context data 1900, 2000 identifies the base call possibilities using an r-input truth table, with r representing a count of the current sequencing cycle and the successive sequencing cycles.

FIG. 19 shows the base context data 1900 for three sequencing cycles: a current sequencing cycle (i), a previous sequencing cycle (i−1), and a future sequencing cycle (i+1). The base context data 1900 is generated for a red channel 1912 and a green channel 1922. Within the respective channels, the known base call prediction components for the previous sequencing cycle (i−1) are kept fixed. The base call 1902 in the previous sequencing cycle (i−1) was C, with a 0 base call prediction component in the red channel 1912 and a 1 base call prediction component in the green channel 1922.

Then, a truth table-style encoding is used to list the base call possibilities for the current sequencing cycle (i) and the future sequencing cycle (i+1). Here, r, the count of the current and future sequencing cycles is 2, so a 2-input truth table is generated to produce $2^2=4$ binary values in each of the red and green channels 1912, 1922.

Then, the base context data 1900 for the red and green channels 1912, 1922 is row-wise concatenated to produce the respective base context channels 2607.

FIG. 20 shows the base context data 2000 for five sequencing cycles: a current sequencing cycle (i), a first previous sequencing cycle (i−1), a second previous sequencing cycle (i−2), a first future sequencing cycle (i+1), and a second future sequencing cycle (i+2). The base context data 1900 is generated for a red channel 2012 and a green channel 2022. Within the respective channels, the known base call prediction components for the first previous sequencing cycle (i−1) and the second previous sequencing cycle (i−2) are kept fixed. The base call 2002 in the first previous sequencing cycle (i−1) was C, with a 0 base call prediction component in the red channel 2012 and a 1 base call prediction component in the green channel 2022. The base call 2004 in the second previous sequencing cycle (i−2) was A, with a 1 base call prediction component in the red channel 2012 and a 0 base call prediction component in the green channel 2022.

Then, the truth table-style encoding is used to list the base call possibilities for the current sequencing cycle (i), the first future sequencing cycle (i+1), and the second future sequencing cycle (i+2). Here, r, the count of the current and future sequencing cycles is 3, so a 3-input truth table is generated to produce $2^3=8$ binary values in each of the red and green channels 2012, 2022.

Then, the base context data 2000 for the red and green channels 2012, 2022 is row-wise concatenated to produce the respective base context channels 2607.

In one implementation, the base context data 1900, 2000 is generated by a base context data generator 2631, which can be part of the neural network-based base caller 2614.

Note that, like the phasing and prephasing channels, the base context channels also include as many elements as the number of sequencing cycles for which the image data is used as input, as discussed above.

Compact Convolution-Based Base Calling Example 1—Three Cycles

The compact convolution-based base calling 2100 uses image data for three sequencing cycles per timestep/convolution window/sequencing cycle to predict a base call on a cycle-by-cycle basis. The base call prediction from one previous timestep/convolution window/sequencing cycle is used to create the base context data 1900 for a current timestep/convolution window/sequencing cycle. The base context data 1900 identifies the base call possibilities for the current sequencing cycle and one future sequencing cycle (r=2). The probability distribution of the polymerase population movement in the previous sequencing cycle is used to create the phasing and prephasing data (window-of-interest with three elements) for the current timestep/convolution window/sequencing cycle. In one implementation, data from a previous timestep/convolution window/sequencing cycle is provided to a next timestep/convolution window/sequencing cycle by a data propagator 2624.

Figure 21:
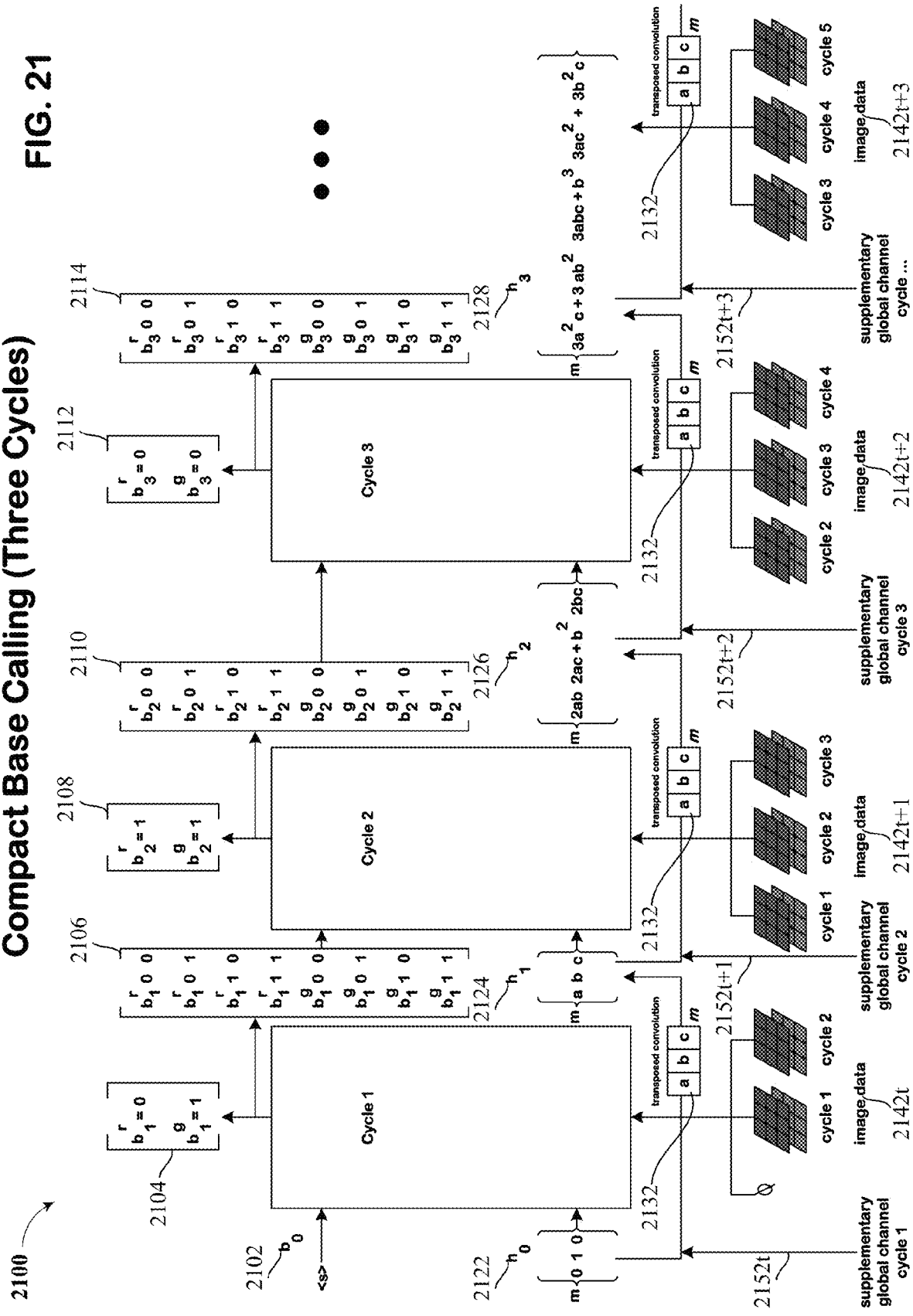
FIG. 21 depicts one example of the compact convolution-based base calling using image data for three cycles.

In FIG. 21, at sequencing cycle 1, the image data 2142*t* comprises per-cycle image patches for sequencing cycle 1 and sequencing cycle 2, along with SAME or zero padding. The phasing and prephasing data (h0) 2122 for sequencing cycle 1 comprises initial probability distribution of the polymerase population movement for m convolution kernels. The previous base call (b0) 2102, i.e., the base context data, is set to be a starting value or token (<s>) that is learned during training. After certain convolution operations (discussed in FIG. 23) over the image data 2142*t*, the base context data 1900, and the phasing and prephasing data, a base call prediction 2104 is made for sequencing cycle 1.

Then, the base call prediction 2104 made for sequencing cycle 1 is used to prepare the base context data 2106 for sequencing cycle 2, as discussed above. Also, the phasing and prephasing data (h0) 2122 for sequencing cycle 1 is used to prepare the phasing and prephasing data (h1) 2124 for sequencing cycle 2 by use of transposed convolution 2132 with m convolution kernels, as discussed above. Note that the phasing and prephasing data for each of the sequencing cycles can be prepared in advance by generating the k×k phasing and prephasing matrix using the transposed convolution 2132 with m convolution kernels, as discussed above. In one implementation, each of the m convolution kernels are kept fixed across the timesteps/convolution windows/sequencing cycles.

For sequencing cycle 2, the image data 2142$t$+1 comprises per-cycle image patches for sequencing cycle 1, sequencing cycle 2, and sequencing cycle 3. The image data 2142$t$+1, the base context data 2106, and the phasing and prephasing data (h1) 2124 are used to produce a base call prediction 2108 for sequencing cycle 2.

Then, the base call prediction 2108 made for sequencing cycle 2 is used to prepare the base context data 2110 for sequencing cycle 3, as discussed above. Also, the phasing and prephasing data (h1) 2124 for sequencing cycle 2 is used to prepare the phasing and prephasing data (h2) 2126 for sequencing cycle 3 by use of the transposed convolution 2132 with m convolution kernels, as discussed above.

For sequencing cycle 3, the image data 2142$t$+2 comprises per-cycle image patches for sequencing cycle 2, sequencing cycle 3, and sequencing cycle 4. The image data 2142$t$+2, the base context data 2110, and the phasing and prephasing data (h2) 2126 are used to produce a base call prediction 2112 for sequencing cycle 3.

Then, the base call prediction 2112 made for sequencing cycle 3 is used to prepare the base context data 2114 for sequencing cycle 4, as discussed above. Also, the phasing and prephasing data (h2) 2126 for sequencing cycle 3 is used to prepare the phasing and prephasing data (h3) 2128 for sequencing cycle 4 by use of the transposed convolution 2132 with m convolution kernels, as discussed above.

For sequencing cycle 4, the image data 2142$t$+3 comprises per-cycle image patches for sequencing cycle 3, sequencing cycle 4, and sequencing cycle 5. The image data 2142$t$+3, the base context data 2114, and the phasing and prephasing data (h3) 2128 are used to produce a base call prediction for sequencing cycle 4.

The compact convolution-based base calling 2100 sequentially outputs the base call at each successive convolution window and base calls the associated analytes at each of the sequencing cycles.

Global Channels

In some implementations, at each timestep/convolution window/sequencing cycle, per-cycle, tile-wide global channels 2152$t$, 2152$t$+1, 2152$t$+2, and 2152$t$+3 are respectively fed. The per-cycle, tile-wide global channels 2601 are determined by a global channel calculator 2626. The per-cycle, tile-wide global channels 2601 are determined using singular value decomposition (SVD) of image data features in image data of a plurality of associated analytes disposed on a tile of a flow cell. In other implementations, other techniques of principal component analysis (PCA), such as covariance matrix determination, can be used.

A per-cycle, tile-wide global channel includes a set of principal components of the image data features in image data obtained at a corresponding sequencing cycle from the associated analytes disposed across the tile. The image data features include at least one of background, spatial crosstalk, phasing and prephasing effect, emission overlap, signal intensity, and intensity decay. In some implementations, the per-cycle, tile-wide global channels 2601 are fed as supplemental input to convolution windows of corresponding sequencing cycles. In one implementation, the image data used to generate the per-cycle, tile-wide global channels is obtained from a variety of flow cells, sequencing instruments, sequencing runs, sequencing protocols, sequencing chemistries, sequencing reagents, and analyte densities. In one implementation, the image data is obtained from tile and flow cell data 2609 produced by a sequencer 2628.

Compact Convolution-Based Base Calling Example 2—Five Cycles

The compact convolution-based base calling 2200 uses image data for five sequencing cycles per timestep/convolution window/sequencing cycle to predict a base call on a cycle-by-cycle basis. The base call prediction from two previous timesteps/convolution windows/sequencing cycles are used to create the base context data 2000 for a current timestep/convolution window/sequencing cycle. The base context data 2000 identifies the base call possibilities for the current sequencing cycle and two future sequencing cycles (r=3). The probability distribution of the polymerase population movement in the previous sequencing cycle is used to create the phasing and prephasing data (window-of-interest with five elements) for the current timestep/convolution window/sequencing cycle.

Figure 22:
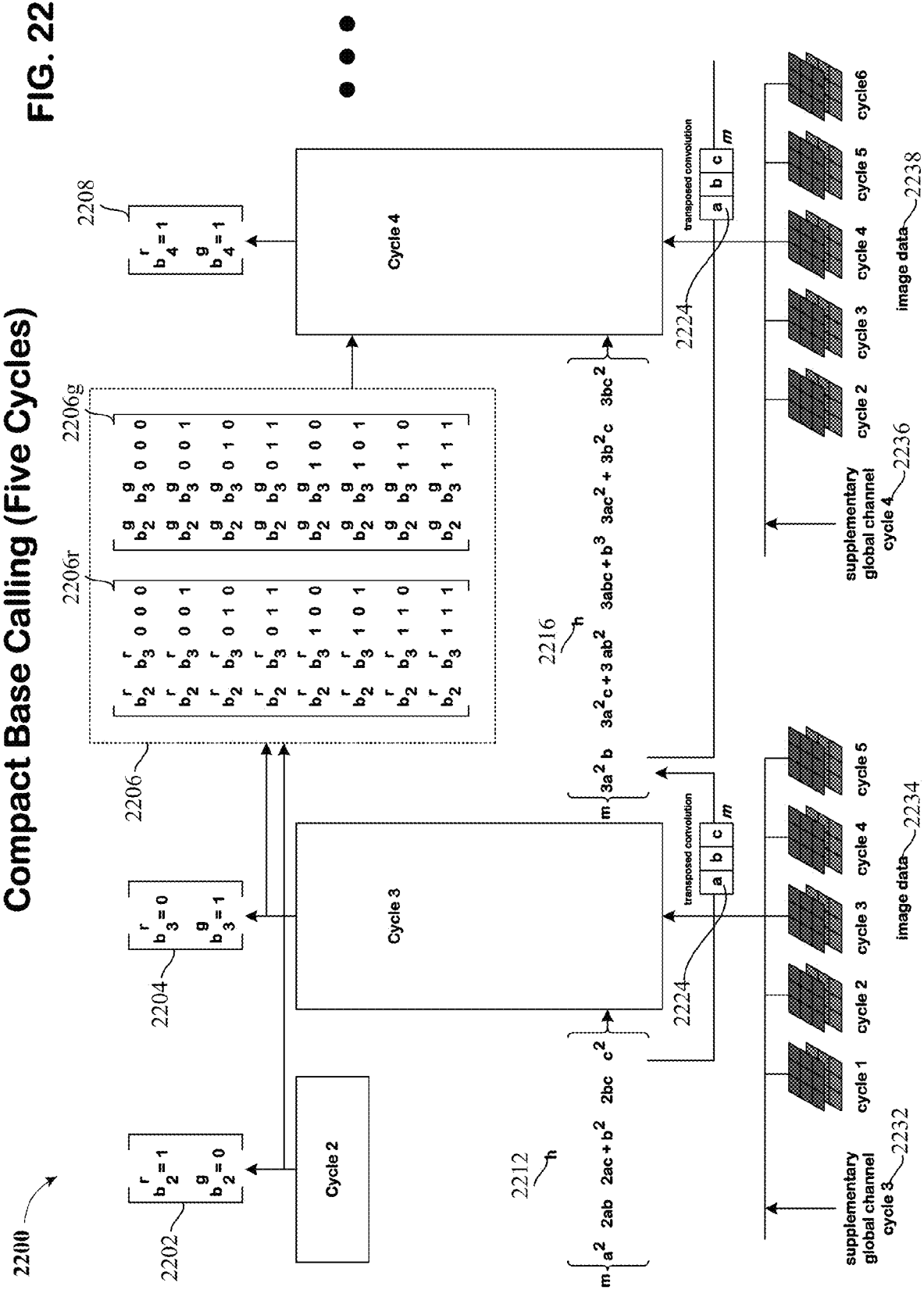
FIG. 22 depicts another example of the compact convolution-based base calling using image data for five cycles.

In FIG. 22, at sequencing cycle 3, the image data 2234 comprises per-cycle image patches for sequencing cycles 1, 2, 3, 4, and 5. The phasing and prephasing data for sequencing cycle 2 (not shown) is used to prepare the phasing and prephasing data 2212 for sequencing cycle 3 by use of transposed convolution 2224 with m convolution kernels, as discussed above. In one implementation, each of the m convolution kernels are kept fixed across the timesteps/convolution windows/sequencing cycles.

The base context data 2000 for sequencing cycle 3 is constructed using the base call made at sequencing cycle 1, the base call 2202 made at sequencing cycle 2, the base call possibility at sequencing cycle 3, the base call possibility at sequencing cycle 4, and the base call possibility at sequencing cycle 5. After certain convolution operations (discussed in FIG. 23) over the image data 2234, the base context data 2000, and the phasing and prephasing data 2212, a base call prediction 2204 is made for sequencing cycle 3.

For sequencing cycle 4, the image data 2238 comprises per-cycle image patches for sequencing cycles 2, 3, 4, 5, and 6. The phasing and prephasing data 2212 for sequencing cycle 3 is used to prepare the phasing and prephasing data 2216 for sequencing cycle 4 by use of transposed convolution 2224 with m convolution kernels, as discussed above. The base context data 2206 (with red and green base context channels 2206$4$, 2206$g$) for sequencing cycle 4 is constructed using the base call 2202 made at sequencing cycle 2, the base call 2204 made at sequencing cycle 3, the base call possibility at sequencing cycle 4, the base call possibility at sequencing cycle 5, and the base call possibility at sequencing cycle 6.

After certain convolution operations (discussed in FIG. 23) over the image data 2238, the base context data 2206, and the phasing and prephasing data 2216, a base call prediction 2208 is made for sequencing cycle 4. Also, supplementary per-cycle supplementary global channels 2232, 2236 are also fed as input to the respective timestep/convolution window/sequencing cycle.

The compact convolution-based base calling 2200 sequentially outputs the base call at each successive convolution window and base calls the associated analytes at each of the sequencing cycles.

Convolutions in a Timestep/Convolution Window

Figure 23:
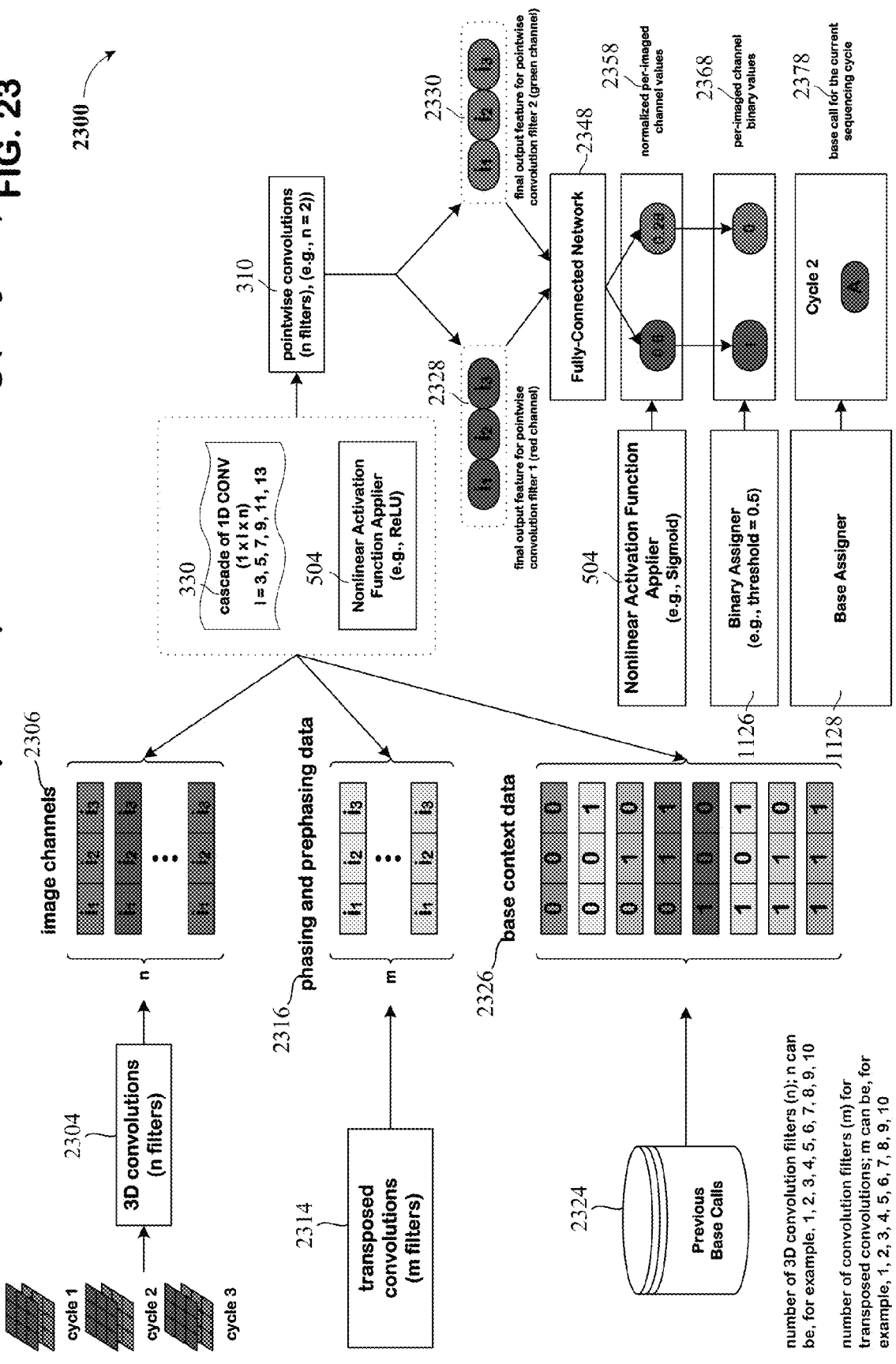
FIG. 23 shows one implementation of the convolutions used to mix the image data, the phasing and prephasing data, and the base context data for the compact convolution-based base calling in a timestep/convolution window/sequencing cycle.

FIG. 23 shows one implementation of the convolutions used to mix the image data 2302, the phasing and prephasing data 2316, and the base context data 2326 for the compact convolution-based base calling 2100, 2200 in a timestep/ convolution window/sequencing cycle. 3D convolutions 2304 are applied on the image data 2302 to produce the image channels 2306, as discussed above. Transposed convolutions 2314 are used to generate the phasing and prephasing data 2316 with the phasing and prephasing channels, as discussed above. Previous base calls 2324 are used to generate the base context data 2326 with base context channels.

The image channels 2306, the phasing and prephasing data 2316, and the base context data 2326 are then mixed using the cascade of 1D convolutions 330 and the pointwise convolutions 310 to produce the final output features 2328, 2330. The final output features 2328, 2330 are fed to a fully-connected network 2348. The fully-connected network 2348 produces unnormalized per-imaged channel values, which are converted to normalized per-imaged channel values 2358 by the nonlinear activation function applier 504. The normalized per-imaged channel values 2358 are then converted to per-imaged channel binary values 2368 by the binary assigner 1126. The per-imaged channel binary values 2368 are used by the base assigner 1128 to produce the base call 2378 for the current sequencing cycle.

Pull-Push/Push-Pull Convolutions

Figure 24:
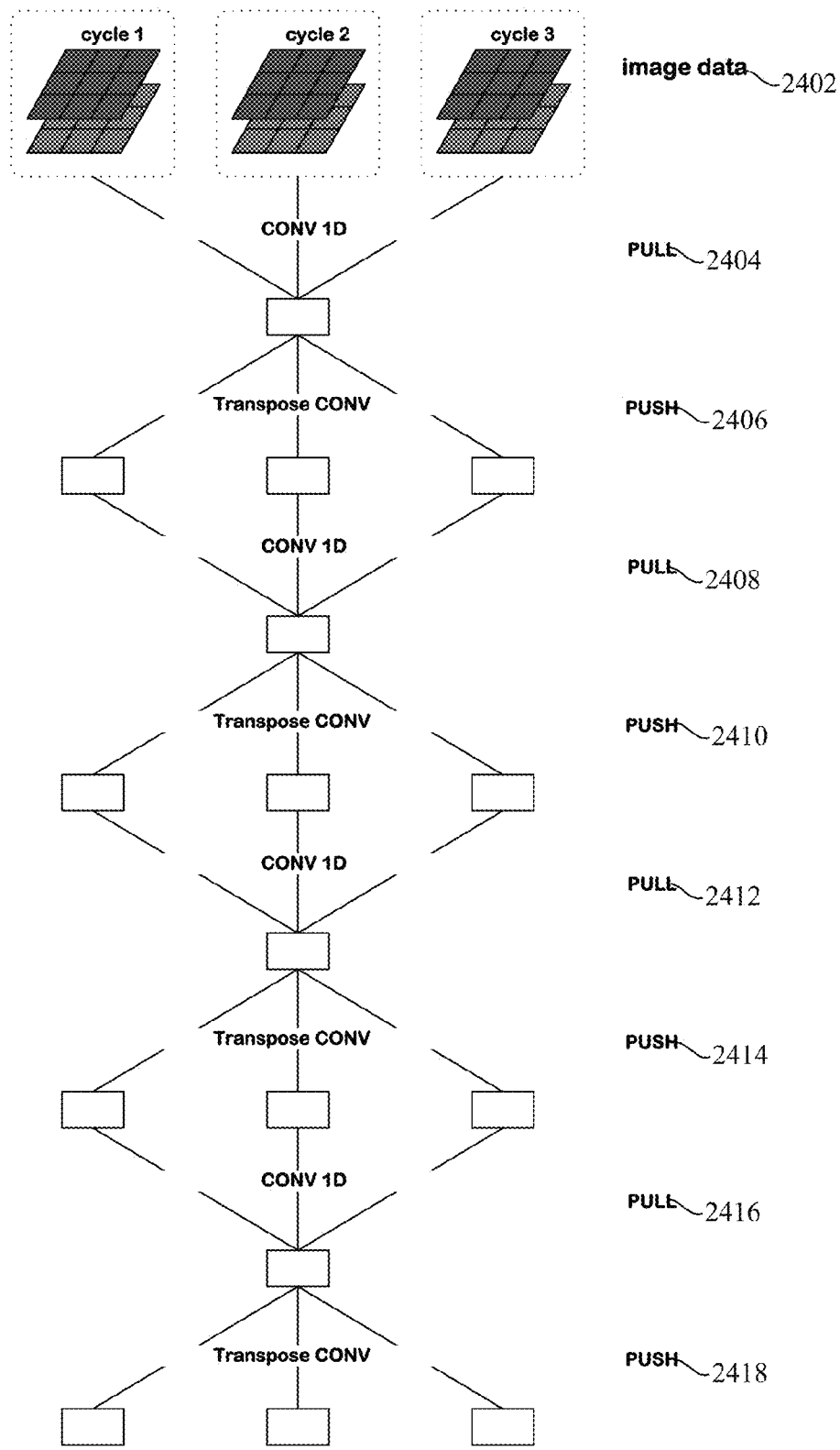
FIG. 24 shows one implementation of pull-push and push-pull convolutions in which a combination of the 1D convolutions and transposed convolutions is used for the compact convolution-based base calling.

FIG. 24 shows one implementation of pull-push and push-pull convolutions in which a combination 2400 of the 1D convolutions (pull) 2404, 2408, 2412, 2416 and transposed convolutions (pull) 2406, 2410, 2414, 2418 is used for the compact convolution-based base calling 2100, 2200. The combination 2400 alternates between application of the 1D convolutions and the transposed convolutions on the image data 2402.

In one implementation, a different bank of 3D convolution filters is used in each timestep/convolution window/sequencing cycle. Each bank includes one to ten 3D convolution filters.

CPU Inference

Figure 25:
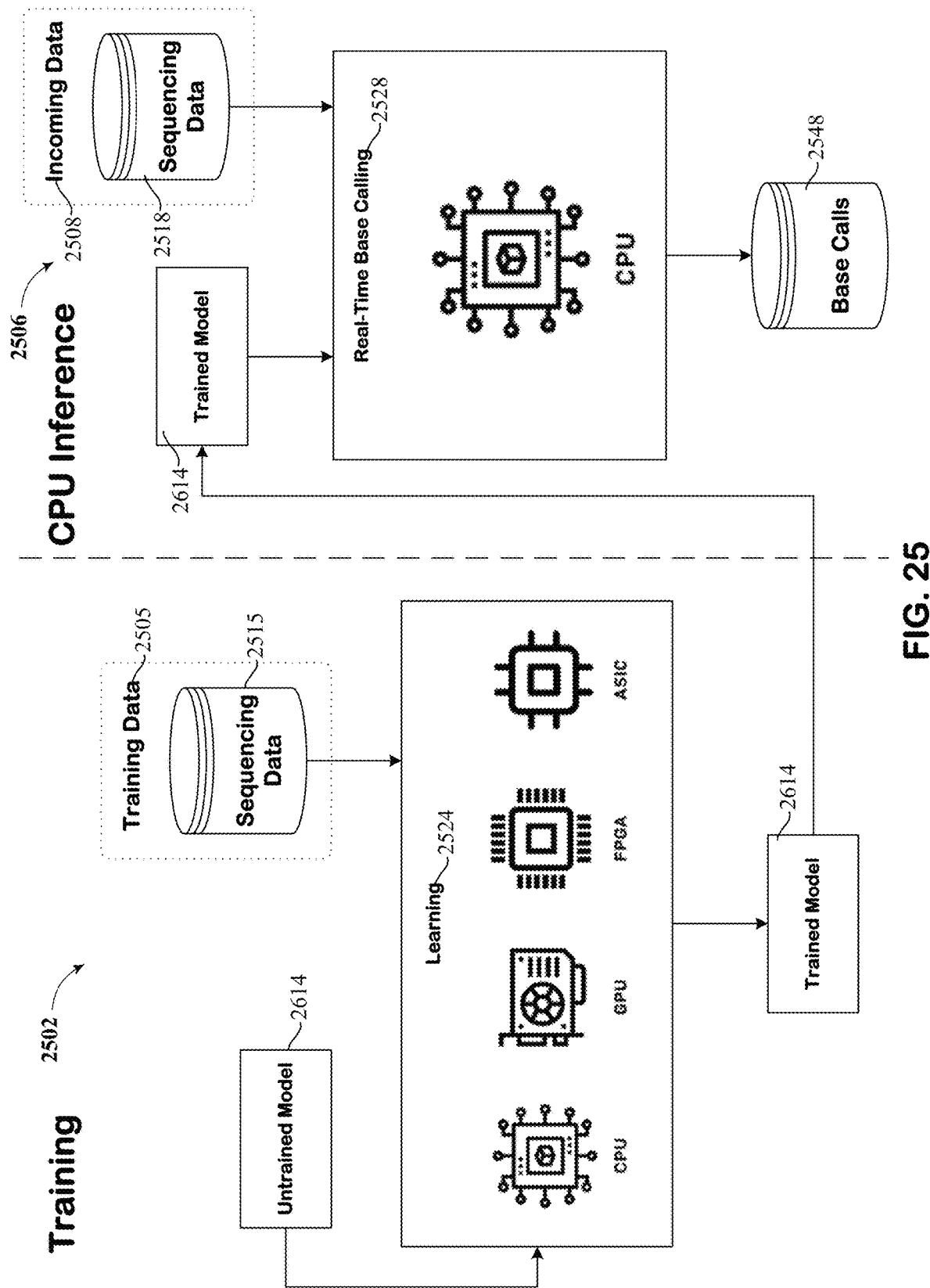
FIG. 25 depicts one implementation of performing the compact convolution-based base calling during inference on a central processing unit (CPU) by using image data from only a subset of the sequencing cycles.

FIG. 25 depicts one implementation of performing the compact convolution-based base calling during inference 2506 on a central processing unit (CPU) by using image data from only a subset of the sequencing cycles. In particular, the inference 2506 is performed using the per-cycle image patch for the current sequencing cycle, the per-cycle image patches for the one or more successive sequencing cycles, and the per-cycle image patches for the one or more preceding sequencing cycles. During training 2502, the neural network-based base caller 2614 is trained on training data 2505, which in turn comprises sequencing data 2515. The untrained model 2614 can be trained on CPU, GPU, FPGA, ASIC, and/or CGRA to produce the trained model 2614.

During inference 2506, the trained model 2614 runs on the CPU and performs real-time base calling 2528 on incoming data 2508 that comprises sequencing data 2518 and produce base calls 2548. Inference 2506 is operationalized by a tester 2629.

System Modules and Data Stores

Figure 26:
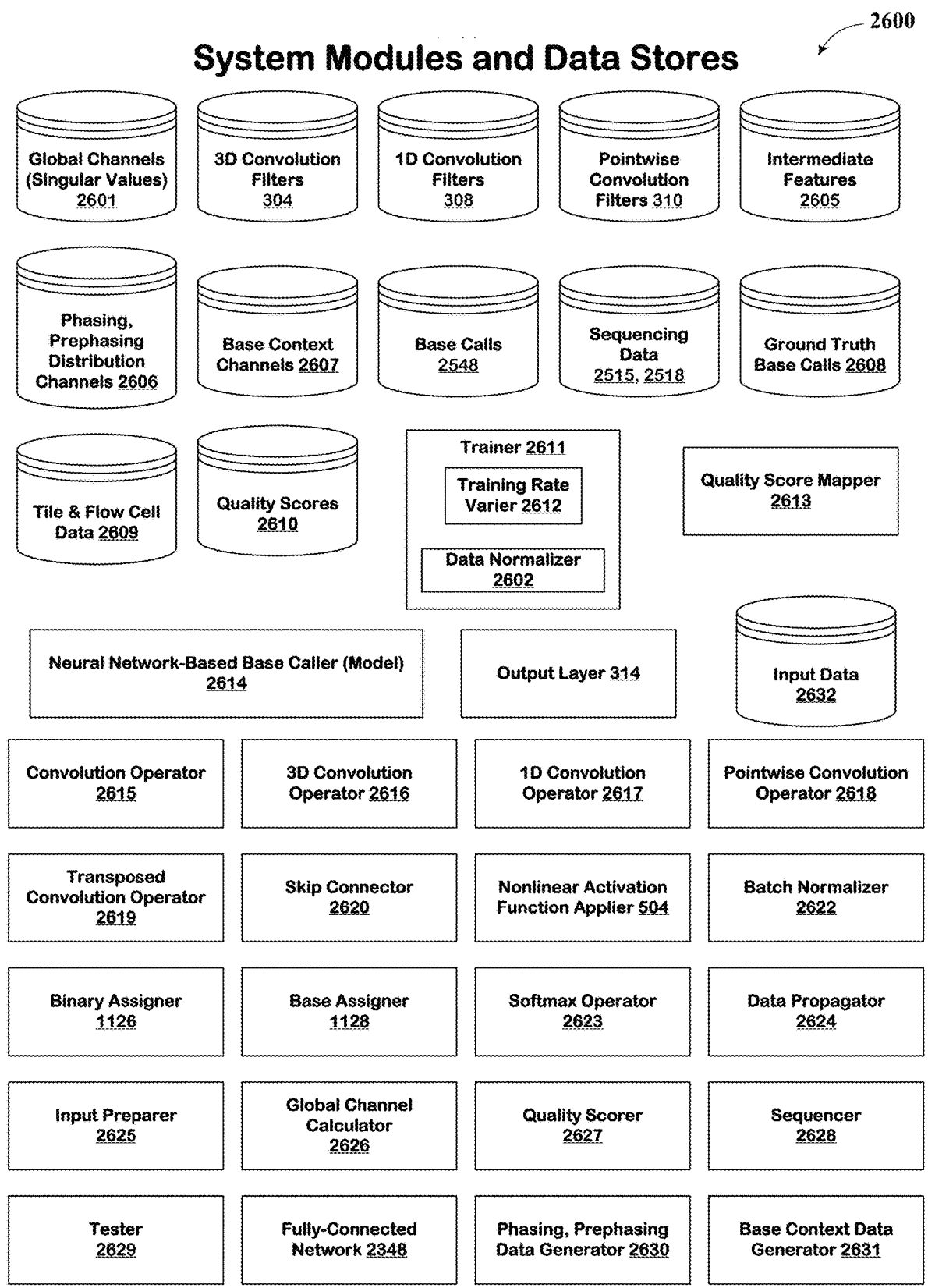
FIG. 26 is a block diagram that shows various system modules and data stores used for the convolution-based base calling and the compact convolution-based base calling in accordance with one implementation.

FIG. 26 is a block diagram 2600 that shows various system modules and data stores used for the convolution-based base calling and the compact convolution-based base calling in accordance with one implementation.

The modules in this application can be implemented in hardware or software, and need not be divided up in precisely the same blocks as shown in the figures. Some can also be implemented on different processors or computers, or spread among a number of different processors or computers. In addition, it will be appreciated that some of the modules can be combined, operated in parallel or in a different sequence than that shown in the figures without affecting the functions achieved. Also as used herein, the term "module" can include "sub-modules," which themselves can be considered herein to constitute modules. The blocks in the figures designated as modules can also be thought of as flowchart steps in a method.

Sequencing data 2515, 2518 is produced by a sequencing instrument or sequencer 2628 (e.g., Illumina's Firefly, iSeq, HiSeqX, HiSeq3000, HiSeq4000, HiSeq2500, NovaSeq 6000, NextSeq, NextSeqDx, MiSeq and MiSeqDx). The following discussion outlines one implementation of how the sequencing data 2515, 2518 is generated and what it depicts.

Base calling is the process in which the raw signal of the sequencer 2628, i.e., intensity data extracted from images, is decoded into DNA sequences and quality scores. In one implementation, the Illumina platforms employ cyclic reversible termination (CRT) chemistry for base calling. The process relies on growing nascent DNA strands complementary to template DNA strands with modified nucleotides, while tracking the emitted signal of each newly added nucleotide. The modified nucleotides have a 3' removable block that anchors a fluorophore signal of the nucleotide type.

Sequencing occurs in repetitive cycles, each comprising three steps: (a) extension of a nascent strand by adding a modified nucleotide; (b) excitation of the fluorophores using one or more lasers of the optical system and imaging through different filters of the optical system, yielding sequencing images; and (c) cleavage of the fluorophores and removal of the 3' block in preparation for the next sequencing cycle. Incorporation and imaging cycles are repeated up to a designated number of sequencing cycles, defining the read length of all clusters. Using this approach, each cycle interrogates a new position along the template strands.

The tremendous power of the Illumina platforms stems from their ability to simultaneously execute and sense millions or even billions clusters undergoing CRT reactions. The sequencing process occurs in a flow cell—a small glass slide that holds the input DNA fragments during the sequencing process. The flow cell is connected to the high-throughput optical system, which comprises microscopic imaging, excitation lasers, and fluorescence filters. The flow cell comprises multiple chambers called lanes. The lanes are physically separated from each other and may contain different tagged sequencing libraries, distinguishable without sample cross contamination. The imaging device (e.g., a solid-state imager such as a charge-coupled device (CCD) or a complementary metal-oxide-semiconductor (CMOS) sensor) takes snapshots at multiple locations along the lanes in a series of non-overlapping regions called tiles.

For example, there are hundred tiles per lane in Illumina Genome Analyzer II and sixty-eight tiles per lane in Illumina HiSeq2000. A tile holds hundreds of thousands to millions of clusters. A cluster comprises approximately one thousand identical copies of a template molecule, though clusters vary in size and shape. The clusters are grown from the template molecule, prior to the sequencing run, by bridge amplification of the input library. The purpose of the amplification and cluster growth is to increase the intensity of the emitted signal since the imaging device cannot reliably sense a single fluorophore. However, the physical distance of the DNA fragments within a cluster is small, so the imaging device perceives the cluster of fragments as a single spot.

The output of a sequencing run is the sequencing images, each depicting intensity emissions of clusters on the tile in the pixel domain for a specific combination of lane, tile, sequencing cycle, and fluorophore.

Computer System

Figure 36:
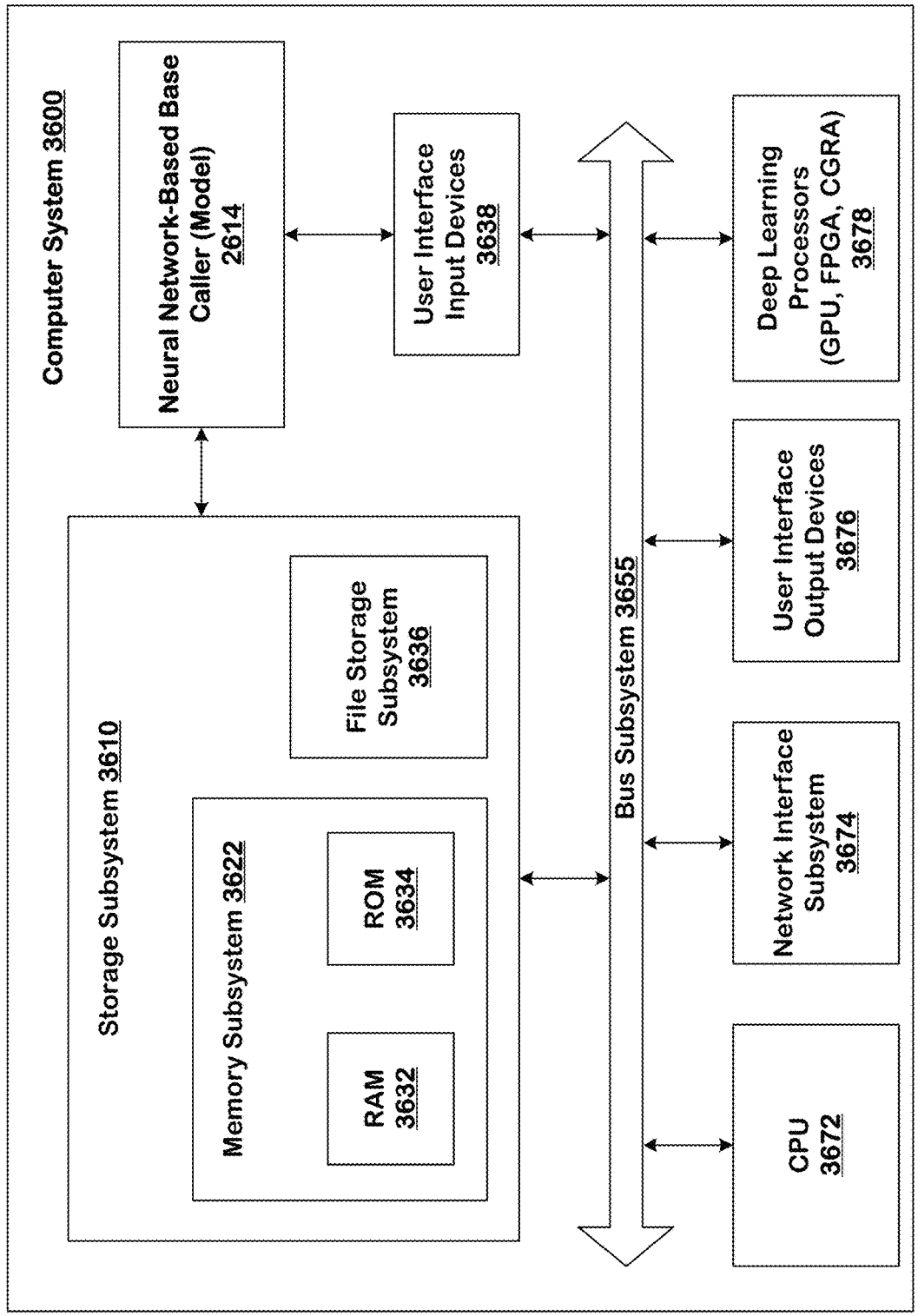
FIG. 36 is a computer system that can be used to implement the convolution-based base calling and the compact convolution-based base calling disclosed herein.

FIG. 36 is a computer system 3600 that can be used to implement the convolution-based base calling and the compact convolution-based base calling disclosed herein. Computer system 3600 includes at least one central processing unit (CPU) 3672 that communicates with a number of peripheral devices via bus subsystem 3655. These peripheral devices can include a storage subsystem 3610 including, for example, memory devices and a file storage subsystem 3636, user interface input devices 3638, user interface output devices 3676, and a network interface subsystem 3674. The input and output devices allow user interaction with computer system 3600. Network interface subsystem 3674 provides an interface to outside networks, including an interface to corresponding interface devices in other computer systems.

In one implementation, the neural network-based base caller 2614 is communicably linked to the storage subsystem 3610 and the user interface input devices 3638.

User interface input devices 3638 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 3600.

User interface output devices 3676 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 3600 to the user or to another machine or computer system.

Storage subsystem 3610 stores programming and data constructs that provide the functionality of some or all of the modules and methods described herein. These software modules are generally executed by deep learning processors 3678.

Deep learning processors 3678 can be graphics processing units (GPUs), field-programmable gate arrays (FPGAs), application-specific integrated circuits (ASICs), and/or coarse-grained reconfigurable architectures (CGRAs). Deep learning processors 3678 can be hosted by a deep learning cloud platform such as Google Cloud Platform™, Xilinx™, and Cirrascale™. Examples of deep learning processors 3678 include Google's Tensor Processing Unit (TPU)™, rackmount solutions like GX4 Rackmount Series™, GX36 Rackmount Series™ NVIDIA DGX-1™, Microsoft' Stratix V FPGA™, Graphcore' s Intelligent Processor Unit (IPU) ™, Qualcomm's Zeroth Platform™ with Snapdragon processors™, NVIDIA's Volta™ NVIDIA's DRIVE PX™, NVIDIA's JETSON TX1/TX2 MODULE™, Intel's Nirvana™ Movidius VPU™, Fujitsu DPI™, ARM's DynamicIQ™, IBM TrueNorth™, and others.

Memory subsystem 3622 used in the storage subsystem 3610 can include a number of memories including a main random access memory (RAM) 3632 for storage of instructions and data during program execution and a read only memory (ROM) 3636 in which fixed instructions are stored.

A file storage subsystem 3636 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 3636 in the storage subsystem 3610, or in other machines accessible by the processor.

Bus subsystem 3655 provides a mechanism for letting the various components and subsystems of computer system 3600 communicate with each other as intended. Although bus subsystem 3655 is shown schematically as a single bus, alternative implementations of the bus subsystem can use multiple busses.

Computer system 3600 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 3600 depicted in FIG. 36 is intended only as a specific example for purposes of illustrating the preferred implementations of the present invention. Many other configurations of computer system 3600 are possible having more or less components than the computer system depicted in FIG. 36.

Particular Implementations

We describe various implementations of convolution-based base calling. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

Convolution-Based Base Calling

In one implementation, we disclose a neural network-implemented method of base calling analytes. The method includes accessing a sequence of per-cycle image patches generated for a series of sequencing cycles of a sequencing run. The pixels in the per-cycle image patches contain intensity data for associated analytes. The intensity data is obtained for one or more imaged channels by corresponding light sensors configured to detect emissions from the associated analytes.

The method includes applying three-dimensional (3D) convolutions on the sequence of per-cycle image patches on a sliding convolution window basis. In a convolution window, a 3D convolution filter convolves over: (i) a plurality of the per-cycle image patches along a temporal dimension and detects and accounts for phasing and prephasing effect between successive ones of the sequencing cycles caused by asynchronous readout of sequence copies of an associated analyte, (ii) a plurality of pixels in each of the per-cycle image patches along spatial dimensions and detects and accounts for spatial crosstalk between adjacent analytes caused by detection of emissions from a non-associated analyte by a corresponding light sensor of an associated analyte, and (iii) each of the imaged channels along a depth dimension and detects and accounts for emission overlap between the imaged channels caused by overlap of dye emission spectra and produces at least one output feature as a result of convolving over the sequence of per-cycle image patches on the sliding convolution window basis.

The method includes supplementing output features produced as a result of a plurality of 3D convolution filters convolving over the sequence of per-cycle image patches with imaged channel-specific and cross-cycle intensity data features of one or more of the pixels that contain the intensity data for one or more of the associated analytes to be base called.

The method includes beginning with the output features supplemented with the intensity data features as starting input, applying a cascade of one-dimensional (1D) convolutions and producing further output features, the cascade using 1D convolutions with different receptive fields and detecting varying degrees of the asynchronous readout caused by the phasing and prephasing effect.

The method includes applying pointwise convolutions on the further output features and producing final output features.

The method includes processing the final output features through an output layer and producing base calls for the associated analytes at each of the sequencing cycles.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in these implementations can readily be combined with sets of base features identified in other implementations.

For an associated analyte to be base called, the method includes producing a final output feature for each of the imaged channels, normalizing unnormalized per-cycle values in final output features of the imaged channels, converting the normalized per-cycle values into per-cycle binary values based on a threshold, and base calling the associated analyte at each of the sequencing cycles based on the per-cycle binary values at corresponding positions in the final output features.

In one implementation, the output layer comprises a sigmoid function that squashes the unnormalized per-cycle values in the final output features between zero and one. In such an implementation, the method includes assigning those squashed per-cycle values that are below the threshold a zero value and assigning those squashed per-cycle values that are above the threshold a one value.

In one implementation, the output layer comprises a softmax function that produces an exponentially normalized probability distribution of a base incorporated at a sequencing cycle in an associated analyte to be base called being A, C, T, and G. In such an implementation, the method includes classifying the base as A, C, T, or G based on the distribution.

In one implementation, the method includes the 3D convolutions separately applying a respective convolution kernel on each of the imaged channels and producing at least one intermediate output feature for each of the imaged channels, the 3D convolutions further combining intermediate output features of the imaged channels and producing output features, wherein the output features represent information mixed between the imaged channels, and beginning with the output features supplemented with the intensity data features as starting input, applying the cascade of 1D convolutions.

In one implementation, the method includes the 3D convolutions separately applying a respective convolution kernel on each of the imaged channels and producing at least one intermediate output feature for each of the imaged channels, the 3D convolutions further combining intermediate output features of the imaged channels and producing output features, wherein the output features represent information mixed between the imaged channels, and beginning with the output features supplemented with the intensity data features as starting input, applying a plurality of cascade of 1D convolutions such that each cascade in the plurality corresponds to one of the imaged channels and operates on the input independent of another cascade.

In one implementation, the method includes the 3D convolutions separately applying a respective convolution kernel on each of the imaged channels and producing at least one intermediate output feature for each of the imaged channels, the 3D convolutions not combining intermediate output features of the imaged channels and instead making them available as imaged channel-specific output features, supplementing the imaged channel-specific output features with cross-cycle intensity data features from the corresponding imaged channel of one or more of the pixels that contain the intensity data for one or more of the associated analytes to be base called, and beginning with the imaged channel-specific output features supplemented with the intensity data features as starting input, applying the cascade of 1D convolutions.

In one implementation, the method includes the 3D convolutions separately applying a respective convolution kernel on each of the imaged channels and producing at least one intermediate output feature for each of the imaged channels, the 3D convolutions not combining intermediate output features of the imaged channels and instead making them available as imaged channel-specific output features, supplementing the imaged channel-specific output features with cross-cycle intensity data features from the corresponding imaged channel of one or more of the pixels that contain the intensity data for one or more of the associated analytes to be base called, and beginning with the imaged channel-specific output features supplemented with the intensity data features as starting input, applying a plurality of cascade of 1D convolutions such that each cascade in the plurality corresponds to one of the imaged channels and operates on the input independent of another cascade.

In one implementation, the method includes the 1D convolutions mixing information between respective per-cycle elements of each of the output features and the intensity data features on a sliding window basis and producing at least one intermediate output feature for each of the output features and the intensity data features, and the 1D convolutions accumulating information across intermediate output features of the output features on a per-cycle element basis and producing further output features. In some implementations, size of the sliding window is based on a receptive field of the 1D convolutions and varies in the cascade.

In one implementation, the method includes applying a combination of the 1D convolutions and transposed convolutions instead of the cascade of 1D convolutions, wherein the combination alternates between application of the 1D convolutions and the transposed convolutions.

In one implementation, the method includes the pointwise convolutions respectively convolving over further output features on a per-cycle element basis and producing at least one intermediate output feature for each of the further output features, and the pointwise convolutions accumulating information across intermediate output features of the further output features on a per-cycle element basis and producing at least one final output feature.

In one implementation, the method includes using the normalized per-cycle values in the final output features of the imaged channels to assign quality scores to base call predictions emitted by the output layer based on a quality score mapping. The quality score mapping is determined by calculating predicted error rates for base call predictions made on training data and determining corresponding predicted quality scores, determining a fit between the predicted quality scores and empirical quality scores determined from empirical base calling error rates derived from test data, and correlating the predicted quality scores to the empirical quality scores based on the fit.

In one implementation, the method includes learning kernel weights of convolution filters applied by the 3D convolutions, the 1D convolutions, and the pointwise convolutions using a backpropagation-based gradient update technique during training that progressively matches the base call predictions emitted by the output layer with ground truth 2608. In one implementation, the training is operationalized by the trainer 2611.

In one implementation, the ground truth includes per-cycle binary values for each of the imaged channels. In such an implementation, the method includes the backpropagation-based gradient update technique computing an error between the per-cycle binary values in the ground truth 2608 and the corresponding per-cycle binary values in the final output features of the imaged channels.

In one implementation, the ground truth includes a one-hot encoding identifying a correct base. In such an implementation, the method includes the backpropagation-based gradient update technique computing an error between the one-hot encoding in the ground truth 2608 and the exponentially normalized probability distribution produced by the softmax function.

In one implementation, the method includes varying a learning rate of the learning, which is operationalized by a training rate varier 2612. In one implementation, the method includes extracting the per-cycle image patches from respective per-cycle images of a tile of a flow cell on which the analytes are disposed. In one implementation, the training data 2505 (which comprises sequencing data 2515, 2518) is normalized using z-scores by a data normalizer 2602.

In one implementation, the method includes base calling analytes disposed throughout the tile by extracting per-cycle image patches from overlapping regions of the tile such that the extracted per-cycle image patches have overlapping pixels. In one implementation, the 1D convolutions use bilinear form product to mix information.

In one implementation, the method includes applying non-linear activations functions on the output features and producing activated output features for processing by the 1D convolutions. In one implementation, the method includes applying non-linear activations functions on the further output features and producing activated further output features for processing by the pointwise convolutions. In one implementation, the method includes using batch normalization along with the 1D convolutions. In one implementation, the method includes using batch normalization along with the pointwise convolutions. In one implementation, the method includes using a plurality of 1D convolution filters in each 1D convolution in the cascade.

In one implementation, the method includes including using a plurality of pointwise convolution filters in the pointwise convolutions such that each pointwise convolution filter in the plurality corresponds to one of the imaged channels and operates on the further output features independent of another pointwise convolution filter. In one implementation, the 3D convolutions, the 1D convolutions, and the pointwise convolutions use SAME padding. In one implementation, the method includes the 3D convolution filter convolving over the sequence of per-cycle image patches to detect and account for signal decay due to fading.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In another implementation, we disclose a neural network-implemented method of base calling analytes. The method includes accessing a sequence of per-cycle image patches generated for a series of sequencing cycles of a sequencing run. Each pixel in the per-cycle image patches is associated with an analyte. The per-cycle image patches are centered at a center pixel that contains intensity data for a target associated analyte. Non-center pixels in the per-cycle image patches contain intensity data for associated analytes adjacent to the target associated analyte. The intensity data is obtained for one or more imaged channels.

The method includes applying three-dimensional (3D) convolutions on the sequence of per-cycle image patches on a sliding convolution window basis. In a convolution window, a 3D convolution filter convolves over: (i) a plurality of the per-cycle image patches along a temporal dimension and detects and accounts for phasing and prephasing effect in a current sequencing cycle from one or more successive sequencing cycles and one or more preceding sequencing cycles due to asynchronous readout of sequence copies of an associated analyte, (ii) the center pixel and the non-center pixels along spatial dimensions and detects and accounts for spatial crosstalk from the non-center pixels in the center pixel due to detection of emissions from the adjacent associated analytes by a corresponding light sensor of the target associated analyte, and (iii) each of the imaged channels along a depth dimension and detects and accounts for emission overlap between the imaged channels due to overlap of dye emission spectra, and produces at least one output feature as a result of convolving over the sequence of per-cycle image patches on the sliding convolution window basis.

The method includes supplementing output features produced as a result of a plurality of 3D convolution filters convolving over the sequence of per-cycle image patches with imaged channel-specific and cross-cycle intensity data features of the center pixel.

The method includes beginning with the output features supplemented with the intensity data features as starting input, applying a cascade of one-dimensional (1D) convolutions and producing further output features, the cascade using 1D convolutions with different receptive fields and detecting varying degrees of the asynchronous readout caused by the phasing and prephasing effect.

The method includes applying pointwise convolutions on the further output features and producing final output features.

The method includes processing the final output features through an output layer and producing an output.

The method includes base calling the target associated analyte at each of the sequencing cycles based on the output.

In yet another implementation, we disclose a neural network-implemented method of base calling analytes. The method includes accessing a sequence of per-cycle image patches generated for a series of sequencing cycles of a sequencing run. Pixels in the per-cycle image patches contain intensity data for associated analytes in one or more imaged channels.

The method includes applying three-dimensional (3D) convolutions on the sequence of per-cycle image patches on a sliding convolution window basis such that, in a convolution window, a 3D convolution filter convolves over a plurality of the per-cycle image patches and produces at least one output feature as a result of convolving over the sequence of per-cycle image patches on the sliding convolution window basis.

The method includes beginning with output features produced by the 3D convolutions as starting input, applying further convolutions and producing final output features.

The method includes processing the final output features through an output layer and producing base calls for one or more of the associated analytes to be base called at each of the sequencing cycles.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Compact Convolution-Based Base Calling

In one implementation, we disclose a neural network-implemented method of base calling analytes. The method includes accessing a sequence of per-cycle image patches generated for a series of sequencing cycles of a sequencing run. The pixels in the per-cycle image patches contain intensity data for associated analytes. The intensity data is obtained for one or more imaged channels by corresponding light sensors configured to detect emissions from the associated analytes.

The method includes processing the sequence of per-cycle image patches on a sliding convolution window basis such that, in a convolution window, using as input image data comprising a per-cycle image patch for a current sequencing cycle, per-cycle image patches for one or more successive sequencing cycles, and per-cycle image patches for one or more preceding sequencing cycles, phasing and prephasing data representing probability distribution of polymerase population movement across sequence copies of an associated analyte for a current sequence position corresponding to the current sequence cycle, leading sequence positions corresponding to the successive sequencing cycles, and lagging sequence positions corresponding to the preceding sequencing cycles, and base context data identifying bases called in one or more preceding sequencing cycles and base call possibilities in the current sequencing cycle and the successive sequencing cycles, and producing, as output, a base call for the current sequencing cycle and for one or more of the associated analytes to be base called.

The method includes sequentially outputting the base call at each successive convolution window and base calling the associated analytes at each of the sequencing cycles.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in these implementations can readily be combined with sets of base features identified in other implementations.

In one implementation, the phasing and prephasing data comprises phasing and prephasing channels determined for the current sequencing cycle from corresponding convolution filters in a plurality of convolution kernels. In one implementation, a phasing and prephasing channel is determined for the current sequencing cycle from a corresponding convolution filter by beginning with an initial probability distribution of the polymerase population movement at a first sequencing cycle as starting input and determining successive probability distributions of the polymerase population movement at successive sequencing cycles as a result of transposed convolution of the corresponding convolution kernel with a probability distribution of the polymerase population movement at a preceding sequencing cycle, selecting from a probability distribution of the polymerase population movement at the current sequencing cycle those values that occur at the current sequence position, the leading sequence positions, and the lagging sequence positions, and including the selected values in the phasing and prephasing channel.

In one implementation, the initial probability distribution is preset to specify that, at the first sequencing cycle, the polymerase population movement is limited to a first sequence position. In one implementation, the initial probability distribution includes position-specific parameters which, starting from the first sequence position, span one or more successive sequence positions and are learned during training to account for the polymerase population movement extending beyond the first sequence position at the first sequencing cycle.

In one implementation, the base context data identifies the bases called and the base call possibilities using a base encoding that represents each base by assigning a value for each of the imaged channels. In one implementation, the base context data identifies the base call possibilities using an r-input truth table, with r representing a count of the current sequencing cycle and the successive sequencing cycles in the convolution window.

In one implementation, the method includes, in the convolution window, processing the image data through a plurality of three-dimensional (3D) convolution filters and producing, as output, a plurality of image channels, beginning with the image channels, the phasing and prephasing data, and the base context data as starting input, applying a cascade of one-dimensional (1D) convolutions and producing further output features, and applying pointwise convolutions on the further output features and producing final output features, and processing the final output features through an output layer and producing the base call for the current sequencing cycle and for the associated analytes.

In one implementation, the method includes using a different plurality of 3D convolution filters in each convolution window. In one implementation, the method includes using bilinear form product to mix the image channels, the phasing and prephasing data, and the base context data.

In one implementation, a 3D convolution filter convolves over a plurality of the per-cycle image patches along a temporal dimension and detects and accounts for phasing and prephasing effect between successive ones of the sequencing cycles caused by asynchronous readout of sequence copies of an associated analyte, a plurality of pixels in each of the per-cycle image patches along spatial dimensions and detects and accounts for spatial crosstalk between adjacent analytes caused by detection of emissions from a non-associated analyte by a corresponding light sensor of an associated analyte, and each of the imaged channels along a depth dimension and detects and accounts for emission overlap between the imaged channels caused by overlap of dye emission spectra, and produces at least one image channel as a result of convolving over the sequence of per-cycle image patches.

In one implementation, the 1D convolutions use different receptive fields and detect varying degrees of the asynchronous readout. In one implementation, the method includes supplementing the image channels with imaged channel-specific and current cycle-specific intensity data features of one or more of the pixels that contain the intensity data for the associated analytes.

In one implementation, the method includes applying a combination of the 1D convolutions and transposed convolutions instead of the cascade of 1D convolutions. The combination alternates between application of the 1D convolutions and the transposed convolutions. In one implementation, the method includes, for an associated analyte to be base called, producing a final output feature for each of the imaged channels, and in the output layer, processing the final output features through a fully-connected network and producing unnormalized per-imaged channel values, normalizing the unnormalized per-imaged channel values, converting the normalized per-imaged channel values into per-imaged channel binary values based on a threshold, and producing the base call for the current sequencing cycle and for the associated analyte based on the per-imaged channel binary values.

In one implementation, the output layer comprises a sigmoid function that squashes the unnormalized per-imaged channel values in the final output features between zero and one. In this implementation, the method includes assigning those squashed per-imaged channel values that are below the threshold a zero value and assigning those squashed per-imaged channel values that are above the threshold a one value.

In one implementation, the output layer comprises a softmax function that produces an exponentially normalized probability distribution of the base call being A, C, T, and G. In such this implementation, the method includes classifying the base call as A, C, T, or G based on the distribution.

In one implementation, the method includes determining per-cycle, tile-wide global channels using singular value decomposition (SVD) of image data features in image data of a plurality of associated analytes disposed on a tile of a flow cell. A per-cycle, tile-wide global channel includes a set of principal components of the image data features in image data obtained at a corresponding sequencing cycle from the associated analytes disposed across the tile.

In one implementation, the image data features include at least one of background, spatial crosstalk, phasing and prephasing effect, emission overlap, signal intensity, and intensity decay. In one implementation, the method includes feeding the per-cycle, tile-wide global channels as supplemental input to convolution windows of corresponding sequencing cycles.

In one implementation, the image data used to generate the per-cycle, tile-wide global channels is obtained from a variety of flow cells, sequencing instruments, sequencing runs, sequencing protocols, sequencing chemistries, sequencing reagents, and analyte densities. In one implementation, the method includes performing the base calling during inference on a central processing unit (CPU) by only using the per-cycle image patch for the current sequencing cycle, the per-cycle image patches for the one or more successive sequencing cycles, and the per-cycle image patches for the one or more preceding sequencing cycles and generating a base call for the current sequencing cycle.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Terminology

As used herein, the term "analyte" is intended to mean a point or area in a pattern that can be distinguished from other points or areas according to relative location. An individual analyte can include one or more molecules of a particular type. For example, an analyte can include a single target nucleic acid molecule having a particular sequence or an analyte can include several nucleic acid molecules having the same sequence (and/or complementary sequence, thereof). Different molecules that are at different analytes of a pattern can be differentiated from each other according to the locations of the analytes in the pattern. Example analytes include without limitation, wells in a substrate, beads (or other particles) in or on a substrate, projections from a substrate, ridges on a substrate, pads of gel material on a substrate, or channels in a substrate.

Any of a variety of target analytes that are to be detected, characterized, or identified can be used in an apparatus, system or method set forth herein. Exemplary analytes include, but are not limited to, nucleic acids (e.g., DNA, RNA or analogs thereof), proteins, polysaccharides, cells, antibodies, epitopes, receptors, ligands, enzymes (e.g. kinases, phosphatases or polymerases), small molecule drug candidates, cells, viruses, organisms, or the like.

The terms "analyte," "nucleic acid," "nucleic acid molecule," and "polynucleotide" are used interchangeably herein. In various implementations, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain implementations include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other implementations, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular implementations, a nucleic acid may have one or more detectable labels, as described elsewhere herein.

The terms "analyte," "cluster," "nucleic acid cluster," "nucleic acid colony," and "DNA cluster" are used interchangeably and refer to a plurality of copies of a nucleic acid template and/or complements thereof attached to a solid support. Typically and in certain preferred implementations, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

Colonies of nucleic acids can also be referred to as "nucleic acid clusters". Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 μm to about 6 μm, about 0.3 μm to about 4 μm, about 0.4 μm to about 3 μm, about 0.5 μm to about 2 μm, about 0.75 μm to about 1.5 μm, or any intervening diameter. In a particular implementation, the diameter of a nucleic acid cluster is about 0.5 μm, about 1 μm, about 1.5 μm, about 2 μm, about 2.5 μm, about 3 μm, about 4 μm, about 5 μm, or about 6 μm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, $100,000/mm^2$ to $1,000,000/mm^2$ and $1,000,000/mm^2$ to $10,000,000/mm^2$.

As used herein, an "analyte" is an area of interest within a specimen or field of view. When used in connection with microarray devices or other molecular analytical devices, an analyte refers to the area occupied by similar or identical molecules. For example, an analyte can be an amplified oligonucleotide or any other group of a polynucleotide or polypeptide with a same or similar sequence. In other implementations, an analyte can be any element or group of elements that occupy a physical area on a specimen. For example, an analyte could be a parcel of land, a body of water or the like. When an analyte is imaged, each analyte will have some area. Thus, in many implementations, an analyte is not merely one pixel.

The distances between analytes can be described in any number of ways. In some implementations, the distances between analytes can be described from the center of one analyte to the center of another analyte. In other implementations, the distances can be described from the edge of one analyte to the edge of another analyte, or between the outer-most identifiable points of each analyte. The edge of an analyte can be described as the theoretical or actual physical boundary on a chip, or some point inside the boundary of the analyte. In other implementations, the distances can be described in relation to a fixed point on the specimen or in the image of the specimen.

Generally several implementations will be described herein with respect to a method of analysis. It will be understood that systems are also provided for carrying out the methods in an automated or semi-automated way. Accordingly, this disclosure provides neural network-based template generation and base calling systems, wherein the systems can include a processor; a storage device; and a program for image analysis, the program including instructions for carrying out one or more of the methods set forth herein. Accordingly, the methods set forth herein can be carried out on a computer, for example, having components set forth herein or otherwise known in the art.

The methods and systems set forth herein are useful for analyzing any of a variety of objects. Particularly useful objects are solid supports or solid-phase surfaces with attached analytes. The methods and systems set forth herein provide advantages when used with objects having a repeating pattern of analytes in an xy plane. An example is a microarray having an attached collection of cells, viruses, nucleic acids, proteins, antibodies, carbohydrates, small molecules (such as drug candidates), biologically active molecules or other analytes of interest.

An increasing number of applications have been developed for arrays with analytes having biological molecules such as nucleic acids and polypeptides. Such microarrays typically include deoxyribonucleic acid (DNA) or ribonucleic acid (RNA) probes. These are specific for nucleotide sequences present in humans and other organisms. In certain applications, for example, individual DNA or RNA probes can be attached at individual analytes of an array. A test sample, such as from a known person or organism, can be exposed to the array, such that target nucleic acids (e.g., gene fragments, mRNA, or amplicons thereof) hybridize to complementary probes at respective analytes in the array. The probes can be labeled in a target specific process (e.g., due to labels present on the target nucleic acids or due to enzymatic labeling of the probes or targets that are present in hybridized form at the analytes). The array can then be examined by scanning specific frequencies of light over the analytes to identify which target nucleic acids are present in the sample.

Biological microarrays may be used for genetic sequencing and similar applications. In general, genetic sequencing comprises determining the order of nucleotides in a length of target nucleic acid, such as a fragment of DNA or RNA. Relatively short sequences are typically sequenced at each analyte, and the resulting sequence information may be used in various bioinformatics methods to logically fit the sequence fragments together so as to reliably determine the sequence of much more extensive lengths of genetic material from which the fragments were derived. Automated, computer-based algorithms for characteristic fragments have been developed, and have been used more recently in genome mapping, identification of genes and their function, and so forth. Microarrays are particularly useful for characterizing genomic content because a large number of variants are present and this supplants the alternative of performing many experiments on individual probes and targets. The microarray is an ideal format for performing such investigations in a practical manner.

Any of a variety of analyte arrays (also referred to as "microarrays") known in the art can be used in a method or system set forth herein. A typical array contains analytes, each having an individual probe or a population of probes. In the latter case, the population of probes at each analyte is typically homogenous having a single species of probe. For example, in the case of a nucleic acid array, each analyte can have multiple nucleic acid molecules each having a common sequence. However, in some implementations the populations at each analyte of an array can be heterogeneous. Similarly, protein arrays can have analytes with a single protein or a population of proteins typically, but not always, having the same amino acid sequence. The probes can be attached to the surface of an array for example, via covalent linkage of the probes to the surface or via non-covalent interaction(s) of the probes with the surface. In some implementations, probes, such as nucleic acid molecules, can be attached to a surface via a gel layer as described, for example, in U.S. patent application Ser. No. 13/784,368 and US Pat. App. Pub. No. 2011/0059865 A1, each of which is incorporated herein by reference.

Example arrays include, without limitation, a BeadChip Array available from Illumina, Inc. (San Diego, Calif.) or others such as those where probes are attached to beads that are present on a surface (e.g. beads in wells on a surface) such as those described in U.S. Pat. No. 6,266,459; 6,355,431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in a method or system according to some implementations of the present disclosure. An example spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; WO 91/06678; WO 07/123744; U.S. Pat. No. 7,329,492; 7,211,414; 7,315,019; 7,405,281, or 7,057,026; or US Pat. App. Pub. No. 2008/0108082 A1, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US Pat. App. Pub. No. 2005/0130173 or US Pat. App. Pub. No. 2005/0064460, each of which is incorporated herein by reference in its entirety.

Arrays used for nucleic acid sequencing often have random spatial patterns of nucleic acid analytes. For example, HiSeq or MiSeq sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Example patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The analytes of such patterned arrays can be used to capture a single nucleic acid template molecule to seed subsequent formation of a homogenous colony, for example, via bridge amplification. Such patterned arrays are particularly useful for nucleic acid sequencing applications.

The size of an analyte on an array (or other object used in a method or system herein) can be selected to suit a particular application. For example, in some implementations, an analyte of an array can have a size that accommodates only a single nucleic acid molecule. A surface having a plurality of analytes in this size range is useful for constructing an array of molecules for detection at single molecule resolution. Analytes in this size range are also useful for use in arrays having analytes that each contain a colony of nucleic acid molecules. Thus, the analytes of an array can each have an area that is no larger than about 1 $mm^2$, no larger than about 500 $\mu m^2$, no larger than about 100 $\mu m^2$, no larger than about 10 $\mu m^2$, no larger than about 1 $\mu m^2$, no larger than about 500 $nm^2$, or no larger than about 100 $nm^2$, no larger than about 10 $nm^2$, no larger than about 5 $nm^2$, or no larger than about 1 $nm^2$. Alternatively or additionally, the analytes of an array will be no smaller than about 1 $mm^2$, no smaller than about 500 $\mu m^2$, no smaller than about 100 $\mu m^2$, no smaller than about 10 $\mu m^2$, no smaller than about 1 $\mu m^2$, no smaller than about 500 $nm^2$, no smaller than about 100 $nm^2$, no smaller than about 10 $nm^2$, no smaller than about 5 $nm^2$, or no smaller than about 1 $nm^2$. Indeed, an analyte can have a size that is in a range between an upper and lower limit selected from those exemplified above. Although several size ranges for analytes of a surface have been exemplified with respect to nucleic acids and on the scale of nucleic acids, it will be understood that analytes in these size ranges can be used for applications that do not include nucleic acids. It will be further understood that the size of the analytes need not necessarily be confined to a scale used for nucleic acid applications.

For implementations that include an object having a plurality of analytes, such as an array of analytes, the analytes can be discrete, being separated with spaces between each other. An array useful in the invention can have analytes that are separated by edge to edge distance of at most 100 µm, 50 µm, 10 µm, 5 µm, 1 µm, 0.5 µm or less. Alternatively or additionally, an array can have analytes that are separated by an edge to edge distance of at least 0.5 µm, 1 µm, 5 µm, 50µm, 100 µm or more. These ranges can apply to the average edge to edge spacing for analytes as well as to the minimum or maximum spacing.

In some implementations the analytes of an array need not be discrete and instead neighboring analytes can abut each other. Whether or not the analytes are discrete, the size of the analytes and/or pitch of the analytes can vary such that arrays can have a desired density. For example, the average analyte pitch in a regular pattern can be at most 100 µm, 50 µm, 10 µm, 5 µm, 1 µm, 0.5 µm or less. Alternatively or additionally, the average analyte pitch in a regular pattern can be at least 0.5 µm, 1 µm, 5 µm, 10 µm, 50 µm, 100 µm or more. These ranges can apply to the maximum or minimum pitch for a regular pattern as well. For example, the maximum analyte pitch for a regular pattern can be at most 100 µm, 50 µm, 10 µm, 5 µm, 1 µm 0.5 µm, or less; and/or the minimum analyte pitch in a regular pattern can be at least 0.5 µm, 1 µm, 5 µm, 10 µm, 50 µm, 100 µm, or more.

The density of analytes in an array can also be understood in terms of the number of analytes present per unit area. For example, the average density of analytes for an array can be at least about $1 \times 10^3$ analytes/$mm^2$, $1 \times 10^4$ analytes/$mm^2$, $1 \times 10^5$ analytes/$mm^2$, $1 \times 10^6$ analytes/$mm^2$, $1 \times 10^7$ analytes/ mm², 1×10⁸ analytes/mm², or 1×10⁹ analytes/mm², or higher. Alternatively or additionally the average density of analytes for an array can be at most about 1×10⁹ analytes/mm², 1×10⁸ analytes/mm², 1×10⁷ analytes/mm², 1×10⁶ analytes/mm², 1×10⁵ analytes/mm², 1×10⁴ analytes/mm², or 1×10³ analytes/mm², or less.

The above ranges can apply to all or part of a regular pattern including, for example, all or part of an array of analytes.

The analytes in a pattern can have any of a variety of shapes. For example, when observed in a two dimensional plane, such as on the surface of an array, the analytes can appear rounded, circular, oval, rectangular, square, symmetric, asymmetric, triangular, polygonal, or the like. The analytes can be arranged in a regular repeating pattern including, for example, a hexagonal or rectilinear pattern. A pattern can be selected to achieve a desired level of packing. For example, round analytes are optimally packed in a hexagonal arrangement. Of course other packing arrangements can also be used for round analytes and vice versa.

A pattern can be characterized in terms of the number of analytes that are present in a subset that forms the smallest geometric unit of the pattern. The subset can include, for example, at least about 2, 3, 4, 5, 6, 10 or more analytes. Depending upon the size and density of the analytes the geometric unit can occupy an area of less than 1 mm², 500 μm², 100 μm², 50 μm², 10 μm², 1 μm², 500 nm², 100 nm², 50 nm², 10 nm², or less. Alternatively or additionally, the geometric unit can occupy an area of greater than 10 nm², 50 nm², 100 nm², 500 nm², 1 μm², 10 μm², 50 μm², 100 μm², 500 μm², 1 mm², or more. Characteristics of the analytes in a geometric unit, such as shape, size, pitch and the like, can be selected from those set forth herein more generally with regard to analytes in an array or pattern.

An array having a regular pattern of analytes can be ordered with respect to the relative locations of the analytes but random with respect to one or more other characteristic of each analyte. For example, in the case of a nucleic acid array, the nuclei acid analytes can be ordered with respect to their relative locations but random with respect to one's knowledge of the sequence for the nucleic acid species present at any particular analyte. As a more specific example, nucleic acid arrays formed by seeding a repeating pattern of analytes with template nucleic acids and amplifying the template at each analyte to form copies of the template at the analyte (e.g., via cluster amplification or bridge amplification) will have a regular pattern of nucleic acid analytes but will be random with regard to the distribution of sequences of the nucleic acids across the array. Thus, detection of the presence of nucleic acid material generally on the array can yield a repeating pattern of analytes, whereas sequence specific detection can yield non-repeating distribution of signals across the array.

It will be understood that the description herein of patterns, order, randomness and the like pertain not only to analytes on objects, such as analytes on arrays, but also to analytes in images. As such, patterns, order, randomness and the like can be present in any of a variety of formats that are used to store, manipulate or communicate image data including, but not limited to, a computer readable medium or computer component such as a graphical user interface or other output device.

As used herein, the term "image" is intended to mean a representation of all or part of an object. The representation can be an optically detected reproduction. For example, an image can be obtained from fluorescent, luminescent, scatter, or absorption signals. The part of the object that is present in an image can be the surface or other xy plane of the object. Typically, an image is a 2 dimensional representation, but in some cases information in the image can be derived from 3 or more dimensions. An image need not include optically detected signals. Non-optical signals can be present instead. An image can be provided in a computer readable format or medium such as one or more of those set forth elsewhere herein.

As used herein, "image" refers to a reproduction or representation of at least a portion of a specimen or other object. In some implementations, the reproduction is an optical reproduction, for example, produced by a camera or other optical detector. The reproduction can be a non-optical reproduction, for example, a representation of electrical signals obtained from an array of nanopore analytes or a representation of electrical signals obtained from an ion-sensitive CMOS detector. In particular implementations non-optical reproductions can be excluded from a method or apparatus set forth herein. An image can have a resolution capable of distinguishing analytes of a specimen that are present at any of a variety of spacings including, for example, those that are separated by less than 100 μm, 50 μm, 10 μm, 5 μm, 1 μm or 0.5 μm.

As used herein, "acquiring," "acquisition" and like terms refer to any part of the process of obtaining an image file. In some implementations, data acquisition can include generating an image of a specimen, looking for a signal in a specimen, instructing a detection device to look for or generate an image of a signal, giving instructions for further analysis or transformation of an image file, and any number of transformations or manipulations of an image file.

The invention claimed is:

1. A neural network-implemented method of base calling analytes, the neural network-implemented method including:

accessing a sequence of per-cycle image patches generated for a series of sequencing cycles of a sequencing run, wherein pixels in the per-cycle image patches contain intensity data for associated analytes and the intensity data is obtained for one or more imaged channels by corresponding light sensors configured to detect emissions from the associated analytes;

applying three-dimensional (3D) convolutions on the sequence of per-cycle image patches on a sliding convolution window basis such that, in a convolution window, a 3D convolution filter convolves over a plurality of the per-cycle image patches along a temporal dimension and detects and accounts for phasing and prephasing effect between successive ones of the sequencing cycles caused by asynchronous readout of sequence copies of an associated analyte, a plurality of pixels in each of the per-cycle image patches along spatial dimensions and detects and accounts for spatial crosstalk between adjacent analytes caused by detection of emissions from a non-associated analyte by a corresponding light sensor of an associated analyte, and each of the one or more imaged channels along a depth dimension and detects and accounts for emission overlap between the one or more imaged channels caused by overlap of dye emission spectra, and produces at least one output feature as a result of convolving over the sequence of per-cycle image patches on the sliding convolution window basis;

supplementing output features produced as a result of a plurality of 3D convolution filters convolving over the sequence of per-cycle image patches with
imaged channel-specific and cross-cycle intensity data features of one or more of the pixels that contain the intensity data for one or more of the associated analytes to be base called;
beginning with the output features supplemented with the intensity data features as starting input, applying a cascade of one-dimensional (1D) convolutions and producing further output features, the cascade using 1D convolutions with different receptive fields and detecting varying degrees of the asynchronous readout caused by the phasing and prephasing effect;
applying pointwise convolutions on the further output features and producing final output features; and
processing the final output features through an output layer and producing base calls for the associated analytes at each of the sequencing cycles.

2. The neural network-implemented method of claim 1, further including:
for an associated analyte to be base called,
producing a final output feature for each of the one or more imaged channels;
normalizing unnormalized per-cycle values in the final output features of the one or more imaged channels;
converting the normalized per-cycle values into per-cycle binary values based on a threshold; and
base calling the associated analyte at each of the sequencing cycles based on the per-cycle binary values at corresponding positions in the final output features.

3. The neural network-implemented method of claim 2, wherein the output layer comprises a sigmoid function that squashes the unnormalized per-cycle values in the final output features between zero and one; and
assigning those squashed per-cycle values that are below the threshold a zero value and assigning those squashed per-cycle values that are above the threshold a one value.

4. The neural network-implemented method of claim 1, wherein the output layer comprises a softmax function that produces an exponentially normalized probability distribution of a base incorporated at a sequencing cycle in an associated analyte to be base called being A, C, T, and G; and
classifying the base as A, C, T, or G based on the exponentially normalized probability distribution.

5. The neural network-implemented method of claim 1, further including:
the 3D convolutions separately applying a respective convolution kernel on each of the one or more imaged channels and producing at least one intermediate output feature for each of the one or more imaged channels;
the 3D convolutions further combining intermediate output features of the one or more imaged channels and producing output features, wherein the output features represent information mixed between the one or more imaged channels; and
beginning with the output features supplemented with the intensity data features as starting input, applying the cascade of 1D convolutions.

6. The neural network-implemented method of claim 1, further including:
the 3D convolutions separately applying a respective convolution kernel on each of the one or more imaged channels and producing at least one intermediate output feature for each of the one or more imaged channels;
the 3D convolutions further combining intermediate output features of the one or more imaged channels and producing output features, wherein the output features represent information mixed between the one or more imaged channels; and
beginning with the output features supplemented with the intensity data features as starting input, applying a plurality of cascade of 1D convolutions such that each cascade in the plurality corresponds to one of the one or more imaged channels and operates on the input independent of another cascade.

7. The neural network-implemented method of claim 1, further including:
the 3D convolutions separately applying a respective convolution kernel on each of the imaged channels and producing at least one intermediate output feature for each of the one or more imaged channels;
the 3D convolutions not combining intermediate output features of the one or more imaged channels and instead making them available as imaged channel-specific output features;
supplementing the imaged channel-specific output features with cross-cycle intensity data features from a corresponding imaged channel of one or more of the pixels that contain the intensity data for one or more of the associated analytes to be base called; and
beginning with the imaged channel-specific output features supplemented with the intensity data features as starting input, applying the cascade of 1D convolutions.

8. The neural network-implemented method of claim 1, further including:
the 3D convolutions separately applying a respective convolution kernel on each of the one or more imaged channels and producing at least one intermediate output feature for each of the imaged channels;
the 3D convolutions not combining intermediate output features of the one or more imaged channels and instead making them available as imaged channel-specific output features;
supplementing the imaged channel-specific output features with cross-cycle intensity data features from the corresponding imaged channel of one or more of the pixels that contain the intensity data for one or more of the associated analytes to be base called; and
beginning with the imaged channel-specific output features supplemented with the intensity data features as starting input, applying a plurality of cascade of 1D convolutions such that each cascade in the plurality corresponds to one of the one or more imaged channels and operates on the input independent of another cascade.

9. The neural network-implemented method of claim 1, further including:
the 1D convolutions mixing information between respective per-cycle elements of each of the output features and the intensity data features on a sliding window basis and producing at least one intermediate output feature for each of the output features and the intensity data features; and
the 1D convolutions accumulating information across intermediate output features of the output features on a per-cycle element basis and producing further output features.

10. The neural network-implemented method of claim 9, wherein size of the sliding window for the sliding window is based on a receptive field of the 1D convolutions and varies in the cascade.

11. The neural network-implemented method of claim 1, further including:
applying a combination of the 1D convolutions and transposed convolutions instead of the cascade of 1D convolutions, wherein the combination alternates between application of the 1D convolutions and the transposed convolutions.

12. The neural network-implemented method of claim 1, further including:
the pointwise convolutions respectively convolving over further output features on a per-cycle element basis and producing at least one intermediate output feature for each of the further output features; and
the pointwise convolutions accumulating information across intermediate output features of the further output features on a per-cycle element basis and producing at least one final output feature.

13. The neural network-implemented method of claim 2, further including:
using the normalized per-cycle values in the final output features of the one or more imaged channels to assign quality scores to base call predictions emitted by the output layer based on a quality score mapping, wherein the quality score mapping is determined by:
calculating predicted error rates for base call predictions made on training data and determining corresponding predicted quality scores;
determining a fit between the predicted quality scores and empirical quality scores determined from empirical base calling error rates derived from test data; and
correlating the predicted quality scores to the empirical quality scores based on the fit.

14. The neural network-implemented method of claim 13, further including learning kernel weights of convolution filters applied by the 3D convolutions, the 1D convolutions, and the pointwise convolutions using a backpropagation-based gradient update technique that progressively matches the base call predictions emitted by the output layer with ground truth.

15. The neural network-implemented method of claim 14, wherein the ground truth includes per-cycle binary values for each of the one or more imaged channels, further including:
the backpropagation-based gradient update technique computing an error between the per-cycle binary values in the ground truth and the corresponding per-cycle binary values in the final output features of the one or more imaged channels.

16. The neural network-implemented method of claim 14, wherein the ground truth includes a one-hot encoding identifying a correct base, further including:
the backpropagation-based gradient update technique computing an error between the one-hot encoding in the ground truth and an exponentially normalized probability distribution produced by a softmax function.

17. The neural network-implemented method of claim 14, further including varying a learning rate of learning.

18. The neural network-implemented method of claim 1, further including extracting the per-cycle image patches from respective per-cycle images of a tile of a flow cell on which the analytes are disposed.

19. The neural network-implemented method of claim 18, further including base calling analytes disposed throughout the tile by extracting per-cycle image patches from overlapping regions of the tile such that the extracted per-cycle image patches have overlapping pixels.

20. The neural network-implemented method of claim 1, wherein the 1D convolutions use bilinear form product to mix information.

* * * * *